United States Patent
Sganga et al.

(10) Patent No.: US 11,779,406 B2
(45) Date of Patent: *Oct. 10, 2023

(54) SYSTEMS AND METHODS FOR GUIDANCE OF INTRALUMINAL DEVICES WITHIN THE VASCULATURE

(71) Applicant: Remedy Robotics, Inc., San Francisco, CA (US)

(72) Inventors: Jake Anthony Sganga, San Francisco, CA (US); David James Bell, San Francisco, CA (US); Benjamin Fredrickson, Gualala, CA (US); Gregory Kahn, Berkeley, CA (US)

(73) Assignee: REMEDY ROBOTICS, INC., San Francisco, CA (US)

( * ) Notice: Subject to any disclaimer, the term of this patent is extended or adjusted under 35 U.S.C. 154(b) by 97 days.

This patent is subject to a terminal disclaimer.

(21) Appl. No.: 17/646,850

(22) Filed: Jan. 3, 2022

(65) Prior Publication Data
US 2022/0202506 A1 Jun. 30, 2022

Related U.S. Application Data

(63) Continuation of application No. 17/389,973, filed on Jul. 30, 2021, now Pat. No. 11,229,488, which is a
(Continued)

(51) Int. Cl.
*A61B 34/20* (2016.01)
*G16H 30/40* (2018.01)
(Continued)

(52) U.S. Cl.
CPC ........... *A61B 34/20* (2016.02); *A61B 34/25* (2016.02); *A61B 34/35* (2016.02); *G16H 20/40* (2018.01);
(Continued)

(58) Field of Classification Search
CPC ......... A61B 34/20; A61B 34/25; A61B 34/35; A61B 2034/2065; A61B 2034/303;
(Continued)

(56) References Cited

U.S. PATENT DOCUMENTS

| 819,885 A | 5/1906 | Holmen |
|---|---|---|
| 5,456,574 A | 10/1995 | Bos et al. |

(Continued)

FOREIGN PATENT DOCUMENTS

| CN | 105125241 | 12/2015 |
|---|---|---|
| DE | 20 2012 006 263 | 9/2013 |

(Continued)

OTHER PUBLICATIONS

International Search Report for International Application No. PCT/US2022/040118 dated Nov. 22, 2022.
(Continued)

*Primary Examiner* — Sanjay Cattungal
(74) *Attorney, Agent, or Firm* — Knobbe Martens Olson & Bear LLP

(57) ABSTRACT

System for guiding an instrument within a vascular network of a patient are disclosed. In some embodiments, the system receives a medical image from a medical imaging device and identifies a distal tip and a direction the instrument in the image. The system may then determine a waypoint for the distal tip of the instrument based at least in part on the position and direction of the distal tip of the instrument. The system may then generate a trajectory command for moving the instrument through the vascular network from the current position to the waypoint. The system may operate in a closed loop. The system may provide the trajectory command to a robotic medical system configured to move the instrument according to the command.

20 Claims, 27 Drawing Sheets

Related U.S. Application Data continuation of application No. 17/350,999, filed on Jun. 17, 2021, now Pat. No. 11,197,725.

(60) Provisional application No. 63/074,340, filed on Sep. 3, 2020, provisional application No. 63/041,538, filed on Jun. 19, 2020.

(51) Int. Cl.

| | | |
|---|---|---|
| *G16H 40/63* | (2018.01) | |
| *G16H 20/40* | (2018.01) | |
| *A61B 34/00* | (2016.01) | |
| *A61B 34/35* | (2016.01) | |
| *A61B 90/00* | (2016.01) | |
| *A61B 34/30* | (2016.01) | |

(52) U.S. Cl.
CPC ............. *G16H 30/40* (2018.01); *G16H 40/63* (2018.01); *A61B 2034/2065* (2016.02); *A61B 2034/303* (2016.02); *A61B 2090/064* (2016.02); *A61B 2090/3762* (2016.02)

(58) Field of Classification Search
CPC ...... A61B 2090/064; A61B 2090/3762; A61B 34/30; A61B 2034/301; G16H 20/40; G16H 30/40; G16H 40/63

See application file for complete search history.

(56) References Cited

U.S. PATENT DOCUMENTS

| | | | |
|---|---|---|---|
| 5,607,393 | A | 3/1997 | Ensminger et al. |
| 5,792,123 | A | 8/1998 | Ensminger |
| 6,132,368 | A | 10/2000 | Cooper |
| 6,171,329 | B1 | 1/2001 | Shaw et al. |
| 6,203,568 | B1 | 3/2001 | Lombardi et al. |
| 6,361,557 | B1 | 3/2002 | Gittings et al. |
| 6,522,933 | B2 | 2/2003 | Nguyen |
| 6,572,610 | B2 | 6/2003 | Kovalcheck et al. |
| 6,592,581 | B2 | 7/2003 | Bowe |
| 6,602,267 | B2 | 8/2003 | Castaneda |
| 6,623,508 | B2 | 9/2003 | Shaw et al. |
| 6,645,218 | B1 | 11/2003 | Cassidy et al. |
| 6,648,875 | B2 | 11/2003 | Simpson et al. |
| 6,652,506 | B2 | 11/2003 | Bowe et al. |
| 6,669,692 | B1 | 12/2003 | Nelson |
| 6,743,239 | B1 | 6/2004 | Kuehn et al. |
| 6,858,005 | B2 | 2/2005 | Ohline et al. |
| 6,860,878 | B2 | 3/2005 | Brock |
| 6,869,414 | B2 | 3/2005 | Simpson et al. |
| 6,872,433 | B2 | 3/2005 | Seward et al. |
| 6,926,711 | B2 | 8/2005 | Lentz et al. |
| 6,979,312 | B2 | 12/2005 | Shimada |
| 6,986,769 | B2 | 1/2006 | Nelson et al. |
| 7,011,655 | B2 | 3/2006 | Thompson et al. |
| 7,052,489 | B2 | 5/2006 | Griego et al. |
| 7,122,020 | B2 | 10/2006 | Mogul |
| 7,285,108 | B2 | 10/2007 | Koerner et al. |
| 7,331,967 | B2 | 2/2008 | Lee et al. |
| 7,357,774 | B2 | 4/2008 | Cooper |
| 7,379,790 | B2 | 5/2008 | Toth |
| 7,419,477 | B2 | 9/2008 | Simpson et al. |
| 7,503,914 | B2 | 3/2009 | Coleman et al. |
| 7,608,056 | B2 | 10/2009 | Kennedy, II |
| 7,615,044 | B2 | 11/2009 | Scheibe et al. |
| 7,717,875 | B2 | 5/2010 | Knudson et al. |
| 7,731,706 | B2 | 6/2010 | Potter |
| 7,758,569 | B2 | 7/2010 | Brock |
| 7,789,875 | B2 | 9/2010 | Brock et al. |
| 7,803,130 | B2 | 9/2010 | Ryan et al. |
| 7,819,884 | B2 | 10/2010 | Lee et al. |
| 7,840,261 | B2 | 11/2010 | Rosenman et al. |
| 7,942,854 | B1 | 5/2011 | Von Oepen et al. |
| 7,947,050 | B2 | 5/2011 | Lee et al. |
| 7,947,051 | B2 | 5/2011 | Lee et al. |
| 7,963,913 | B2 | 6/2011 | Devengenzo et al. |
| 7,972,323 | B1 | 7/2011 | Bencini et al. |
| 8,000,764 | B2 | 8/2011 | Rashidi |
| 8,002,739 | B2 | 8/2011 | Lee et al. |
| 8,016,784 | B1 | 9/2011 | Hayzelden et al. |
| 8,052,607 | B2 | 11/2011 | Byrd |
| 8,062,212 | B2 | 11/2011 | Belson |
| 8,066,664 | B2 | 11/2011 | LaDuca et al. |
| 8,118,803 | B1 | 2/2012 | Chow |
| 8,137,263 | B2 | 3/2012 | Marescaux et al. |
| 8,142,367 | B2 | 3/2012 | Gardeski et al. |
| 8,162,934 | B2 | 4/2012 | Potter |
| 8,170,657 | B1 | 5/2012 | Ehrenreich |
| 8,182,470 | B2 | 5/2012 | Devengenzo et al. |
| 8,192,399 | B2 | 6/2012 | Birchard |
| 8,214,019 | B2 | 7/2012 | Govari et al. |
| 8,218,846 | B2 | 7/2012 | Trumer et al. |
| 8,231,610 | B2 | 7/2012 | Jo et al. |
| 8,251,977 | B2 | 8/2012 | Partlett |
| 8,256,428 | B2 | 9/2012 | Hindricks et al. |
| 8,273,016 | B2 | 9/2012 | O'Sullivan |
| 8,273,054 | B2 | 9/2012 | St. Germain et al. |
| 8,295,943 | B2 | 10/2012 | Eggen et al. |
| 8,298,177 | B2 | 10/2012 | Selkee |
| 8,303,576 | B2 | 11/2012 | Brock |
| 8,348,931 | B2 | 1/2013 | Cooper et al. |
| 8,372,033 | B2 | 2/2013 | Kronstedt et al. |
| 8,388,572 | B2 | 3/2013 | Olsen et al. |
| 8,409,245 | B2 | 4/2013 | Lee |
| 8,409,273 | B2 | 4/2013 | Thornton et al. |
| 8,414,598 | B2 | 4/2013 | Brock et al. |
| 8,460,236 | B2 | 6/2013 | Roelle et al. |
| 8,486,022 | B2 | 7/2013 | Ludwig et al. |
| 8,506,555 | B2 | 8/2013 | Morales |
| 8,506,562 | B2 | 8/2013 | Anderson et al. |
| 8,517,923 | B2 | 8/2013 | Belson et al. |
| 8,529,582 | B2 | 9/2013 | Devengenzo et al. |
| 8,568,435 | B2 | 10/2013 | Pillai et al. |
| 8,603,135 | B2 | 12/2013 | Mueller |
| 8,607,935 | B2 | 12/2013 | Goldberg et al. |
| 8,608,773 | B2 | 12/2013 | Tierney et al. |
| 8,620,400 | B2 | 12/2013 | de la Rama et al. |
| 8,632,468 | B2 | 1/2014 | Glossop et al. |
| 8,636,764 | B2 | 1/2014 | Miles et al. |
| 8,641,602 | B2 | 2/2014 | Belson |
| 8,641,700 | B2 | 2/2014 | Devengenzo et al. |
| 8,647,362 | B2 | 2/2014 | Griego |
| 8,671,817 | B1 | 3/2014 | Bogusky |
| 8,672,837 | B2 | 3/2014 | Roelle et al. |
| 8,672,922 | B2 | 3/2014 | Loh et al. |
| 8,690,871 | B2 | 4/2014 | Partlett et al. |
| 8,706,260 | B2 | 4/2014 | Stewart et al. |
| 8,709,037 | B2 | 4/2014 | Lee et al. |
| 8,715,318 | B2 | 5/2014 | Miles et al. |
| 8,721,530 | B2 | 5/2014 | Ohline et al. |
| D708,740 | S | 7/2014 | Osypka et al. |
| 8,808,169 | B2 | 8/2014 | Macnamara et al. |
| 8,808,278 | B2 | 8/2014 | Goldberg et al. |
| 8,827,948 | B2 | 9/2014 | Romo et al. |
| 8,834,489 | B2 | 9/2014 | Cooper et al. |
| 8,840,560 | B2 | 9/2014 | Hossack et al. |
| 8,864,656 | B2 | 10/2014 | Konstorum |
| D718,437 | S | 11/2014 | Osypka |
| 8,894,610 | B2 | 11/2014 | Macnamara et al. |
| 8,920,429 | B2 | 12/2014 | Hinman et al. |
| 8,939,960 | B2 | 1/2015 | Rosenman et al. |
| 8,961,533 | B2 | 2/2015 | Stahler et al. |
| 8,979,740 | B2 | 3/2015 | Butler |
| 9,005,217 | B2 | 4/2015 | Govari et al. |
| 9,023,060 | B2 | 5/2015 | Cooper et al. |
| 9,061,120 | B2 | 6/2015 | Osypka et al. |
| 9,084,621 | B2 | 7/2015 | Weitzner et al. |
| 9,085,085 | B2 | 7/2015 | Danitz et al. |
| 9,089,356 | B2 | 7/2015 | Chen et al. |
| 9,095,253 | B2 | 8/2015 | Hinman et al. |
| 9,101,379 | B2 | 8/2015 | Au et al. |
| 9,101,735 | B2 | 8/2015 | Rothe et al. |
| 9,107,673 | B2 | 8/2015 | Chong et al. |

(56) References Cited

U.S. PATENT DOCUMENTS

| | | |
|---|---|---|
| 9,114,232 B2 | 8/2015 | Olson et al. |
| 9,138,166 B2 | 9/2015 | Wong et al. |
| 9,149,937 B2 | 10/2015 | Goldberg et al. |
| 9,155,449 B2 | 10/2015 | Danitz et al. |
| 9,173,551 B2 | 11/2015 | Peters et al. |
| 9,173,713 B2 | 11/2015 | Hart et al. |
| 9,186,046 B2 | 11/2015 | Ramamurthy et al. |
| 9,199,061 B2 | 12/2015 | Selkee |
| 9,204,933 B2 | 12/2015 | Reis et al. |
| 9,241,770 B2 | 1/2016 | Stokes et al. |
| 9,254,372 B2 | 2/2016 | Ryan |
| 9,259,271 B2 | 2/2016 | Anvari et al. |
| 9,308,349 B2 | 4/2016 | Rezac et al. |
| 9,314,587 B2 | 4/2016 | Arnim et al. |
| 9,314,591 B2 | 4/2016 | Ogle |
| 9,326,822 B2 | 5/2016 | Lewis et al. |
| 9,333,324 B2 | 5/2016 | Cohen et al. |
| 9,351,716 B2 | 5/2016 | Miles et al. |
| 9,364,636 B2 | 6/2016 | Grewe et al. |
| 9,370,868 B2 | 6/2016 | Danitz et al. |
| 9,399,300 B2 | 7/2016 | Goldberg et al. |
| 9,427,282 B2 | 8/2016 | Belson et al. |
| 9,434,077 B2 | 9/2016 | Danitz et al. |
| 9,439,732 B2 | 9/2016 | Devengenzo et al. |
| 9,474,527 B1 | 10/2016 | Knodel et al. |
| 9,477,301 B2 | 10/2016 | Kishi |
| 9,480,533 B2 | 11/2016 | Devengenzo et al. |
| 9,492,192 B2 | 11/2016 | To et al. |
| 9,498,602 B2 | 11/2016 | Osypka et al. |
| 9,504,371 B2 | 11/2016 | Mitchell et al. |
| 9,504,372 B2 | 11/2016 | Kim |
| 9,510,885 B2 | 12/2016 | Burger et al. |
| 9,517,326 B2 | 12/2016 | Hinman et al. |
| 9,533,122 B2 | 1/2017 | Weitzner et al. |
| 9,572,957 B2 | 2/2017 | Osypka et al. |
| D782,037 S | 3/2017 | Osypka et al. |
| 9,585,647 B2 | 3/2017 | Clark |
| 9,597,514 B2 | 3/2017 | Khairkhahan et al. |
| 9,622,729 B2 | 4/2017 | Dewaele et al. |
| 9,636,483 B2 | 5/2017 | Hart et al. |
| 9,642,514 B2 | 5/2017 | Gilboa |
| 9,662,473 B2 | 5/2017 | McDaniel et al. |
| 9,675,422 B2 | 6/2017 | Hourtash et al. |
| 9,693,759 B2 | 7/2017 | Seguy |
| 9,693,780 B2 | 7/2017 | Miles et al. |
| 9,713,509 B2 | 7/2017 | Schuh et al. |
| 9,724,163 B2 | 8/2017 | Orban |
| 9,737,365 B2 | 8/2017 | Hegeman et al. |
| 9,737,371 B2 | 8/2017 | Romo et al. |
| 9,743,990 B2 | 8/2017 | Au et al. |
| 9,744,335 B2 | 8/2017 | Jiang |
| 9,750,577 B2 | 9/2017 | Pacheco et al. |
| 9,757,149 B2 | 9/2017 | Cooper et al. |
| 9,757,538 B2 | 9/2017 | Kimmel et al. |
| 9,763,741 B2 | 9/2017 | Alvarez et al. |
| 9,775,963 B2 | 10/2017 | Miller |
| 9,782,130 B2 | 10/2017 | Hauck et al. |
| 9,814,490 B2 | 11/2017 | Neoh et al. |
| 9,844,412 B2 | 12/2017 | Bogusky et al. |
| 9,848,949 B2 | 12/2017 | Osypka |
| 9,861,790 B2 | 1/2018 | Selkee |
| 9,867,982 B2 | 1/2018 | Berthiaume et al. |
| 9,877,781 B2 | 1/2018 | Grasse et al. |
| 9,883,864 B2 | 2/2018 | Miles et al. |
| 9,889,273 B2 | 2/2018 | Cully et al. |
| 9,895,813 B2 | 2/2018 | Blumenkranz et al. |
| 9,901,408 B2 | 2/2018 | Larkin |
| 9,907,570 B2 | 3/2018 | Osypka et al. |
| 9,913,684 B2 | 3/2018 | Osypka |
| 9,937,322 B2 | 4/2018 | Drake et al. |
| 9,949,749 B2 | 4/2018 | Noonan et al. |
| 9,955,986 B2 | 5/2018 | Shah |
| 9,956,051 B2 | 5/2018 | Stokes et al. |
| 9,962,066 B2 | 5/2018 | Rogers et al. |
| 9,968,241 B2 | 5/2018 | Iuel |
| 9,974,619 B2 | 5/2018 | Goldenberg et al. |
| 9,993,211 B2 | 6/2018 | Tokuda et al. |
| 9,993,313 B2 | 6/2018 | Schuh et al. |
| 10,010,367 B2 | 7/2018 | Chien et al. |
| 10,010,699 B2 | 7/2018 | Cohen et al. |
| 10,010,700 B2 | 7/2018 | Romoscanu |
| 10,016,187 B2 | 7/2018 | Castro |
| 10,016,191 B2 | 7/2018 | Kaiser et al. |
| 10,029,073 B2 | 7/2018 | Kabe et al. |
| 10,029,074 B2 | 7/2018 | Mogul |
| 10,035,002 B2 | 7/2018 | Weiss |
| 10,039,436 B2 | 8/2018 | Tah et al. |
| 10,076,337 B2 | 9/2018 | Miles et al. |
| 10,080,608 B2 | 9/2018 | Datta et al. |
| 10,099,036 B2 | 10/2018 | Heideman et al. |
| 10,130,427 B2 | 11/2018 | Tanner et al. |
| 10,143,360 B2 | 12/2018 | Roelle et al. |
| 10,159,533 B2 | 12/2018 | Moll et al. |
| 10,173,073 B2 | 1/2019 | Webler, Jr. et al. |
| 10,188,273 B2 | 1/2019 | Tilson et al. |
| 10,188,832 B2 | 1/2019 | Salahieh et al. |
| 10,201,394 B2 | 2/2019 | Yanagihara et al. |
| 10,219,874 B2 | 3/2019 | Yu et al. |
| 10,238,837 B2 | 3/2019 | Duindam et al. |
| 10,265,502 B2 | 4/2019 | Tsai et al. |
| 10,286,183 B2 | 5/2019 | Flygare et al. |
| 10,292,719 B2 | 5/2019 | Burger et al. |
| 10,300,286 B2 | 5/2019 | Ward et al. |
| 10,307,214 B2 | 6/2019 | Lathrop et al. |
| 10,321,923 B2 | 6/2019 | DeGraaf et al. |
| 10,321,964 B2 | 6/2019 | Grover et al. |
| 10,327,625 B2 | 6/2019 | Belson et al. |
| 10,335,243 B2 | 7/2019 | Yanagihara et al. |
| 10,342,411 B2 | 7/2019 | Japerson et al. |
| 10,342,625 B2 | 7/2019 | Loh et al. |
| 10,349,943 B2 | 7/2019 | Noonan et al. |
| 10,363,109 B2 | 7/2019 | Dachs et al. |
| 10,376,170 B2 | 8/2019 | Quinn et al. |
| 10,398,499 B2 | 9/2019 | Clark et al. |
| 10,405,939 B2 | 9/2019 | Romo |
| 10,405,940 B2 | 9/2019 | Romo |
| 10,413,708 B2 | 9/2019 | Loh |
| 10,426,557 B2 | 10/2019 | Amiri et al. |
| 10,426,560 B2 | 10/2019 | Bowling et al. |
| 10,454,347 B2 | 10/2019 | Covington et al. |
| 10,456,166 B2 | 10/2019 | Cooper et al. |
| 10,463,439 B2 | 11/2019 | Joseph et al. |
| 10,463,440 B2 | 11/2019 | Bowling et al. |
| 10,470,830 B2 | 11/2019 | Hill et al. |
| 10,478,296 B2 | 11/2019 | Le et al. |
| 10,482,599 B2 | 11/2019 | Mintz et al. |
| 10,485,621 B2 | 11/2019 | Morrissette et al. |
| 10,493,239 B2 | 12/2019 | Hart et al. |
| 10,493,241 B2 | 12/2019 | Jiang |
| 10,500,373 B2 | 12/2019 | Barrish et al. |
| 10,507,063 B2 | 12/2019 | Zuhars |
| 10,512,757 B2 | 12/2019 | Laby et al. |
| 10,525,233 B2 | 1/2020 | Barrish et al. |
| 10,525,257 B2 | 1/2020 | Govea et al. |
| 10,537,385 B2 | 1/2020 | Wu et al. |
| 10,537,713 B2 | 1/2020 | Kidd et al. |
| 10,543,047 B2 | 1/2020 | Yu |
| 10,555,780 B2 | 2/2020 | Tanner et al. |
| 10,556,092 B2 | 2/2020 | Yu et al. |
| 10,568,708 B2 | 2/2020 | Au et al. |
| 10,575,745 B2 | 3/2020 | Solis |
| 10,576,243 B2 | 3/2020 | Suon et al. |
| 10,582,929 B2 | 3/2020 | Miles et al. |
| 10,583,271 B2 | 3/2020 | Bogusky |
| 10,588,495 B2 | 3/2020 | Simmons et al. |
| 10,588,620 B2 | 3/2020 | Caffes et al. |
| 10,603,124 B2 | 3/2020 | Camarillo et al. |
| 10,610,312 B2 | 4/2020 | Srivastava et al. |
| 10,610,320 B2 | 4/2020 | Dachs et al. |
| 10,617,402 B2 | 4/2020 | Reddy et al. |
| 10,617,848 B2 | 4/2020 | Weitzner et al. |
| 10,631,937 B2 | 4/2020 | Tyulmankov et al. |
| 10,631,949 B2 | 4/2020 | Schuh et al. |
| 10,632,281 B2 | 4/2020 | Rosenman et al. |

(56) References Cited

U.S. PATENT DOCUMENTS

| | | |
|---|---|---|
| 10,646,696 B2 | 5/2020 | Barrish et al. |
| 10,667,871 B2 | 6/2020 | Romo et al. |
| 10,682,503 B2 | 6/2020 | Gerrans et al. |
| 10,687,691 B2 | 6/2020 | Smith et al. |
| 10,695,536 B2 | 6/2020 | Weitzner et al. |
| 10,709,512 B2 | 7/2020 | Bajo et al. |
| 10,737,064 B1 | 8/2020 | Ju |
| 10,737,073 B2 | 8/2020 | Barrish et al. |
| 10,744,303 B2 | 8/2020 | Duindam et al. |
| 10,758,310 B2 | 9/2020 | Shelton, IV |
| 10,758,714 B2 | 9/2020 | Laby et al. |
| 10,765,486 B2 | 9/2020 | Bajo et al. |
| 10,772,637 B2 | 9/2020 | Miles et al. |
| 10,779,710 B2 | 9/2020 | Matthison-Hansen |
| 10,779,803 B2 | 9/2020 | Prisco et al. |
| 10,779,898 B2 | 9/2020 | Hill et al. |
| 10,786,329 B2 | 9/2020 | Schuh et al. |
| 10,792,061 B2 | 10/2020 | Dewaele et al. |
| 10,792,464 B2 | 10/2020 | Romo et al. |
| 10,792,468 B2 | 10/2020 | Bolduc et al. |
| 10,799,096 B2 | 10/2020 | Golden et al. |
| 10,799,224 B2 | 10/2020 | Tasci |
| 10,806,897 B2 | 10/2020 | Furnish |
| 10,806,899 B2 | 10/2020 | Laby et al. |
| 10,813,708 B2 | 10/2020 | Reinstein et al. |
| 10,814,101 B2 | 10/2020 | Jiang |
| 10,814,102 B2 | 10/2020 | Laby et al. |
| 10,881,832 B2 | 1/2021 | Chu |
| 10,932,877 B2 | 3/2021 | Devengenzo et al. |
| 10,939,972 B2 | 3/2021 | Au |
| 10,939,973 B2 | 3/2021 | DiMaio et al. |
| 10,944,728 B2 | 3/2021 | Wiener |
| 11,058,508 B2 | 7/2021 | Scheib et al. |
| 11,129,685 B2 | 9/2021 | Zemlok et al. |
| 11,160,621 B2 | 11/2021 | Steger |
| 11,213,362 B2 | 1/2022 | Sharon et al. |
| 11,241,291 B2 | 2/2022 | Sharon et al. |
| 11,259,881 B2 | 3/2022 | Kilroy et al. |
| 11,284,956 B2 | 3/2022 | Zemlok et al. |
| 11,318,297 B2 | 5/2022 | Li et al. |
| 11,369,450 B2 | 6/2022 | Bernstein |
| 11,406,465 B2 | 8/2022 | Zemlok et al. |
| 11,419,691 B2 | 8/2022 | Kim et al. |
| 11,446,105 B2 | 9/2022 | Dachs et al. |
| 2007/0078334 A1 | 4/2007 | Scully |
| 2008/0119872 A1 | 5/2008 | Brock et al. |
| 2008/0125793 A1 | 5/2008 | Brock et al. |
| 2008/0125794 A1 | 5/2008 | Brock et al. |
| 2008/0177285 A1 | 7/2008 | Brock et al. |
| 2008/0228065 A1 | 9/2008 | Viswanathan et al. |
| 2008/0262301 A1 | 10/2008 | Gibbons et al. |
| 2008/0319314 A1 | 12/2008 | Hill et al. |
| 2009/0105700 A1 | 4/2009 | Anderson |
| 2009/0171147 A1 | 7/2009 | Lee et al. |
| 2009/0324161 A1 | 12/2009 | Prisco |
| 2010/0204646 A1 | 8/2010 | Plicchi et al. |
| 2010/0234938 A1 | 9/2010 | Taheri et al. |
| 2010/0249497 A1 | 9/2010 | Peine et al. |
| 2011/0046441 A1 | 2/2011 | Wiltshire et al. |
| 2011/0066161 A1 | 3/2011 | Cooper |
| 2011/0154473 A1 | 6/2011 | Anderson et al. |
| 2011/0213383 A1 | 9/2011 | Lee et al. |
| 2011/0276034 A1 | 11/2011 | Tomarelli et al. |
| 2011/0319714 A1 | 12/2011 | Roelle et al. |
| 2012/0016311 A1 | 1/2012 | Altman et al. |
| 2012/0253324 A1 | 10/2012 | Lee et al. |
| 2012/0287238 A1 | 11/2012 | Onishi |
| 2013/0041314 A1 | 2/2013 | Dillon |
| 2013/0158509 A1 | 6/2013 | Consigny et al. |
| 2013/0253469 A1 | 9/2013 | Freed |
| 2015/0045696 A1 | 2/2015 | Osypka |
| 2015/0057610 A1 | 2/2015 | Osypka et al. |
| 2015/0105721 A1 | 4/2015 | Osypka et al. |
| 2015/0164594 A1 | 6/2015 | Romo et al. |
| 2015/0202020 A1 | 7/2015 | Fisher |
| 2015/0335383 A9 | 11/2015 | Cohen |
| 2016/0067457 A1 | 3/2016 | Selkee |
| 2016/0113711 A1 | 4/2016 | Osypka et al. |
| 2016/0213423 A1 | 7/2016 | Kauphusman et al. |
| 2016/0213884 A1 | 7/2016 | Park |
| 2016/0228032 A1 | 8/2016 | Walker et al. |
| 2016/0287226 A1 | 10/2016 | Al-Obani et al. |
| 2017/0106170 A1 | 4/2017 | Hsueh et al. |
| 2017/0224199 A1 | 8/2017 | Demers et al. |
| 2017/0273665 A1 | 9/2017 | Kapoor et al. |
| 2017/0312002 A1 | 11/2017 | Sliwa et al. |
| 2018/0085552 A1 | 3/2018 | Miller |
| 2018/0104007 A1 | 4/2018 | Scheller et al. |
| 2018/0117280 A1 | 5/2018 | Chu |
| 2018/0140177 A1 | 5/2018 | Liu et al. |
| 2018/0207402 A1 | 7/2018 | Tegg |
| 2018/0228557 A1 | 8/2018 | Darisse et al. |
| 2018/0333212 A1 | 11/2018 | Goldenberg et al. |
| 2018/0344979 A1 | 12/2018 | Schultz |
| 2019/0000546 A1 | 1/2019 | Romoscanu |
| 2019/0008601 A1 | 1/2019 | Pereira et al. |
| 2019/0015633 A1 | 1/2019 | Bednarek et al. |
| 2019/0022356 A1 | 1/2019 | Bansal et al. |
| 2019/0076093 A1 | 3/2019 | Saroha et al. |
| 2019/0076160 A1 | 3/2019 | Lin et al. |
| 2019/0105481 A1 | 4/2019 | Lin et al. |
| 2019/0111239 A1 | 4/2019 | Bolduc et al. |
| 2019/0142413 A1 | 5/2019 | Fairneny |
| 2019/0142591 A1 | 5/2019 | Rohl et al. |
| 2019/0151614 A1 | 5/2019 | Hsueh et al. |
| 2019/0209810 A1 | 7/2019 | Reid et al. |
| 2019/0216486 A1 | 7/2019 | Weitzman |
| 2019/0223734 A1 | 7/2019 | Lakkireddy et al. |
| 2019/0224466 A1 | 7/2019 | Oliverius et al. |
| 2019/0254690 A1 | 8/2019 | Cabiri et al. |
| 2019/0255292 A1 | 8/2019 | Osypka et al. |
| 2019/0269368 A1 | 9/2019 | Hauck et al. |
| 2019/0274757 A1 | 9/2019 | Mahapatra et al. |
| 2019/0290886 A1 | 9/2019 | Campbell et al. |
| 2019/0298969 A1 | 10/2019 | Dale et al. |
| 2019/0307517 A1 | 10/2019 | Arai |
| 2019/0314052 A1 | 10/2019 | Thapliyal et al. |
| 2019/0314608 A1 | 10/2019 | Della Vecchia |
| 2019/0321597 A1 | 10/2019 | Van Hoven et al. |
| 2019/0365204 A1 | 12/2019 | Lang et al. |
| 2019/0365536 A1 | 12/2019 | Prabhu |
| 2019/0366040 A1 | 12/2019 | Golden et al. |
| 2019/0388099 A1 | 12/2019 | Zuhars et al. |
| 2020/0015911 A1 | 1/2020 | Yi |
| 2020/0023151 A1 | 1/2020 | Karlsson et al. |
| 2020/0060683 A1 | 2/2020 | Friedman et al. |
| 2020/0060820 A1 | 2/2020 | Ben-Zvi et al. |
| 2020/0069389 A1 | 3/2020 | Morrissette et al. |
| 2020/0078019 A1 | 3/2020 | Dell et al. |
| 2020/0085483 A1 | 3/2020 | Tegg et al. |
| 2020/0100896 A1 | 4/2020 | Jimenez et al. |
| 2020/0138454 A1 | 5/2020 | Patel et al. |
| 2020/0179650 A1 | 6/2020 | Beeckler et al. |
| 2020/0179651 A1 | 6/2020 | Scheltes et al. |
| 2020/0196896 A1 | 6/2020 | Solis |
| 2020/0197111 A1 | 6/2020 | Kim et al. |
| 2020/0222139 A1 | 7/2020 | Dachs et al. |
| 2020/0222667 A1 | 7/2020 | Tang et al. |
| 2020/0230354 A1 | 7/2020 | von Oepen et al. |
| 2020/0230360 A1 | 7/2020 | Yu et al. |
| 2020/0269017 A1 | 8/2020 | Winston et al. |
| 2020/0276415 A1 | 9/2020 | Tang et al. |
| 2020/0289224 A1 | 9/2020 | Johnson et al. |
| 2020/0289789 A1 | 9/2020 | Scheibe et al. |
| 2020/0297444 A1 | 9/2020 | Camarillo |
| 2020/0297971 A1 | 9/2020 | Beeckler et al. |
| 2020/0330729 A1 | 10/2020 | Petitpierre et al. |
| 2020/0337766 A1 | 10/2020 | Dando et al. |
| 2020/0337792 A1 | 10/2020 | Zemlok et al. |
| 2020/0383734 A1 | 12/2020 | Dahdouh |
| 2020/0405397 A1 | 12/2020 | Liu |
| 2021/0015573 A1 | 1/2021 | Tsao et al. |
| 2021/0030496 A1 | 2/2021 | Devengenzo et al. |
| 2021/0045626 A1 | 2/2021 | Hsu |

(56) References Cited

U.S. PATENT DOCUMENTS

| | | |
|---|---|---|
| 2021/0153961 A1 | 5/2021 | DiMaio et al. |
| 2021/0154473 A1 | 5/2021 | Pobiel |
| 2021/0220060 A1 | 7/2021 | Kapadia et al. |
| 2021/0236773 A1 | 8/2021 | Dupont |
| 2021/0267702 A1 | 9/2021 | Kim et al. |
| 2021/0267703 A1 | 9/2021 | Devengenzo et al. |
| 2022/0000570 A1 | 1/2022 | Steger |
| 2022/0008152 A1 | 1/2022 | Daniel |
| 2022/0044057 A1 | 2/2022 | Ganesan et al. |
| 2022/0071723 A1 | 3/2022 | Sharon et al. |
| 2022/0230348 A1 | 7/2022 | Huber et al. |
| 2022/0273388 A1 | 9/2022 | Bernstein |
| 2022/0296321 A1 | 9/2022 | Sharon et al. |
| 2022/0296322 A1 | 9/2022 | Gomez et al. |
| 2022/0304758 A1 | 9/2022 | Scheib et al. |
| 2022/0361959 A1 | 11/2022 | Weber et al. |

FOREIGN PATENT DOCUMENTS

| | | |
|---|---|---|
| WO | WO 2013/141011 | 9/2013 |
| WO | WO 2017003453 A1 | 1/2017 |
| WO | WO 2017/070193 | 4/2017 |
| WO | WO 2017115352 A1 | 7/2017 |
| WO | WO 2017/155867 | 9/2017 |
| WO | WO 2018/080470 | 5/2018 |
| WO | WO 2018/204202 | 7/2018 |
| WO | WO 2019/089053 | 5/2019 |
| WO | WO 2019/136357 | 7/2019 |
| WO | WO 2019/156559 | 8/2019 |
| WO | WO 2019/240655 | 12/2019 |
| WO | WO 2020/150709 | 7/2020 |
| WO | WO 2020/187663 | 9/2020 |
| WO | WO 2021/138096 | 7/2021 |
| WO | WO 2022066730 A1 | 3/2022 |

OTHER PUBLICATIONS

International Search Report for International Application No. PCT/US2022/035848 dated Aug. 12, 2022.

Buther F, Dawood M, Stegger L, Wubbeling F, Schafers M, Schober O, Schafers KP. List mode-driven cardiac and respiratory gating in PET. J Nucl Med. 2009;50(5):674-81. Epub 2009/04/18. doi: 10.2967/jnumed.108.059204. PubMed PMID: 19372491.

Desjardins B, Kazerooni EA. ECG-gated cardiac CT. AJR Am J Roentgenol. 2004;182(4):993-1010. Epub Mar. 25, 2004. doi: 10.2214/ajr.182.4.1820993. PubMed PMID: 15039178.

Fallavollita P. Is single-view fluoroscopy sufficient in guiding cardiac ablation procedures? Int J Biomed Imaging. 2010;2010:631264. doi: 10.1155/2010/631264. PubMed PMID: 20368770; PMCID: PMC2846336.

Jang S-J, Torabinia M, Dhrif H, Caprio A, Liu J, Wong SC, Mosadegh B. Development of a Hybrid Training Simulator for Structural Heart Disease Interventions. Advanced Intelligent Systems. 2020;2(12):2000109.

Koivumaki T, Nekolla SG, Furst S, Loher S, Vauhkonen M, Schwaiger M, Hakulinen MA. An integrated bioimpedance—ECG gating technique for respiratory and cardiac motion compensation in cardiac PET. Phys Med Biol. 2014;59(21):6373-85. Epub Oct. 9, 2014. doi: 10.1088/0031-9155/59/21/6373. PubMed PMID: 25295531.

Liu J, AF Aref SJ, Singh G, Caprio A, Moghadam AAA, Jang S-J, Wong SC, Min JK, Dunham S, Mosadegh B. An augmented reality system for image guidance of transcatheter procedures for structural heart disease. PLOS ONE. 2019;14(7):e0219174. doi: 10.1371/journal. pone.0219174.

Ronneberger O, Fischer P, Brox T, editors. U-net: Convolutional networks for biomedical image segmentation. International Conference on Medical image computing and computer-assisted intervention; 2015: Springer.

Sra J, Krum D, Choudhuri I, Belanger B, Palma M, Brodnick D, Rowe DB. Identifying the third dimension in 2D fluoroscopy to create 3D cardiac maps. JCI Insight. 2016;l(21):e90453. doi: 10.1172/jci.insight.90453. PubMed PMID: 28018976; PMCID: PMC5161213.

Torabinia, M., Caprio, A., Jang, S. J., Ma, T., Tran, H., Mekki, L., & Mosadegh, B. (2021). Deep learning-driven catheter tracking from bi-plane X-ray fluoroscopy of 3D printed heart phantoms. Mini-invasive Surgery, 5.

Adeoye O, Albright K, Carr B, et al., "Geographic access to acute stroke care in the United States." Stroke. 2014. 45: 3019-3024.

Bajo et al.. "Finding Lost Wrenches: Using Continuum Robots for Contact Detection and Estimation of Contact Location." 2010 IEEE International Conference on Robotics and Automation. Anchorage Convention District. May 3-8, 2010, Anchorage, Alaska, USA. pp. 3666-3673.

A. Bajo and N. Simaan, "Kinematics-Based Detection and Localization of Contacts Along Multisegment Continuum Robots," IEEE Transactions on Robotics, vol. 28, No. 2, pp. 291-302, Apr. 2012.

A. Bajo and N. Simaan, "Hybrid motion/force control of multibackbone continuum robots," The International Journal of Robotics Research. 35(4): 422-434. 2016.

J. Burgner-Kahrs, D. C. Rucker, and H. Choset, "Continuum Robots for Medical Applications—A Survey," IEEE Transactions on Robotics, 31(6): 1261-1280, Dec. 2015.

Campbell BCV, De Silva DA, Macleod MR, Coutts SB, Schwamm LH, Davis SM, and Donnan GA, "Ischaemic stroke" (2019) 5(70) Nature Reviews Disease Primers; pp. 1-6.

Comprehensive Stroke Center, The Joint Commission (Web Page) (2021); pp. 1-5.

J. J. Craig, Introduction to Robotics: Mechanics and Control. Pearson Prentice Hall Upper Saddle River, 2005, vol. 3. TOC.

Dasgupta et al., A Fully Convolutional Neural Network Based Structure Prediction Approach towards the Retival Vessel Segmentation, Nov. 16, 2016; pp. 1-4.

A. Degirmenci, P. M. Loschak, C. M. Tschabrunn, E. Anter, and R. D. Howe, "Compensation for Unconstrained Catheter Shaft Motion in Cardiac Catheters," in 2016 IEEE International Conference on Robotics and Automation (ICRA). May 2016, pp. 4436-4 442.

C. S. Dela Cruz et al. "Lung Cancer: Epidemiology, Etiology, and Prevention," Clinics in Chest Medicine, vol. 32, No. 4, pp. 605-644, 2011.

International Search Report and Written Opinion for International Application No. PCT/US2021/070726 dated Sep. 17, 2021.

B. Jones and I. Walker, "Kinematics for multisection continuum robots," IEEE Transactions on Robotics, vol. 22, No. 1, pp. 43-55, Feb. 2006.

B. Kim, J. Ha, F. C. Park, and P. E. Dupont, "Optimizing curvature sensor placement for fast, accurate shape sensing of continuum robots," in Proceedings—IEEE International Conference on Robotics and Automation. Institute of Electrical and Electronics Engineers Inc., 2014, pp. 5374-5379.

Chunwoo Kim, S. C. Ryu, and P. E. Dupont, "Real-time adaptive kinematic model estimation of concentric tube robots," in 2015 IEEE/RSJ International Conference on Intelligent Robots and Systems (IROS). IEEE, Sep. 2015, pp. 3214-3219.

A. Brij Koolwal, F. Barbagli, C. Carlson, and D. Liang, "An Ultrasound-based Localization Algorithm for Catheter Ablation Guidance in the Left Atrium," The International Journal of Robotics Research, vol. 29, No. 6, pp. 643-665, May 2010.

A. W. Mahoney, T. L. Bruns, P. J. Swaney, and R. J. Webster, "On the inseparable nature of sensor selection, sensor placement, and state estimation for continuum robots or where to put your sensors and how to use them," in 2016 IEEE International Conference on Robotics and Automation (ICRA). IEEE, May 2016, pp. 4472-4478.

Messenger JC, Ho KKL, Young CH et al. and NCDR Science and Quality Oversight Committee Data Quality Workgroup, "The National Cardiovascular Data Registry (NCDR) Data Quality Brief: The NCDR Data Quality Program in 2012." Journal of the American College of Cardiology. (2012); 60(16):1484-1488.

D. E. Ost, et al., "Diagnostic Yield and Complications of Bronchoscopy for Peripheral Lung Lesions. Results of the AQuIRE Registry," American Journal of Respiratory and Critical Care Medicine, vol. 193, No. 1, pp. 68-77, Jan. 2016.

J. Rosell, A. Perez, p. Cabras, and A. Rosell, "Motion planning for the Virtual Bronchoscopy," in 2012 IEEE International Conference on Robotics and Automation. IEEE, May 2012, pp. 2932-2937.

(56) References Cited

OTHER PUBLICATIONS

Saver JL, Goyal M, van der Lugt A, et al., "Time to treatment with endovascular thrombectomy and outcomes from ischemic stroke: a meta-analysis." JAMA (2016) 316(12):1279-1288.

Sganga, Jake, et al. "Autonomous Driving in the Lung using Deep Learning for Localization." Main Paper. Jul. 16, 2019; pp. 1-10.

Sganga, Jake, et al. "OffsetNet: Deep Learning for Localization in the Lung using Rendered Images." Stanford Education; Sep. 15, 2018. pp. 1-7.

Sganga, Jake, et al. "Orientation Estimation of a Continuum Manipulator in a Phantom Lung." Stanford Education; pp. 1-7.

O. K. Bruno Siciliano, Handbook of Robotics, 2008, Springer, vol. 53, No. 9. TOC.

S. Tully and H. Choset, "A Filtering Approach for Image-Guided Surgery with a Highly Articulated Surgical Snake Robot," IEEE Transactions on Biomedical Engineering, vol. 63, No. 2, pp. 392-402, Feb. 2016.

Venema E, Groot AE, Lingsma HF, et al., 'Effect of interhospital transfer on endovascular treatment for acute ischemic stroke'(2019); pp. 1-8.

Walker. "Continuous Backbone "Continuum" Robot Manipulators." ISRN Robotics. Hindawi Publishing Corporation. vol. 2013, Article ID 726506, 19 pages.

E. Wan and R. Van Der Merwe, "The unscented Kalman filter for nonlinear estimation," in Proceedings of the IEEE 2000 Adaptive Systems for Signal Processing, Communications, and Control Symposium (Cat. No. 00EX373). IEEE, pp. 153-158.

R. J. Webster and B. A. Jones, "Design and Kinematic Modeling of Constant Curvature Continuum Robots: A Review," The International Journal of Robotics Research, vol. 29, No. 13, pp. 1661-1683, Nov. 2010.

R. Xu, A. Yurkewich, and R. V. Patel, "Curvature, Torsion, and Force Sensing in Continuum Robots Using Helically Wrapped FBG Sensors," IEEE Robotics and Automation Letters, vol. 1, No. 2, pp. 1052-1059, Jul. 2016.

R. Xu, A. Yurkewich, and R. V. Patel, "Shape sensing for torsionally compliant concentric-tube robots," in SPIE BiOS, I. Gannot, Ed. International Society for Optics and Photonics, Mar. 2016, Proc. of SPIE vol. 9702, 97020V. 9 pages.

Yang et al., Deep Learning Segmentation of Major Vessels in X-Ray Coronary Angiography, Scientific Reports (2019); pp. 1-11.

M. Yip and D. Camarillo, "Model-Less Feedback Control of Continuum Manipulators in Constrained Environments," IEEE Transactions on Robotics, vol. 30, No. 4, pp. 880-889, Aug. 2014.

SYSTEMS AND METHODS FOR GUIDANCE OF INTRALUMINAL DEVICES WITHIN THE VASCULATURE

INCORPORATION BY REFERENCE TO ANY PRIORITY APPLICATIONS

This application is a continuation of prior application Ser. No. 17/389,973, filed Jul. 30, 2021, titled SYSTEMS AND METHODS FOR GUIDANCE OF INTRALUMINAL DEVICES WITHIN THE VASCULATURE, which is a continuation of prior application Ser. No. 17/350,999, filed Jun. 17, 2021, titled SYSTEMS AND METHODS FOR GUIDANCE OF INTRALUMINAL DEVICES WITHIN THE VASCULATURE, issued as U.S. Pat. No. 11,197,725, which claims the benefit to U.S. Provisional Application No. 63/041,538, filed Jun. 19, 2020, and U.S. Provisional Application No. 63/074,340, filed Sep. 3, 2020, and each of the foregoing cases are hereby incorporated herein by reference in their entirety. Any and all cases for which a foreign or domestic priority claim is identified in the Application Data Sheet as filed with the present application are hereby incorporated by reference under 37 CFR 1.57.

BACKGROUND

Field

The disclosure relates generally to vascular surgery and endovascular therapy, and more specifically, to autonomous endovascular navigation, localization and intervention.

Description

A large vessel occlusion (LVO) stroke occurs when a blood clot lodges in at least one of the internal carotid, proximal middle cerebral artery, proximal anterior cerebral artery, basilar artery or vertebral artery. Such a clot can partially or completely occlude downstream blood supply to brain tissue resulting in neuronal infarction and subsequent neurological impairment or death.

Traditionally, LVO stroke has been treated using intravenous fibrinolytic agents. However, improvement in neurological outcomes and risk mortality has recently been demonstrated in subjects who underwent mechanical thrombectomy (MT). Under certain conditions, a MT procedure conducted within a few hours (e.g., within six hours) of the onset of an LVO stroke has shown improved outcomes. From an economic perspective, for example, MT is likely to be cost-effective and/or even cost-dominant when conducting a lifetime analysis.

The benefits of MT are closely linked to the time it takes for the procedure to be performed. Accordingly, the faster the occlusion is treated, the better the outcome. For instance, under certain conditions, for every 9-minute delay to treatment, approximately 1 in 100 treated subjects has a worse disability outcome.

SUMMARY

Systems, methods, and devices for guiding an instrument within a vascular network of a patient are described herein. In some embodiments, the instrument comprises an endovascular or intraluminal instrument configured for navigation through the vascular network, such as a catheter (including a steerable or articulating catheter), guidewire, sheath, etc. In some embodiments, the instrument is coupled to a robotic medical system that is configured to manipulate the instrument (e.g., cause articulation, roll, insertion, retraction, etc.) during navigation. The systems, methods, and devices described herein can, in some embodiments, utilize medical imaging (e.g., X-ray or others) to facilitate navigation. For example, the instrument can be inserted into the anatomy, and a medical image of the anatomy can be captured. The instrument can be identified within the medical image using, for example, one or more computer vision techniques. A waypoint for the instrument can be identified, either by the system or from a user input (e.g., selection of a target waypoint relative to the medical image), and the instrument can be moved to the waypoint. This process can be iteratively repeated, in some embodiments, in a closed loop, to guide the instrument through the anatomy.

In a first aspect, a system for guiding an instrument within a vascular network of a patient is described. The system can include an electronic storage medium storing instructions configured to cause a processor to, for each of a plurality of steps in guiding the instrument through the vascular network: receive a medical image from a medical imaging device; identify, within the medical image, a distal tip of the instrument and a direction of the distal tip of the instrument; determine a current position and a current direction of the distal tip with respect to the medical image based on (a) the identified distal tip and the identified direction, (b) one or more past positions and past directions of the distal tip determined during one or more previously executed steps of the plurality of steps, and (c) one or more past trajectory commands generated during one or more previously executed steps of the plurality of steps; determine a waypoint for the distal tip of the instrument based at least in part on the determined current position and the current direction of the distal tip; and generate at least one current trajectory command based on the determined current position, the determined current direction, and the determined waypoint, the at least one current trajectory command for moving the instrument through the vascular network from the current position to the waypoint.

The system may include one or more of the following features, in any combination: (a) wherein determining the current position and current direction of the distal tip with respect to the medical image comprises determining the current position and current direction of the distal tip with respect to a two-dimensional imaging plane of the medical image; (b) wherein the processor is further configured to, for each step of the plurality of steps display the medical image, including an indication of the determined current position and the current direction of the distal tip, on a display device of a user device, and wherein determining the waypoint is further based on a user input received on an input device of the user device, the user input comprising a selection of a pixel or group of pixels on the displayed relative image; (c) wherein, for each step of the plurality of steps, the processor is further configured to determine the waypoint based on a pre-operatively determined pathway through the vascular network; (d) wherein, for each step of the plurality of steps, the processor is further configured to display, on the display device, the determined waypoint, and prior to generating the at least one trajectory command, receive a user confirmation or a user adjustment of the determined waypoint on the input device; (e) wherein the pre-operatively determined pathway through the vascular network is determined based on a pre-operative CT scan; (f) the processor is further configured to, for each step of the plurality of steps, provide the at least one current trajectory command to a robotic medical system configured to move the instrument according to the at least one current trajectory command, whereupon the robotic medical system moves the instrument; (g) wherein the processor is further configured to, for each of the plurality of steps receive, from a force sensor associated with the instrument, an insertion force measure associated with the execution of the at least one current trajectory command by the robotic medical system, and cause the robotic medical system to stop movement of the instrument or retract the instrument when the insertion force measure exceeds a predetermined insertion force limit; (h) wherein the processor is further configured to, for each of the plurality of steps, determine whether to inject a contrast material into the vascular network based on a time elapsed since a previous injection of contrast material, a distanced moved by the instrument since a previous injection of contrast material, and/or the determined current position and direction of the distal tip; (i) wherein the processor is further configured to, upon a determination to inject the contrast material, provide a command to a robotic medical system configured to move the instrument, whereupon the robotic medical system injects the contrast material according to the command; (j) wherein the medical image is obtained non-invasively; (k) wherein the processor is further configured to determine whether the patient is a candidate for the endovascular procedures based on analysis of a pre-operative CT scan; (l) wherein the analysis of the pre-operative CT scan is configured to identify one or more of the following coarctation of the aorta, concomitant aortic dissection, ipsilateral carotid stenosis, a presence of an unstable carotid plaque, aortoiliac occlusive disease, right arch/left heart and bilateral femoral artery stenoses precluding vascular access, severe vascular tortuosity, anatomical variants of the aortic arch anatomy, severe intramural calcification, for an aberrant right subclavian artery, and/or a supreme intercostal right vertebral artery origin; (m) wherein the processor is configured to identify, within the medical image, the distal tip and the direction of the distal tip based on one or more computer vision models; (n) wherein the one or more computer vision models comprise: semantic segmentation of the vascular network and instrument, classifications on the distal tip position and/or direction, regressions on the distal tip position and/or direction, and/or providing bounding boxes over the vascular network and/or the distal tip; (o) wherein generating the at least one current trajectory is further based on one or more of an inverse kinematics motion control algorithm and a Jacobian motion control algorithm; (p) wherein the processor is further configured to display, on a display device, the at least one current trajectory command, whereupon an operator viewing the display device manually or robotically executes the at least one trajectory command; (q) wherein the processor is configured to execute the plurality of steps as a closed loop; (r) wherein the instrument comprises one or more of an endovascular catheter or an endovascular guidewire; (s) wherein the medical imaging device comprises an X-ray machine; and/or other features as described throughout this application In another aspect, a system for guiding an instrument within a vascular network of a patient from an insertion site to a target site during an endovascular procedure is described that comprises an electronic storage medium storing instructions configured to cause a processor to, for each of a plurality of steps in guiding the instrument through the vascular network to the target site: receive a medical image from medical imaging device, wherein the medical image is obtained non-invasively; identify, within the medical image, a distal tip of the instrument and a direction of the distal tip of the instrument; determine a current position and a current direction of the distal tip of the instrument with respect to a two-dimensional imaging plane of the medical image based on (a) the identified distal tip and the identified direction of the distal tip, (b) one or more past positions and past directions of the distal tip determined during one or more previously executed steps of the plurality of steps, and (c) one or more past trajectory commands generated during one or more previously executed steps of the plurality of steps; display the medical image, including an indication of the determined current position and the current direction of the distal tip, on a display device of a user device; receive, on an input device of the user device, a selection of a navigation waypoint for movement of the distal tip of the instrument, wherein the selection comprises a pixel or group of pixels on the displayed medical image; generate at least one current trajectory command based on the determined current position and the current direction, the at least one current trajectory command for moving the instrument within the vascular network toward the navigation waypoint; and provide the at least one current trajectory command to a robotic medical system configured to move the instrument according to the at least one current trajectory command.

The system may include one or more of the following features, in any combination: (a) wherein the user device is remotely located relative to the patient, the instrument, and the robotic medical system; (b) wherein the user device communicates with the system over a public computer network; (c) wherein the user device comprises a personal computer, a laptop, a tablet, or a smartphone; (d) wherein the processor is further configured to receive or determine a pathway from the insertion site to the target site, and, for each of the plurality of steps in guiding the instrument along the pathway to the target site, determine a suggested navigation waypoint for movement of the distal tip of the instrument, display the suggested navigation waypoint on the displayed medical image, and wherein receiving, on the input device of the user device, the selection of the navigation waypoint for movement of the distal tip of the instrument comprises receiving a confirmation of the suggested navigation waypoint; (e) wherein the endovascular procedure comprises a mechanical thrombectomy for large vessel occlusion stroke treatment; and/or other features described throughout this application.

In another aspect, a system for guiding an instrument within a vascular network of a patient includes: an instrument configured for navigation through the vascular network of the patient; a robotic medical system coupled to the instrument and configured to move the instrument through the vascular network; and an electronic storage medium storing instructions configured to cause a processor to, for each of a plurality of steps in guiding the instrument through the vascular network: receive a medical image from a medical imaging device; identify, within the medical image, a distal tip of the instrument and a direction of the distal tip of the instrument; determine a current position and a current direction of the distal tip with respect to the medical image based on (a) the identified distal tip and the identified direction, (b) one or more past positions and past directions of the distal tip determined during one or more previously executed steps of the plurality of steps, and (c) one or more past trajectory commands generated during one or more previously executed steps of the plurality of steps; determine a waypoint for the distal tip of the instrument based at least in part on the determined current position and the current direction of the distal tip; generate at least one current trajectory command based on the determined current position and direction and the determined waypoint, the at least one current trajectory command for moving the intraluminal medical instrument through the vascular network from the current position to the waypoint; and provide the at least one current trajectory command to a robotic medical system configured to move the instrument according to the at least one current trajectory command.

The system may include one or more of the following features in any combination: (a) wherein the processor is further configured to, for each step of the plurality of steps, display the medical image, including an indication of the determined current position and the current direction of the distal tip, on a display device of a user device, and wherein determining the waypoint is further based on a user input received on an input device of the user device, the user input comprising a selection of a pixel or group of pixels on the displayed relative image; (b) wherein, for each step of the plurality of steps, the processor is further configured to determine the waypoint based on a pre-operatively determined pathway through the vascular network; (c) wherein determining the current position and current direction of the distal tip with respect to the medical image comprises determining the current position and current direction of the distal tip with respect to a two-dimensional imaging plane of the medical image; and/or other features as described throughout this application.

According to some embodiments, a method of guiding an intraluminal component of a robotic assembly within an anatomical intravascular network of a subject to a targeted anatomical location comprises obtaining a plurality of images of the subject's anatomy to determine a location of the intraluminal component relative to the anatomical intraluminal network; determining, using a guidance system, a predetermined pathway for guiding the intraluminal component from a first point to a second point within the intraluminal network, wherein determining the predetermined pathway comprises processing data related to the plurality of images; and automatically advancing the intraluminal component through the anatomical intraluminal network of the subject to the targeted anatomical location along the predetermined pathway, wherein the system is configured to at least temporarily cease advancement of the intraluminal component if at least one triggering criterion occurs.

According to some embodiments, the systems, methods, and devices described herein are configured to treat ischemic stroke. In some arrangements, the anatomical intraluminal network comprises a vasculature of the subject. In one embodiment, the targeted anatomical location comprises a cerebral artery.

According to some embodiments, the intraluminal component or instrument comprises one or more of a catheter, a sheath, a wire, or the like. In some embodiments, the systems, methods, and devices can further comprise processing data relating to at least one other factor. In some embodiments, the at least one other factor comprises data obtained from other subjects who have undergone a similar procedure and/or other historical data that can be used to develop and/or train an algorithm. In some embodiments, the data relates to anatomical pathway information for reaching the targeted anatomical location.

According to some embodiments, the at least one triggering criterion comprises a real-time force along the intraluminal component that exceeds a threshold value. In some embodiments, the at least one triggering criterion comprises a determination that a distal end of the intraluminal component is not oriented in a direction aligned with the predetermined pathway. In some embodiments, the at least one triggering criterion comprises the appearance (e.g., the two-dimensional or three-dimensional pose or shape) of the instrument or intraluminal component. For example, in some embodiments, bowing of the body of the instrument or intraluminal component or the irregular, scrambled, or bent appearance of the instrument or intraluminal component or the distal end thereof can be a triggering criterion.

According to some embodiments, the systems described herein comprise computer-readable storage mediums that determine the predetermined pathway. In some embodiments, the system is configured to operatively couple to a robotic assembly.

According to some embodiments, the systems, methods, and devices further comprise performing a treatment procedure once the intraluminal component has reached the targeted anatomical location. In some embodiments, the treatment procedure comprises at least partially removing a clot or other obstruction or occlusion from the targeted anatomical location. In some embodiments, the clot or other obstruction is at least partially removed using suction thrombolysis or stent retrieval.

According to some embodiments, obtaining the plurality of images comprises using an imaging device. In some embodiments, the imaging device comprises an external X-ray device. In other embodiments, the imaging device comprises an external X-ray and contrast opacified blood vessels.

According to some embodiments, a system is configured to treat ischemic stroke by autonomously steering a catheter to an offending clot and retrieving it. In some arrangements, the system comprises a processor configured to, upon execution of specific program instructions stored on a computer-readable storage medium, provide guidance for moving a robotic device through the vasculature of the subject to reach the clot.

In general, prior catheter control techniques relied largely upon information provided by sensing modalities localized at the tip of the instrument. In some embodiments, the methods, systems and devices described herein, are not limited in the same way. Rather, in some embodiments, the methods, systems, and devices can utilize computer vision algorithms to detect the catheter within a medical image (e.g., an X-ray) and determine the position (e.g., the two-dimensional (x, y) position) and heading angle of any point along the catheter body. This information can inform a motion planning algorithm about how the catheter might behave in response to various movement or trajectory commands (e.g., actuating motors of a robotic medical system or manually driving the instrument). For example, a point some distance along the catheter body or a collection of points along the catheter body may be used to estimate the direction in which the catheter may move when inserted. This information can be used to select the motor inputs most likely to advance the catheter to its target location. With this information, a kinematic model may not be needed to calculate the estimated position and heading of the catheter's articulating section. Instead, it is directly observed (e.g., within the image). These and other features are described in greater detail throughout this application.

BRIEF DESCRIPTION OF THE DRAWINGS

These and other features, aspects and advantages of the present application are described with reference to drawings of certain embodiments, which are intended to illustrate, but not to limit, the present disclosure. It is to be understood that the attached drawings are for the purpose of illustrating concepts disclosed in the present application and may not be to scale.

FIG. 20 illustrates an example output of an IP address command according to an embodiment.

FIG. 21 illustrates an example output of a traceroute command according to an embodiment.

Figure 1:
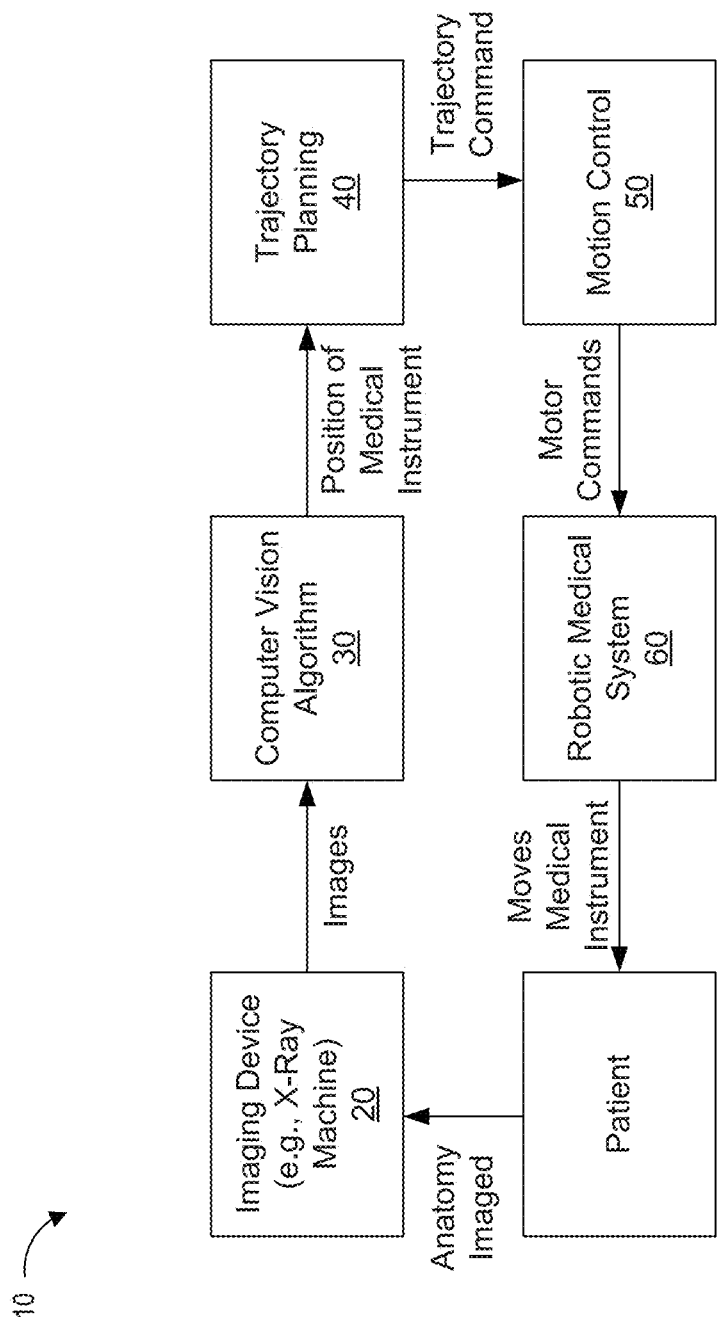
FIG. 1 schematically illustrates different modules of a system for locating and removing a clot or other obstructive member from a body lumen of a subject according to one embodiment.

The figures are drawn for ease of explanation of the basic teachings of the present disclosure only; the extensions of the figures with respect to number, position, relationship, and dimensions of the parts to form the preferred embodiment will be explained or will be within the skill of the art after the following teachings of the present disclosure have been read and understood. Further, the exact dimensions and dimensional proportions to conform to specific force, weight, strength, and similar requirements will likewise be within the skill of the art after the following teachings of the present disclosures have been read and understood.

DETAILED DESCRIPTION

The systems disclosed herein may be configured to safely and predictably direct a robotically-controlled device through the vasculature (or other intraluminal system) of a subject to access a clot or other complete or partial occlusion. The various inventions described herein can provide one or more benefits to the subject being treated and the treatment procedure more generally, including, for example and without limitation, enabling the performance of time critical vascular intervention in certain situations and locations (e.g., instances where a trained interventionist is not available), making more precise intervention decisions, providing inbuilt safety mechanisms (e.g., including force feedback), providing assessment of the appearance of instrument tips to reduce or minimize the risk of vascular complications, assessment of the degree of success of the intervention, providing a more reliable system and method for advancing an intraluminal device of a robotic assembly to a target anatomical location, providing a safer approach to automatic advancement of an intraluminal device within a subject's anatomy, providing a more sophisticated strategy for determining a desired or preferred intraluminal pathway for reaching a targeted anatomical location and/or the like.

The various technologies disclosed herein can be used for the treatment of various diseases and other conditions where a robotic device is advanced through an intraluminal (e.g., intravascular) network of a subject to reach the site of intravascular pathology (e.g., thrombosis, embolus, occlusion, aneurysm, rupture, bleeding, dissection, etc.). For example, as discussed in greater detail herein, the various embodiments disclosed in this application can be used to treat stroke (e.g., LVO stroke). In such configurations, for example, the system may be configured to autonomously or semi-autonomously advance a robotic device through the vasculature of the subject to reach an offending clot. In some embodiments, the vascular robotic device is configured to at least partially remove the clot (e.g., using mechanical thrombectomy, using dissolution techniques, etc.), as desired or required.

Although this application is primarily focused on the treatment of ischemic stroke and the removal of clots, the various systems and methods disclosed herein can be used in a variety of other applications where robotic systems are used to guide catheters and/or other devices through an intraluminal anatomical network of a subject. For example, the various systems, devices, and/or methods discussed herein can be used in arterial applications (e.g., arterial angioplasty, arterial stenting, arterial thrombectomy, arterial embolization, insertion of flow diverters for treatment of an aneurysm, treatment of arteriovenous malformation, etc.), venous applications (e.g., venous stents, venous thrombectomy, including thrombectomy and suction thrombolysis for pulmonary embolism, etc.), aortic applications (e.g., endovascular abdominal aortic stents, endovascular thoracic aortic stents, etc.), cardiac applications (e.g., transcatheter valve replacement (aortic, mitral, tricuspid, pulmonary), repair of atrial and ventricular septal defects, insertion of pacemaker/defibrillator, etc.), and other miscellaneous applications (e.g., administration of directed arterial chemotherapy, insertion of neuromodulation devices, insertion of veno-cacal filters, etc.).

General

As schematically illustrated in FIG. 1, according to some embodiments, a system 10 can include several modules or components. The system 10 can be provided with all such modules or components. Alternatively, the system 10 can include only some of the modules or components. In such arrangements, however, the various modules or components included in the system 10 can be advantageously adapted to function with separate modules or components which are not necessarily included in the system 10. In other words, a system 10 can be configured to operatively couple to one or more modules or components provided by another manufacturer or supplier.

With continued reference to FIG. 1, the system 10 can include (or can be configured to operatively couple to) an X-ray device or another imaging device or system 20. The system 10 can further comprise a vision processing component 30 that is configured to receive X-ray or other imaging data from the imaging device 20.

Figure 2:
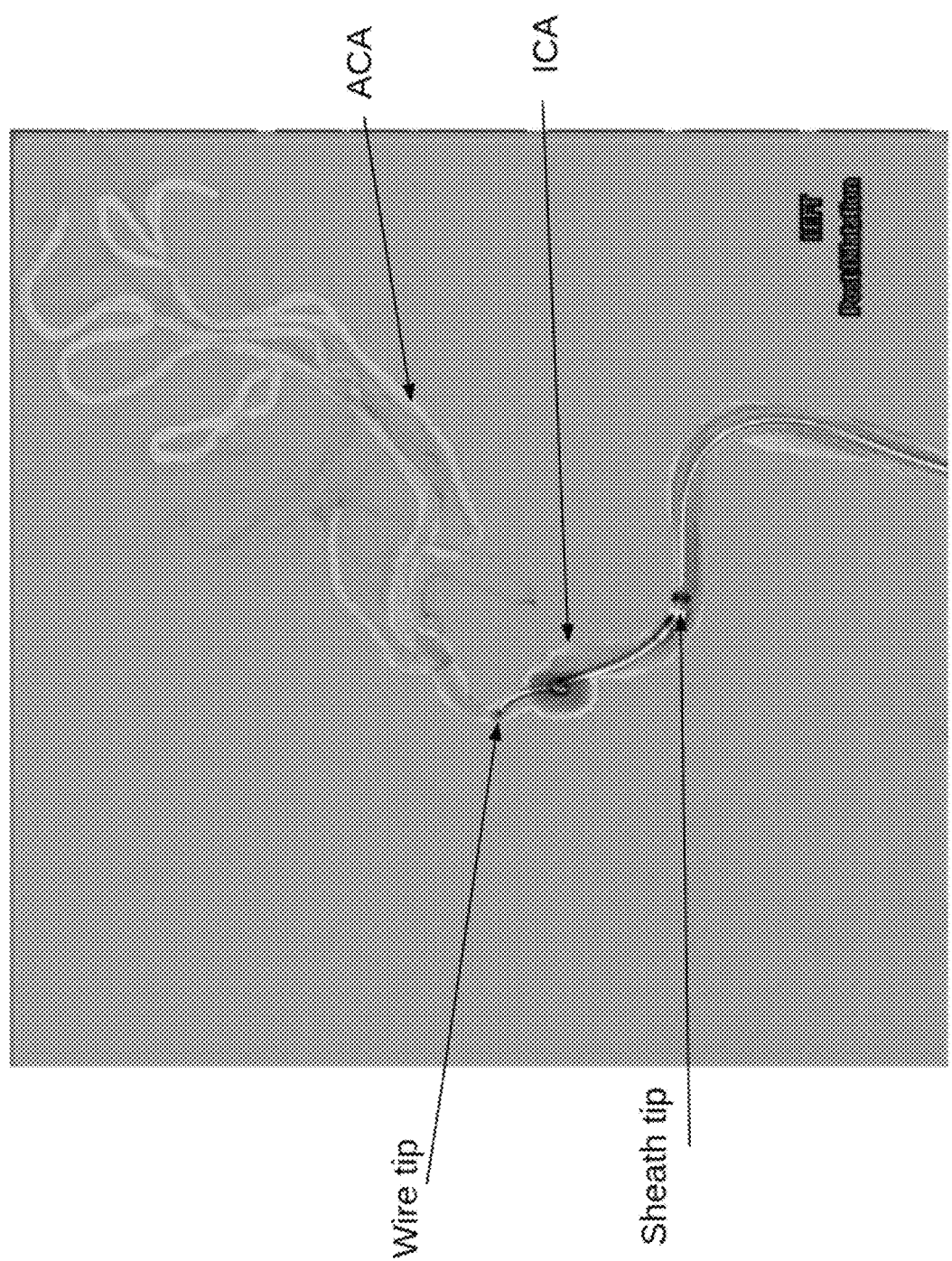
FIG. 2 illustrates one embodiment of an output of imaging showing a catheter being advanced through the vasculature of the subject.

According to some embodiments, the imaging device 20 is configured to acquire real-time images of the subject prior to and/or during the execution of a procedure (e.g., mechanical thrombectomy). In some embodiments, the imaging device 20 is configured to acquire real-time images of the subject while navigating to the site of the intervention. In some embodiments, the imaging device 20 comprises an external X-ray device. However, in other arrangements, the imaging device 20 can include any other type of device, such as, e.g., intravascular ultrasound and/or any other intravascular imaging device. One embodiment of an output or other computer representation derived at least partially from the output of the imaging device 20 showing a catheter being advanced through the vasculature of the subject is illustrated in FIG. 2.

In some arrangements, the imaging device 20 is included together with other components of the system 10 in a single or unitary component or device. However, in other arrangements, the imaging device 20 is a separate device or component (e.g., an off-the-shelf device), and the overall system 10 is configured to operatively couple to such a separate device 20. Such operative coupling between various components and/or devices included in the system can be accomplished using one or more wired and/or wireless connection platforms.

According to some embodiments, at specific intervals (e.g., a regular interval, an interval triggered by the occurrence of some event, etc.), an image (e.g., x-ray) of the subject is acquired by the imaging device 20. As schematically depicted in FIG. 1, such images can be provided to a vision processing component 30. The vision processing component 30 can be operatively coupled to a processor (e.g., within a computer or other computing device). Such a processor can be configured to, upon execution of specific program instructions stored on a computer-readable storage medium, provide guidance for moving a robotic device through the anatomy of a subject (e.g., through the vasculature of the subject to reach the clot for the treatment of ischemic stroke).

The frequency at which images are acquired by the imaging device 20 and the frequency at which the imaging device 20 delivers images to the vision processing component 30 can vary, for example, based on a desired or required protocol. In some embodiments, these two frequencies are identical (or substantially identical) such that images that are obtained by the imaging device 20 are subsequently (e.g., immediately or nearly immediately) provided to the vision processing component 30. However, in other embodiments, the two frequencies can be different from one another. For instance, in one arrangement, the images acquired by the X-ray device or other imaging device 20 can be provided to the vision processing component 30 in batches (e.g., 2, 3, 4, 5, more than 5, etc.) at one time. In some embodiments, bursts of images can be taken (e.g., at 20 to 30 Hz), and those bursts may be separated by a time period (e.g., a configurable time period), for example, a time period of several seconds (0.05 to 0.5 Hz for bursts).

According to some embodiments, the frequency at which images are acquired by the imaging device 20 and/or the frequency at which the imaging device 20 delivers images to the vision processing component 30 can be 0.1 seconds to 10 seconds (e.g., 0.1-0.2, 0.2-0.3, 0.3-0.4, 0.4-0.5, 0.5-1, 1-2, 2-3, 3-4, 4-5, 5-6, 6-7, 7-8, 8-9, 9-10 seconds, values in between the foregoing ranges, etc.). In other embodiments, the frequency at which images are acquired by the imaging device 20 and/or the frequency at which the imaging device 20 delivers images to the vision processing component 30 can be less than 0.1 seconds or greater than 10 seconds, as desired or required. In other embodiments, the frequency at which images are acquired by the imaging device 20 and/or the frequency at which the imaging device 20 delivers images to the vision processing component 30 depends on the occurrence of one or more events (e.g., the catheter has been advanced or otherwise moved within the targeted intraluminal device by a particular distance, a user of the system can select when images are acquired and processed, etc.).

With further attention to FIG. 1, a trajectory planning or guidance module or component 40 can be configured to generate a desired or preferred pathway through a targeted intraluminal network of a subject (e.g., the subject's vasculature). Such a desired or preferred pathway can be based, at least in part, on one or more of the following factors: imaging provided by the imaging device 20; imaging from one or more preoperative scans, such as CT, MRI, or x-ray images; data regarding the specific procedure to be performed (e.g., MT or other clot treatment); data and resulting modeling generated from prior procedures (e.g., prior similar procedures); information regarding the subject (e.g., gender, age, height, weight, health condition, disease assessment, etc.); the output from computer vision algorithms (device 30) and/or any other factor.

In some embodiments, the X-ray and/or other imaging data provided to the vision processing component 30 can include images related to the subject's anatomy (e.g., depicting the intravascular or other intraluminal network of the subject), images related to the instrumentation and/or other devices that will be advanced through a subject's targeted intraluminal network, and/or the like.

The vision processing component 30 can comprise an algorithm or program instructions stored on a computer-readable storage medium. In some embodiments, such a processing component 30 is incorporated into a larger computing system that also includes a processor and/or other components (e.g., other modules and/or processors, memory, input/output devices, power modules, etc.). For example, as discussed in greater detail below, a single computing device can include the vision processing component 30, the trajectory or guidance planning module 40, and a motion control module 50. In other embodiments, a larger computing system includes only one, two, or less than all of the various modules, as desired or required. Therefore, in some arrangements, two or more separate computing devices (or devices comprising computing devices or processors) are used to accommodate all of the desired or required modules and/or other components of the system 10.

As noted above, in some embodiments, the vision processing component 30 can be configured to process the various images provided to it and determine the location and/or configuration (e.g., pose, shape, and/or orientation) of any instrumentation and/or other intraluminal tools being used for a particular procedure relative to the subject's targeted intraluminal network. In some embodiments, the location of the instrumentation and/or other tools used in a particular procedure are provided to the trajectory or guidance planning module or component 40. Such a module or component 40 can include an algorithm or program instructions stored on a computer-readable storage medium and can be configured to determine and/or recommend one or more pathways through the corresponding intraluminal network of a subject (e.g., through the subject's vasculature from the point of entry, such as a femoral artery, to the targeted location of a clot in the brain) based, at least in part, on images related to the subject's specific anatomy, the surgical tools being used to perform the specific procedure, previously collected data (e.g., prior treatment data), and/or one or more other factors or considerations.

With continued attention to the schematic depicted in FIG. 1, the system 10 can include a motion control module or component 50 that is configured to receive a set of commands from the trajectory or guidance planning module or component 40. In some embodiments, such a set of commands comprises specific instructions to a motion control module or component 50 that is configured to provide the necessary control setting to operate a robotic system 60. For example, the motion control module or component 50 can be configured to directly or indirectly communicate with a robotic system 60 that is being used to execute a desired protocol. In some embodiments, the motion control module or component 50 is adapted to cooperate with one of several robotic systems 60 that can be used in conjunction with the system 10. In other arrangements, the motion control module or component can be customized in order to properly provide instructions and operatively couple to a robotic system 60.

As noted above, one or more of the system 10 components or modules can be incorporated into a single device or system, as desired or required. In other embodiments, components or modules can be included into two or more separate devices.

The motion control module 50 can be configured to determine how to move the robot's motors and/or other components to achieve the desired trajectory command. The robotic system 60 can be adapted to execute the command provided to it (e.g., by the motion control module 50) and modify the necessary mechanical components of the robotic system 60 to move the surgical tools within the anatomy.

Contrast agent and/or other image-enhancing technologies can be incorporated into the various devices, systems, and/or methods disclosed herein to facilitate execution of a particular procedure. For example, contrast agent can be used during execution of a treatment procedure to enhance visualization of blood flow through a targeted vasculature of a subject. In other words, the contrast agent can render the targeted vessels visible (or improve the visibility of the targeted vessels) under X-ray (and/or other imaging technologies). In some embodiments, the instruments and/or other devices are directed through these vessels (e.g., by the robotic system 60).

According to some embodiments, the systems and methods disclosed herein are configured to release contrast agent within the targeted intraluminal network (e.g., vasculature) of the subject when X-ray and/or imaging is acquired (e.g., by imaging device 20 or the vision processing component or module 30). For example, according to some arrangements, a typical flow would be to inject contrast and then record a burst of X-ray images to observe the contrast flow through the vessels of the subject.

For any of the embodiments disclosed herein, contrast agent and/or other image-enhancing technologies can be used to accomplish one or more of the following: to confirm the presence of intravascular pathology (e.g., filling defect/stroke, aneurysm, dissection, etc.), confirm the vascular anatomy of the subject, localize instruments in relation to the subject's anatomy, assess for possible complications (by way of example, in some embodiments, extravascular contrast extravasation can be suggestive or otherwise indicative of vessel perforation), and/or the like.

Contrast agent can be configured to be injected automatically (e.g., according to some frequency, according to an algorithmically generated trigger, etc.) and/or manually (e.g., at the direction of a practitioner or other user), as desired or required, for any of the systems disclosed herein. By way of example, a predetermined volume of contrast agent can be released into a targeted vasculature of a subject prior to obtaining imaging using an X-ray or other imaging device 20. The algorithmic trigger may be based on the output from the device 30, the device 40, and/or the device 50, e.g., when the trajectory is approaching a bifurcation or when the statistical confidence in the anatomical features drops below a set threshold.

The various embodiments disclosed herein can provide one or more benefits and advantages to a robotically-controlled intraluminal procedure. For example, as discussed in greater detail below, the present application discloses a clinically predictable, reliable, and safe way of using preoperative screening to determine whether or not a subject is eligible to undergo a desired or required procedure. In some embodiments, the methods and systems described herein may include the use of preoperative screening, which can include obtaining a computerized tomography (CT) scan and/or other screening technologies that help obtain a clear view of the anatomical environment before beginning a procedure.

According to some embodiments, a predictable screening procedure that takes the specific anatomical landscape of a subject into consideration can help make the actual treatment procedure tractable or more predictable. This can provide predictable and simplified guidance to a practitioner that a desired treatment protocol can proceed.

According to some embodiments, a catheter and/or other instrument or device that is guided within an intraluminal network of a subject's anatomy (for example, as controlled by the device 60 of FIG. 1) can include one or more sensors. For example, such a device can comprise a force or pressure sensor that is designed and otherwise adapted to detect a force to which the portion of the catheter or other device that includes the sensor is subjected.

As a result of using force or pressure sensors on the catheters and/or other intraluminal devices that will be advanced through the subject, the system can ensure that unintentional, potentially misguided, and/or dangerous maneuvers being performed by a robotic system are prevented. In some embodiments, once the force detected by such a sensor exceeds a particular high threshold value, the system is configured to direct the robotic system to cease, retract, and/or take other appropriate steps. For example, the force sensor data can be provided to the trajectory or guidance planning module or component 40, the motion control module or component 50, the device 60, and/or any other component or module of the system 10 to ensure that the force generated by attempting to advance the corresponding catheter or other device through the subject does not reach an undesirable value. In some embodiments, the acceptable force threshold may be modified based on the stage of the procedure and/or other information related to the subject.

According to some embodiments, the catheters, instruments and/or tools included as part of the robotic system include one or more force or pressure sensors. In such circumstances, the sensors are designed and otherwise adapted to communicate (e.g., wirelessly) the force or pressure data in real time to the trajectory or guidance planning module or component 40, the motion control module or component 50 and/or any other component or module of the system 10.

In some embodiments, the threshold force or pressure that triggers a change in the procedure (e.g., to prevent harm or other damage to the subject or the system) can depend on the specific procedure being performed. The system can be configured to permit a practitioner or other user to select threshold force value. Such customization can ensure that a practitioner accounts for additional subject and/or procedure specific considerations in connection with a robotic procedure. In other embodiments, the threshold force or pressure can be determined by the system 10, for example, by the trajectory planning component 40.

In other embodiments, the system can include a force or pressure sensor that is configured to be removably attached to one or more portions of a catheter or other device that will be advanced through a subject. For example, such a removable sensor can be configured to secure to or near a distal end of a catheter. Such removable/attachable sensors can be reusable or disposable, as desired or required.

According to some arrangements, two or more computer vision models can be used for a particular system. Such redundancy can further ensure that the imaging data obtained and processed by the system are accurate. This can result in safer and more predictable treatment procedures.

In some embodiments, the system is configured to automatically commence the required or desired treatment steps (e.g., removal of a clot) once the catheter and/or other devices that are advanced through the subject have attained their targeted location. In other configurations, however, such treatment steps are manually initiated by a practitioner or other user, as desired or required by a particular application or use.

With respect to certain treatment protocols, the system can be configured to use one or more models (e.g., vision models) to analyze the state of the treatment steps that are or were performed by the robotic system to ensure efficacy, safety, and/or other goals. For instance, in some embodiments involving treatment of ischemic stroke, a computer vision model can be used to confirm the degree of reperfusion. This can help the practitioner determine if the procedure can be terminated or if additional action is needed. Such confirmation can be configured to occur automatically or manually (e.g., via the input of a practitioner).

For any of the embodiments disclosed herein, the system can, in some instances, be adapted to permit or require human operator involvement or interaction (e.g., confirmation, oversight, etc.) before certain further steps are taken. For instance, as a catheter and/or other instrument is being advanced within the vasculature or other intraluminal network of a subject, the system can be configured to require the practitioner to approve of one or more subsequent steps or actions before the procedure can resume.

According to some embodiments, time lapse images obtained by an X-ray or other imaging device 20 and transferred to one or more other modules or components of the system 10 can be used to create a single, simplified view (for example, a view that can be displayed to a practitioner, operator, or other user on a graphical user interface). Such a view can provide additional information to the practitioner and further assist him or her with oversight during the execution of a robotic procedure. In some embodiments, such time-lapse images can involve color, contrasting, patterning, and/or the like to view changes over time, as desired or required.

Figure 3:
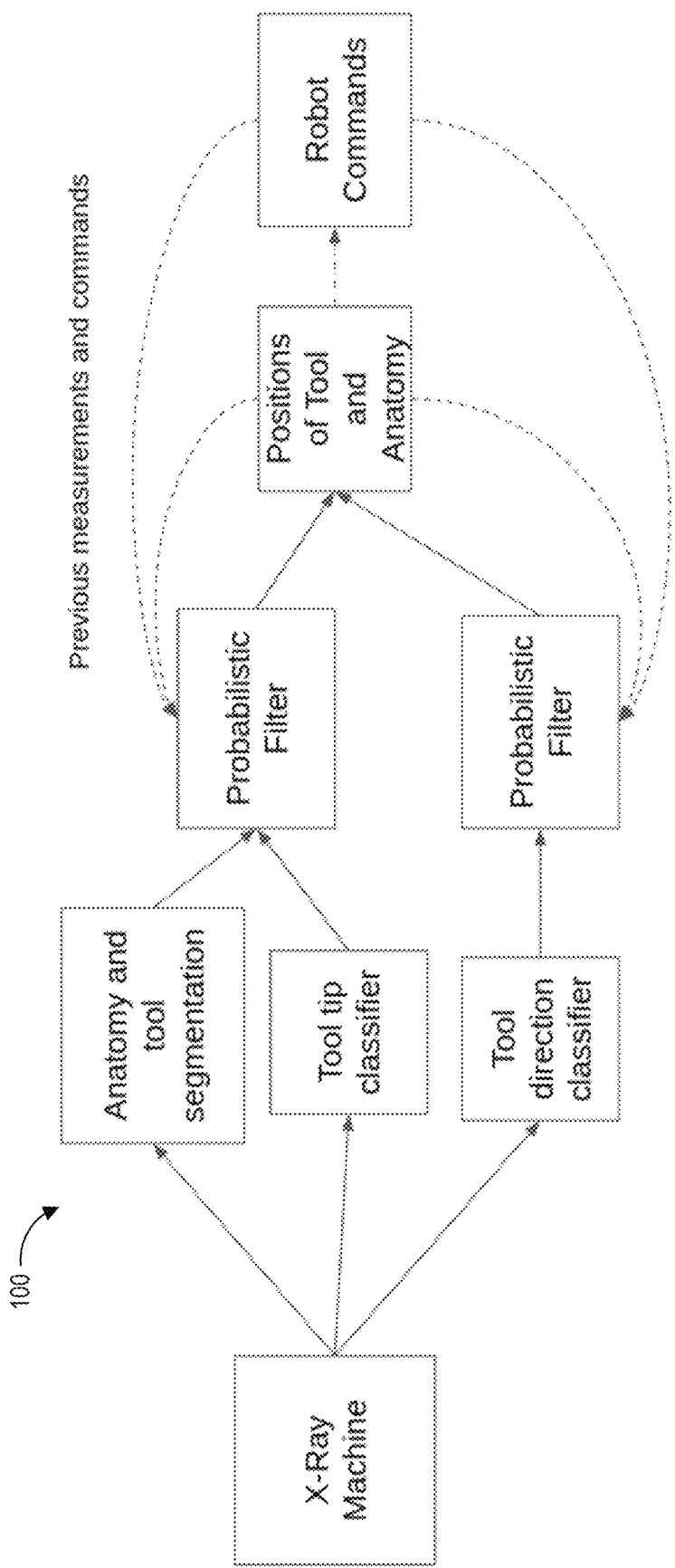
FIG. 3 illustrates one embodiment of a flowchart depicting various steps that the system can take to accomplish refined approximations during a procedure.

According to some embodiments, tools (e.g., predictive modeling, other data processing, etc.) can be used to estimate or update estimates of anatomical locations over time. As a result, a roadmap or pathway for a catheter or other device that will be advanced through the subject that is recommended and guided by the system 10 can be refined (e.g., fine-tuned) with additional imaging, data, and/or other information. Such refinements can be used to benchmark any deviations from the expected guidance of a catheter or other device through the anatomy of a subject. One example flowchart 100 illustrating various steps that the system can take to accomplish refined approximations during a procedure is provided in FIG. 3.

In some configurations, the system can be adapted to display or otherwise provide one or more outputs (e.g., visual, audible, haptic, etc.) to the practitioner during the execution of a procedure. For example, a description of the processing and recommended next steps being made by the system (e.g., in real time) can be provided to a user. In some embodiments, the system can provide one or more of the following data and/or other information to the practitioner: the location of the catheter and/or other instruments or devices being advanced through the subject, where such devices will move next (e.g., specific branch, direction (e.g., "turn right or left," "rotate," "move forward," "retract,"

Figure 4:
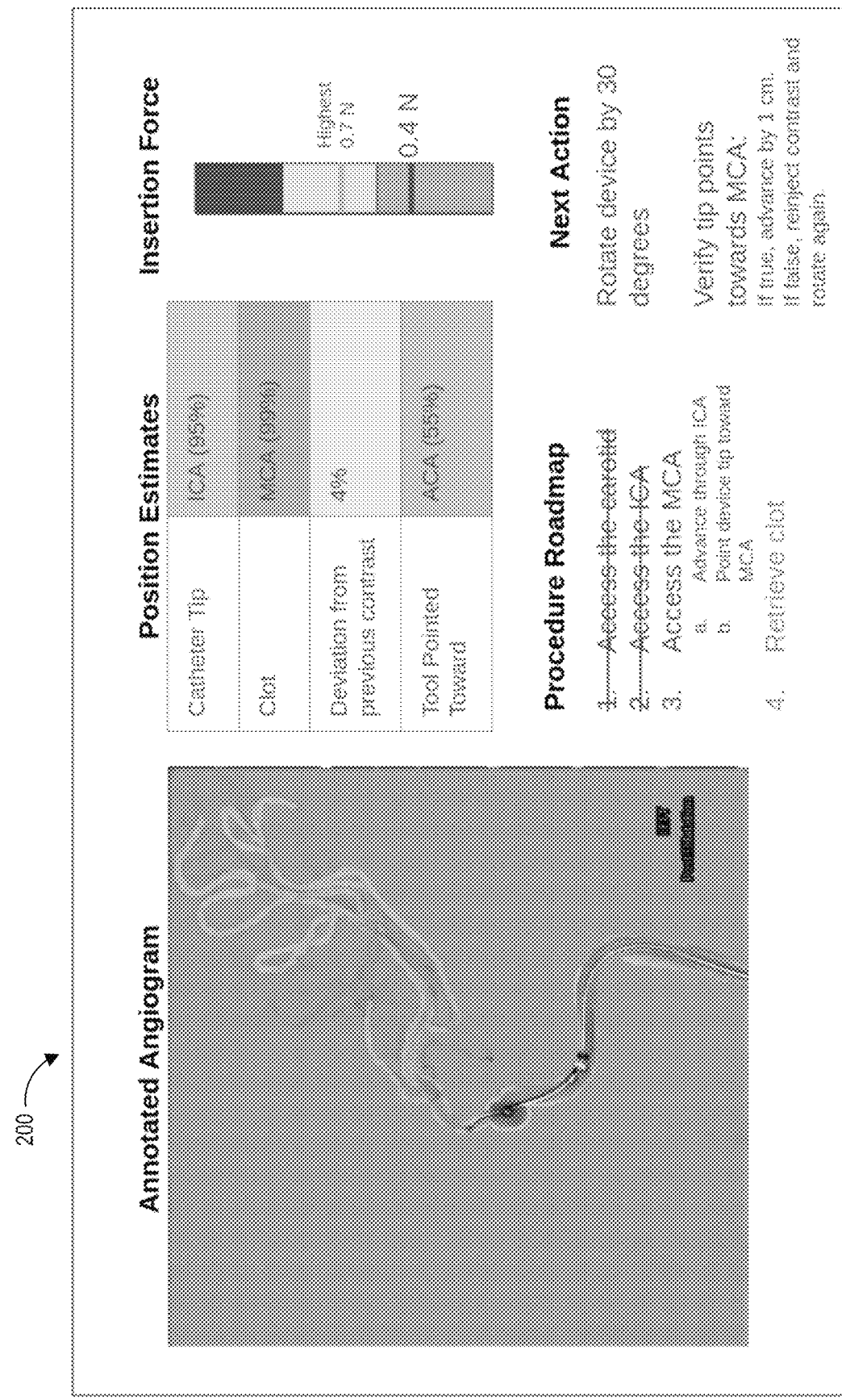
FIG. 4 illustrates one embodiment of a display output configured to be provided by a system disclosed herein.

"commence clot removal or other treatment step," etc.), what clinical step is being performed, what clinical steps have been performed, what clinical steps remain to be performed, pressure or force measurement of any sensors positioned on or along any intraluminal devices, and/or the like. One example of such a display output 200 is illustrated in FIG. 4.

In order to provide the information to a practitioner or other user, the system can include one or more outputs (e.g., a display, touchscreen, etc.). In some arrangements, such an output can be incorporated into the system. In alternative embodiments, such an output is separate from the system; however, it can be advantageously configured to be operatively coupled to the system (e.g., via one or more wired or wireless connections), as desired or required.

Pre-Procedural Eligibility and Assessment

For any of the embodiments disclosed herein, the systems and/or corresponding methods can include prescreening measures to verify whether the desired treatment protocol can or should be performed on a specific subject (e.g., to verify the safety and/or efficacy of such a desired treatment protocol).

By way of example, prescreening of a subject to ensure that a mechanical thrombectomy procedure can be safely performed using the technologies disclosed herein can comprise ensuring that the subject does not have or exhibit symptoms of one or more of the following: coarctation of the aorta, concomitant aortic dissection, ipsilateral carotid stenosis above a particular threshold (e.g., 80% or greater stenosis), the presence of an unstable carotid plaque, aortoiliac occlusive disease, right arch/left heart and bilateral femoral artery stenoses precluding vascular access, right-sided posterior circulation strokes with an aberrant right subclavian artery, a supreme intercostal right vertebral artery origin, and/or other contraindications.

According to some embodiments, for instance, the following criteria may need to be satisfied in order for a subject to be cleared to move forward with a robotic ischemic stroke treatment procedure: the subject indicates for large vessel occlusion stroke, the subject's carotid stenosis is not greater than a particular threshold (e.g., 70% stenosis), the subject does not have severe intramural calcification, the subject does not have anatomical variants of the aortic arch anatomy, and/or the subject does not have severe vascular tortuosity. In other embodiments, the list of criteria can vary (e.g., fewer or more criteria, different criteria, etc.). In some embodiments, one or more of the criteria can be obtained and/or at least confirmed using CT and/or other technologies.

In some embodiments, a CT scan can be used to determine if a subject is eligible to undergo a particular ischemic stroke treatment by determining certain information, including, without limitation, the location of the large vessel occlusion stroke, the vessels through which the intravascular devices (e.g., catheter, other device, etc.) will need to pass to reach the targeted location of the stroke, the length, angle of origin and/or other details regarding each vessel along a designated path, and/or the like.

According to some embodiments, if a decision is made to perform a procedure (e.g., by the system using certain criteria and analysis, as discussed above), certain steps can be performed manually by the practitioner. Such steps can include, without limitation, vascular access is obtained via the right or left femoral, radial or internal carotid artery, the robotic catheter and other components of the robotic assembly are arranged (e.g., catheter/wire agnostic), the catheter and/or wire are inserted into the formal sheath (e.g., with or without image guidance) and/or the like.

Autonomous Navigation

According to some embodiments, intravascular (or other intraluminal) access of the robotic catheter, other components of the robotic assembly, and/or other devices that will be advanced through the subject can be confirmed by an injection of contrast, automated confirmation of the presence of a surrounding vessel using computer vision, and/or any other confirmatory steps or actions, as desired or required.

In some arrangements, once confirmation of vascular access has been obtained, the system is configured to advance the catheter (and/or any other intravascular device being used) once certain criteria have been satisfied. By way of example, such criteria can include, without limitation, the following: the presence of the catheter (or other device) within a vessel of the subject with a predesignated pathway determined by the system, the tip of the catheter or other device appears regular (e.g., does not appear to be deformed or in any way irregular), the tip of the catheter or other device is oriented in the desired direction (vis-à-vis the predesignated pathway determined by the system), the catheter or other device is being advanced without exceeding a threshold force or pressure (e.g., as determined by a force or pressure sensor secured to the catheter or other device), and/or any other desired or required criteria.

In other embodiments, more or fewer (and/or different) criteria can be used as prerequisites in order to permit the catheter and/or other component of a robotic assembly to be advanced (e.g., to the next step).

Regardless of the exact criteria that the system is configured to consider before permitting the catheter or other device to advance, if at any point at least one of the criteria is not satisfied (e.g., the force or pressure along the distal end of the catheter exceeds a particular threshold level), the system is configured to stop or prevent further advancement of the catheter or other device. In some embodiments, under such circumstances when a criterion is not met, the system can be configured to even retract the catheter or other device by a predetermined distance.

In some embodiments, if one or more criteria are not satisfied, the system can be configured to reassess the situation, including obtaining new imaging and processing of the same. Reassessment can include one or more steps, including, without limitation, real-time non-contrast imaging (e.g., via extravascular imaging technologies (such as, for example, X-ray, external ultrasound, etc.), via intravascular imaging technologies (such as, for example, imaging devices, sensor and/or other features located on the catheter, e.g., ultrasound located along the distal end of the catheter), etc.), real-time contrast imaging (e.g., manual or automated injection of a radiopaque contrast agent), road-mapping via data processing by the system (e.g., the use of a contrast image as a static backdrop which can be presented as a "roadmap" on a display while the catheter or other device is being manipulated), etc.

Figure 5:
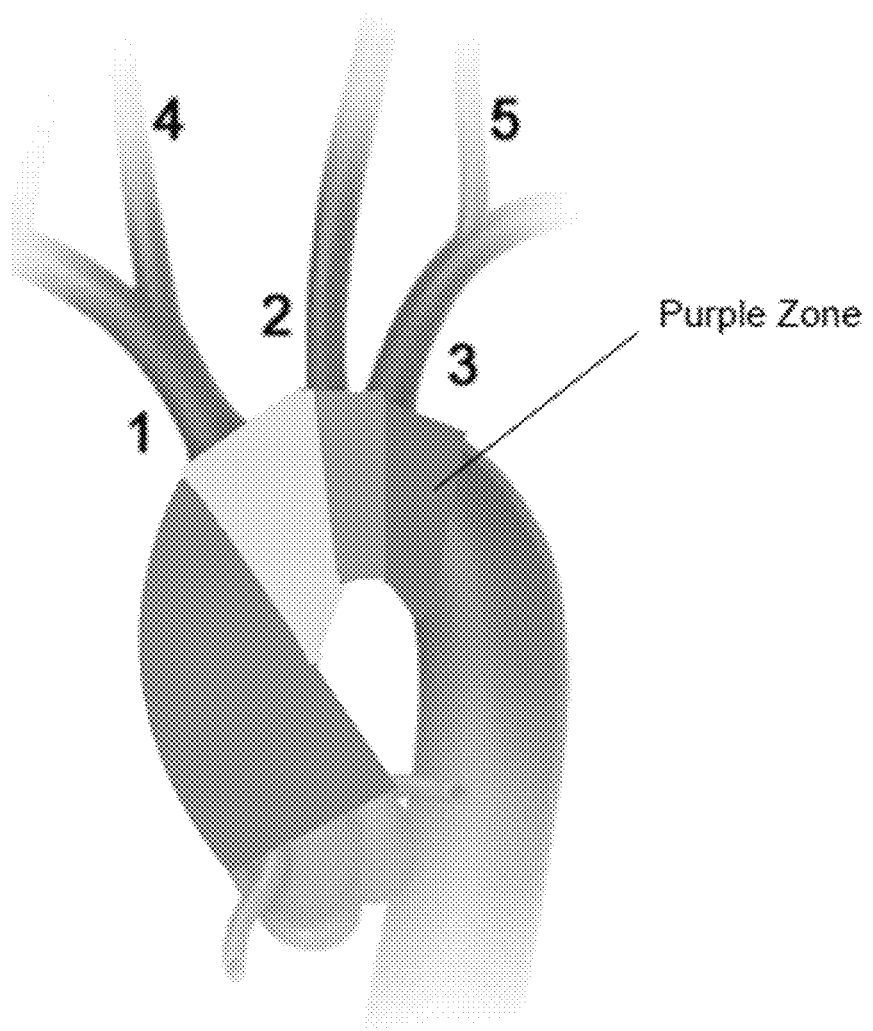
FIG. 5 illustrates one embodiment of an output showing the vasculature of the subject while a catheter is being advanced therethrough.

FIG. 5 illustrates one embodiment of an output showing the vasculature of the subject through which a catheter can be advanced. In particular, FIG. 5 illustrates one or more examples of different zones of the aortic arch in which a surgical robot may initiate turning the instrument or catheter tip to enter into a desired arch vessel. With reference to FIG. 5, in some embodiments, once the catheter or other device of the robotic assembly approaches the origin of the next branch on the predetermined path, the tip of the catheter or other device can be configured to automatically maneuver such that it faces the orifice of the next vessel passageway.

For example, if a catheter is required to enter the Subclavian Artery (Vessel 3 in FIG. 5), the catheter tip can be adjusted (e.g., by automatic manipulation of one or more motors of the robotic assembly) to face the origin of Vessel 3 within the purple zone. The tip can be maneuvered to achieve the desired or required direction (e.g., vis-à-vis the pathway predetermined by the system) by taking appropriate action (e.g., rotating an instrument with a pre-curved tip, adjusting the tip of an articulable catheter or other instrument, etc.), as desired or required.

According to some embodiments, if a catheter or other device is moved into a zone or area (e.g., vessel, vessel branch, etc.) that is not on the desired path predetermined by the system, the system is configured to automatically stop further progression of the catheter or other device. In some embodiments, the catheter or other device is at least partially retracted under those circumstances. However, in other embodiments, under such circumstances, the system can be configured to stop progression of the catheter and alert the practitioner. The practitioner can be prompted to decide what to do next (e.g., continue advancing the catheter in conflict with the predetermined pathway, stop progression of the catheter, retract the catheter, etc.).

As discussed above, a contrast injection (e.g., automatically or manually administered) can be used to confirm the presence and location of the filling defect (e.g., clot). In some embodiments, a wire and/or a catheter (e.g., a microcatheter) is the passed a predetermined distance distal to the commencement of the clot.

In some embodiments, based on one or more confirmatory conditions (e.g., the appearance of angiogram and CT scan), the system is adapted to make a decision on the nature of the intervention to be performed. In some arrangements, following the execution of the directed intervention (e.g., suction thrombolysis, stent retrieval, etc.), further contrast can be injected to enable an automated assessment of the degree of cerebral perfusion. Based on this assessment of reperfusion the procedure can be terminated or repeated.

According to some embodiments, in cases involving mechanical thrombectomy for LVO stroke treatments, the catheter can be configured to follow an initial common path. One example of such a common path includes: the femoral artery to the external iliac artery to the abdominal/thoracic aorta to the aortic arch.

In some embodiments, the catheter is then directed by the system along a number of directories depending on the location of the targeted clot. For example, in some embodiments, the number of directories is six (e.g., 3 on the right, 3 on the left). For example, in arrangements where the clot or other targeted location is in left middle cerebral artery (MCA), the pathway can be: aortic arch to left common carotid to left internal carotid artery to the point of bifurcation to MCA.

According to other embodiments, where the clot or other targeted location is in the left anterior cerebral artery (ACA), the pathway can be: aortic arch to left common carotid artery to left internal carotid to the point of bifurcation to ACA.

According to some configurations, where the clot or other targeted location is in the left vertebral artery (VA), the pathway can be: aortic arch to left subclavian artery to left vertebral artery.

Systems, Methods, and Devices for Assisted Teleoperation of Robotic Endovascular Intervention—General As discussed in more detail herein, in some embodiments, the systems, devices, and methods described herein are configured to provide assisted teleoperation of robotic endovascular intervention. More specifically, in some embodiments, the systems, devices, and methods described herein allow for a remotely located or on-site surgeon to control a surgical robot for endovascular intervention or other procedures related to the vasculature by providing input into a personal computer (PC), tablet PC, smartphone, and/or other electronic device. For example, in some embodiments, the system can be configured to obtain, access, and/or analyze one or more medical images of the vasculature, such as, for example, an x-ray image. In some embodiments, the system can be configured to cause the electronic device to display a lateral view of the vasculature based on such one or more medical images. In some embodiments, the system can be configured to use one or more contrast agents to further clarify an x-ray image. In some embodiments, a surgeon can use his or her finger, a mouse click, a pen, or any other input method to point at one or more waypoints along a desired pathway within the displayed vasculature for a tool to proceed. In some embodiments, based on such user input, the system can be configured to automatically, dynamically, and/or algorithmically calculate or determine a pathway for the tool to proceed from one waypoint to another waypoint inputted by the user and cause a surgical robot to advance the tool accordingly. In some embodiments, the system can be configured to utilize one or more machine learning and/or artificial intelligence algorithms to determine a pathway for the tool to advance from one waypoint to another waypoint. As such, in some embodiments, the system can be configured to provide an assisted, subtask automated, semi-autonomous, augmented, macro-level, and/or step-by-step navigation of a surgical tool within the vasculature.

In some embodiments, the system can be further configured to suggest a next movement within a vasculature and/or an intervention or procedure therein. In some embodiments, the system can be configured to allow a user or surgeon to change or modify a suggested trajectory or pathway developed by the system. As such, in some embodiments, the system can allow a user or surgeon to verify, confirm, and/or modify one or more parts of a trajectory or pathway determined by the system. In some embodiments, the system can be configured to learn from the surgeon's confirmation and/or modification of a pathway or trajectory suggested by the system, thereby improving future suggested pathways and/or trajectories. In other words, in some embodiments, the system can be configured to use one or more machine learning and/or artificial intelligence algorithms to determine initially a suggested pathway or trajectory between two waypoints, and the system can further be configured to use one or more machine learning and/or artificial intelligence algorithms to improve such pathways or trajectories that it suggests. In some embodiments, as the system improves or learns from prior data, the distance between two waypoints inputted by the user within a vasculature can become more distant. In other words, in some embodiments, with stepwise input from a user, for example, in terms of closely located waypoints and/or confirmation or modification of suggested pathways between waypoints, the system can be configured to verify its performance and improve. As such, in some embodiments, the surgeon or user can use and train the system at the same time.

In some embodiments, input of such waypoints or macro-level navigation can be distinguishable from providing continuous user input. As described in more detail below, providing continuous user input along a desired pathway for a tool within the vasculature can require substantial amounts of data to be transmitted from the user input device to the system and/or a surgical robot, thereby creating a number of technical issues for teleoperation such as lag, stability, trust levels of the procedure, and/or the like. In contrast, in some embodiments, by providing such assisted navigation of a tool within the vasculature, the amount of user input data necessary to be transmitted can be substantially decreased, thereby solving such technical issues and making teleoperation possible.

At the same time, by allowing the user to provide waypoints along a desired trajectory or pathway, the system can be configured to operate at a high confidence level without requiring full knowledge or information of the environment by the system. For example, in some embodiments, if a user or surgeon provides one or more waypoints along a desired pathway along the vasculature, the system does not need to know or determine by itself the whole mapping of the vasculature, which may include bifurcations, turns, and/or the like. Rather, in some embodiments, the system can rely on the waypoints inputted by the user for much of this information, while at the same time provide assisted or subtask automated navigation between two waypoints.

In other words, in some embodiments, the systems, devices, and methods described herein are configured to provide task space control as opposed to actuation space control. More specifically, in some embodiments, the system is configured to allow a user to control a surgical robot through the domain which is most relevant to the task, for example by pinpointing one or more locations on a medical image or x-ray image, without a direct mapping of user control, for example between a joystick input and movement of the actuators.

As such, in some embodiments, the systems, devices, and methods described herein can comprise and/or be directed to a control paradigm for surgeons interacting with surgical robots, such as, for example, for teleoperation of robotic endovascular intervention. More specifically, in some embodiments, a surgeon can interact with a surgical robot, such as one for endovascular intervention, by indicating one or more target locations on a displayed medical image, such as on a personal computer, laptop, tablet personal computer, or smartphone, for the surgical tool to reach.

In particular, in some embodiments, the system can be configured to receive input from a surgeon that is remotely located from the surgical robot. In some embodiments, the input from the surgeon can comprise one or more waypoints or targets along a desired pathway for a tool to proceed along a vessel, artery, and/or the like. In some embodiments, the system can be configured to receive macro-level direction or guidance from a surgeon, while the system can be further configured to augment such user input to provide a semi-autonomous guidance system. In some embodiments, the system can be configured to utilize one or more machine learning and/or other algorithms to analyze one or more medical images of the endovascular network to automatically determine and guide the tool through the endovascular network to reach the user-inputted waypoint or target. In some embodiments, the system can be configured to utilize one or more machine learning and/or other algorithms to identify the location of a tool, such as a catheter, and/or suggest a next movement within an endovascular vessel.

In some embodiments, the surgeon may also interact with the robot by suggesting one or more interventions and/or assessing the success of one or more interventions. In some embodiments, the robot may run one or more computer vision algorithms to detect the tool tip location and/or orientation. In some embodiments, the system uses one or more predefined algorithms, such as, for example, inverse kinematics, Jacobian, and/or the like, and may include visual closed-loop control to move the tool toward the target location.

In some embodiments, the system may be used in local and remote teleoperation conditions. In some embodiments, this paradigm can enable remote teleoperation in particular by doing one or more of the following: freeing the surgeon from a hardware-specific console, reducing training time, providing safeguards against unexpected network latency, and/or warning the surgeon about unsafe actions.

In some embodiments, the systems, devices, and methods described herein are configured to be used specifically for endovascular procedures by leveraging certain features specific to endovascular procedures. For example, in some embodiments, the systems, devices, and methods described herein are configured to utilize contrast opacified x-ray images as input, which is generally unique to endovascular procedures. Also, in some embodiments, the systems, devices, and methods described herein are configured to utilize two-dimensional (2D) images in only one or two planes to navigate, which is generally possible for endovascular procedures but not for navigation of general tissue as discussed herein. Moreover, in some embodiments, the clinical decisions made by the system are unique to endovascular procedures, which can include for example perfusion analysis, deciding which interventions to perform, and/or the like. Further, in some embodiments, the use of instrument position and/or tip position as a safety feature is also unique to endovascular surgery.

In addition, in some embodiments, the systems, devices, and methods described herein are configured to utilize the X-ray imaging modality that shows the 2D "map" or "roadmap" of the vasculature and/or anatomy. In some embodiments, the systems, devices, and methods described herein are configured to solve the navigation of tools through the vasculature and/or anatomy. As such, in some embodiments, user intent can be distilled into points, lines, directions, and/or the like on this 2D map for the instrument to be guided through.

In contrast, for any extravascular surgical robotic procedure, such as through use of the Intuitive Da Vinci Surgical System, tissue manipulation can be critical and complex. In such cases, the image viewed through the camera may not provide enough features for the user to define their intent with clicks of a mouse or taps on the screen. As a result, unlike some systems, devices, and methods described herein, these systems for extravascular robotic procedures rely on multi-degree of freedom consoles for the user to express their intention.

In addition, for any surgical robotic endoscopic procedure, such as bronchoscopic, gastrointestinal, genitourinary, and/or the like, by use of, for example, the Auris Monarch Platform, navigation may be performed using feedback from a distal camera. This can provide a view within the lumen, containing a small subset of the total anatomy the user will navigate through. In such cases, the motion of the device can be characterized as being "into" the image, rather than "across" the image. As such, in such cases, the user interface of a gaming controller with first-person shooter style controls can allow the user to intuitively control the advancement into the anatomy; however, selecting points on a 2D image may lose the critical depth component that is required when advancing forward with these devices.

Furthermore, as discussed herein, the clinical value of performing endovascular procedures remotely can rely on the time-criticality of the emergency. To this end, some embodiments of the systems, devices, and methods described herein and/or an interface thereof can enable remote teleoperation to treat patients sooner and therefore improve outcomes. In contrast, most if not all other surgical robotic systems on the market focus on elective procedures, for which remote teleoperation would offer limited to no clinical benefit.

Systems, Methods, and Devices for Assisted Teleoperation of Robotic Endovascular Intervention—Additional Detail As a non-limiting example, for a patient located three hours away, who needs a mechanical thrombectomy (MT), it can be important to have such patient undergo treatment there and then. Generally speaking, neurointerventionalists (NI) who perform MT are concentrated, and will likely remain so, in large academic centers (for example, only in about 2% US hospitals). Other specialties have shown a lack of willingness to perform MT for a number of reasons. This problem may be solved if an NI could perform the procedure remotely by teleoperating a surgical robot in the hospital with the patient. However, there are currently various technical shortcomings that do not allow for such teleoperation. Some embodiments described herein address such technical shortcomings to make it safe, simple, and accessible for clinicians to guide and monitor a remote intervention.

As mentioned above, at the moment there are significant barriers to remote teleoperation, which may typically involve a remote clinician sitting at a robotic console, using a joystick to control each movement of the catheter. From a safety perspective, one significant technical problem is that any risk of connectivity disruption may present significant difficulties and potential safety risks when directly controlling the motors, which is the standard control methodology for all currently existing invasive surgical robots. Additionally, for vascular robots in particular, the surgeons must relearn how to perform the procedure with the robotic console, which is significantly different than the wires and catheters they learned to manipulate in their training. When performing robotic intervention using a traditional robotic console, a treating team may need to spend 30 hours or more familiarizing themselves with the robot controls and console. Part of this may have to do with the existing vascular robots using pre-curved wires, which are the more popular device for experienced NIs. These devices, wire and sheath over wire, require a lot of jiggling, trial and error, and back and forth. As a result, certain NIs take pride in their "touch," which is hard to translate into the robotic console. Finally, currently existing consoles are expensive electromechanical systems that would strain the healthcare system to distribute in a meaningful way that would affect time critical outcomes.

In contrast, some embodiments of the systems, devices, and methods described herein enable remote teleoperation of endovascular procedures by augmenting the remote surgeon with AI-powered assistance. In other words, in some embodiments, remote teleoperation of endovascular procedures is enabled by augmenting the remote surgeon with AI-powered assistance. As such, in some embodiments, such assisted interfaces can increase the safety and accessibility of these time critical procedures.

More specifically, in some embodiments, the interface for the remote specialist comprises a generic personal computer (PC), tablet PC, or smartphone, or other computing device that can stream one or more real-time medical images, such as a chest x-ray image(s), from the remote operating room. In some embodiments, the one or more images may be augmented with one or more highlights and/or other renderings, charts, and/or the like, for example, to show the specialist where the tool tip is, where key anatomies are, what configuration the tool is in, and/or the like.

In some embodiments, the system can be configured to use a lateral and/or frontal view x-ray image(s). In some embodiments, the system can be configured to perform a two-dimension (2D)/three-dimension (3D) registration. For example, in some embodiments, the system can be configured to utilize a 3D pre-operative model of the vessel and overlay information from the same such that 2D input by a surgeon can be interpreted relative to the 3D knowledge of the map. In some embodiments, the system can be configured to utilize such 3D information to maintain a position of a tool at the middle of a blood vessel as it is advanced therethrough.

In contrast, in some embodiments, the system may not use any such 3D information, for example from a 3D model of the vessel. More specifically, in some embodiments, the system can be used to guide a compliant and/or flexible tool within the vasculature, which can allow the system to ignore or not consider 3D information as the tool will mostly comply with the environment as long as it is not exerting too much force.

In some embodiments, the systems, devices, and methods described herein allow a remote specialist to define one or more points to navigate to (or agree/disagree with a suggested path), select an intervention (or agree/disagree with a suggested intervention), and/or assess the success of the intervention (or agree/disagree with a suggested assessment). In some embodiments, this can increase safety by providing safeguards against unexpected network latency, warning the surgeon about unsafe actions, and/or reducing procedural complexity and training time. In some embodiments, it can also increase the accessibility of surgical expertise by freeing the surgeon from a traditional robotic console.

Figure 6:
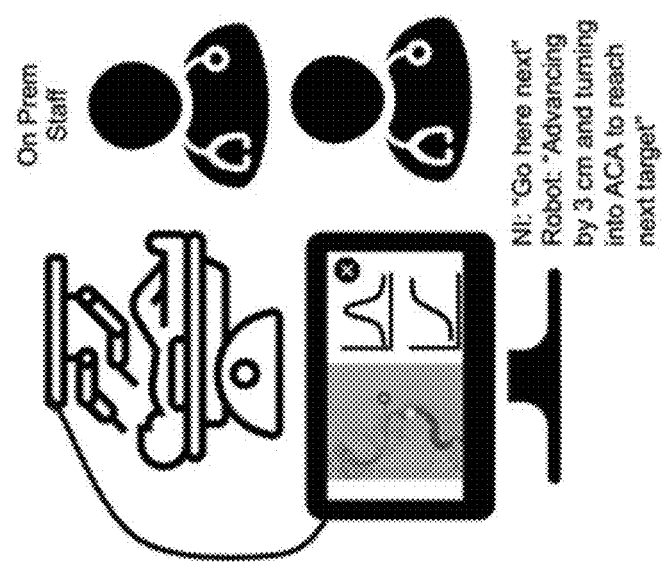
FIG. 6 illustrates an embodiment(s) of a system and/or method for teleoperation of robotic endovascular intervention.
Figure 6:
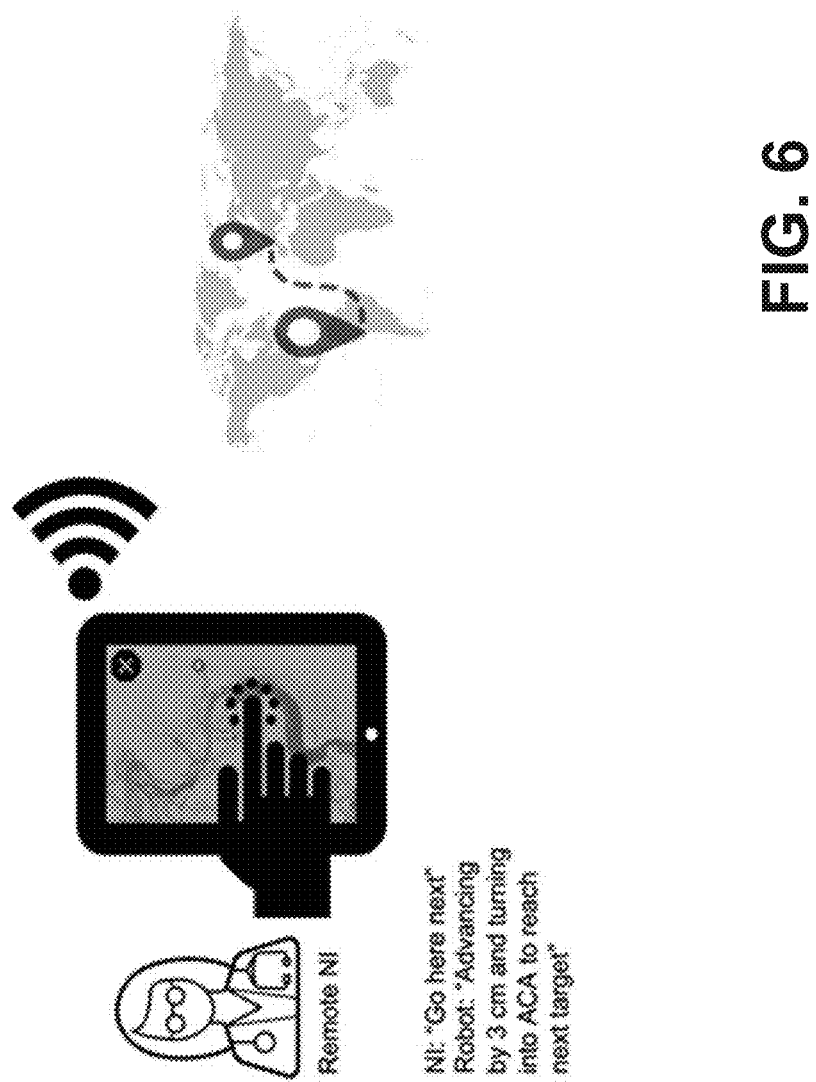

FIG. 6 illustrates an embodiment(s) of a system and/or method for teleoperation of robotic endovascular intervention. In some embodiments, the system comprises one or more modules, including one or more modules illustrated in FIG. 6. As illustrated in FIG. 6, in some embodiments, a remote surgeon, such as a neurointerventionalist, may interact with a personal computer (PC), tablet PC, or other electronic device to communicate the next target location for the tool top to advance towards. In some embodiments, this command or user input is received by a surgical robot that is remotely located. In some embodiments, such command or user input can also be displayed to surgical staff located next to the patient and/or the surgical robot. In some embodiments, the surgical robot can acknowledge the command and communicate its planned behavior to the on-site surgical staff and/or remote surgeon.

In other words, in some embodiments, the system can be configured to allow a physician to interact with a surgical robotic system through a graphical interface on an electronic device, such as a personal computer (PC), tablet PC, smartphone, and/or other device. In some embodiments, the graphical interface may be viewed and interacted with on a plurality of devices.

In some embodiments, a wired or wireless connection can be made between and/or among one or more of the electronic device, the surgical robot, and/or the imaging machine. In some embodiments, the images obtained from the imaging machine are displayed on the electronic device through the graphical interface. In some embodiments, a computer vision algorithm may detect and/or highlight the position and/or orientation of the surgical tool on the displayed image.

In some embodiments, the user may command the robot by selecting a pixel and/or region on the image. In some embodiments, the user may also indicate a desired orientation of the tool at that desired location. In some embodiments, the selection may be executed through a mouse click, keyboard stroke, and/or touch on a touch sensitive display. In some embodiments, the system and/or software operating on the system can be configured to calculate the change in instrument configuration and/or change in motor positions that may enable the instrument to reach the target location.

In some embodiments, the system and/or software operating on the system may display the action the robot will take and may ask for confirmation by the user or set of users before executing the action. In some embodiments, when the instrument reaches the target within a set error threshold as observed visually by the software or user, or if it determines that it cannot reach the target, it will notify the user. In response, in some embodiments, the user may select a new target location. At any point, in some embodiments, the user or users may send a command to stop all robot motion.

In some embodiments, the graphical interface may expose more direct control of the motors to the user(s). For example, in some embodiments, this may include the ability to jog each motor by a set amount. Further, in some embodiments, this may include the ability to drive the motor by a set velocity for a configurable amount of time, for example, while the user holds a button.

In some embodiments, the software may suggest one or more target locations, which the user can accept or modify. In some embodiments, the software may suggest one or more clinical decisions, such as which type of intervention to try and/or the like. In some embodiments, the software may report clinical indicators, such as perfusion analysis.

In some embodiments, the software may identify and store the location of one or more blood vessels. In some embodiments, this information may be used to suggest target locations, improve the motion control algorithms, and/or warn the user of unsafe actions.

In some embodiments, the system and/or computer vision algorithm(s) operating on the system may include machine learning and/or deep learning to identify the location and/or orientation of an instrument, such as for example a catheter. In some embodiments, the algorithms may include one or more computer vision techniques to identify the instrument location and/or orientation. In some embodiments, the instrument may include specific radio-opaque markings to facilitate the visual identification of the tool location and/or orientation. In some embodiments, the markings may be rings, dots, stripes, codes, barcodes, other polygons, and/or the like. As such, in some embodiments, the system can be configured to identify the location and/or orientation of an instrument based on such markings.

In some embodiments, the system and/or software operating on the system may present the estimated three-dimensional (3D) shape of the surgical tool to the physician. In some embodiments, the physician may be able to interact with the 3D rendering to provide one or more commands to the robot. In some embodiments, the 3D shape may be overlaid on the registered 3D scan of the anatomy and/or on a 2D medical image, such as an x-ray image.

In some embodiments, the systems, methods, and devices described herein are advantageous in that they simplify and/or augment the user input process, thereby making endovascular teleoperation using a surgical robot possible. In particular, in some embodiments, the systems, methods, and devices described herein allow for controlling a surgical robot through image and/or pixel-based commands or task space control. In some embodiments, such a novel technical feature that has never been introduced clinically can allow the surgeon to use a traditional PC, tablet, or other device rather than the expensive consoles built by the surgical robotics manufacturers. In addition, in some embodiments, this can also reduce associated costs, thereby increasing the accessibility of remote control. Further, in some embodiments, this can reduce training time through an intuitive control paradigm that is consistent with standard surgical training.

Moreover, in some embodiments, the systems, methods, and devices described herein are advantageous in that they comprise the necessary algorithm(s), user interface(s), and/or model(s) to provide an image-based and/or fully image-based user interaction and/or control system. In some embodiments, image-based commands are an abstraction that requires image-based understanding by the robotic system. As such, in some embodiments, the system may comprise a computer vision algorithm that detects the tool tip and orientation. In some embodiments, the system may comprise an option for the user to manually identify the tool tip and/or orientation. In some embodiments, the system may include an analytical or learned kinematic model of the instrument and the robotic interface.

In addition, in some embodiments, the systems, methods, and devices described herein are advantageous in that image-based commands are less sensitive to unexpected lag times in the communication between the remote controller and the robot. This can be because the commands are discrete steps rather than continuous updates. In other words, in some embodiments, the system can be configured to provide and/or allow for step-by-step navigation. For example, in some embodiments, the user can provide one or more macro directions (as opposed to micro directions), one or more waypoints, or stepping stones along a desired pathway, and the system can be configured to augment such user input to provide semi-autonomous navigation that does not require continuous user input.

Further, in some embodiments, the system or software operating on the system can suggest commands through the same interface, which the remote surgeon can accept or modify as they see fit.

Furthermore, in some embodiments, the system or software operating on the system may provide an assessment of whether or not instruments are safely positioned based whether or not they have deviated from a predefined path, their appearance (bowing of the body, scrambled tip), force/friction measurement, and/or the like.

In some embodiments, the system or software operating on the system may enable a remotely located person to: observe a predefined path or define a path to be followed; monitor/confirm a suggested intervention or suggest an intervention; and/or monitor/confirm procedure completeness/reperfusion or suggest procedure completeness/reperfusion.

Figure 7A:
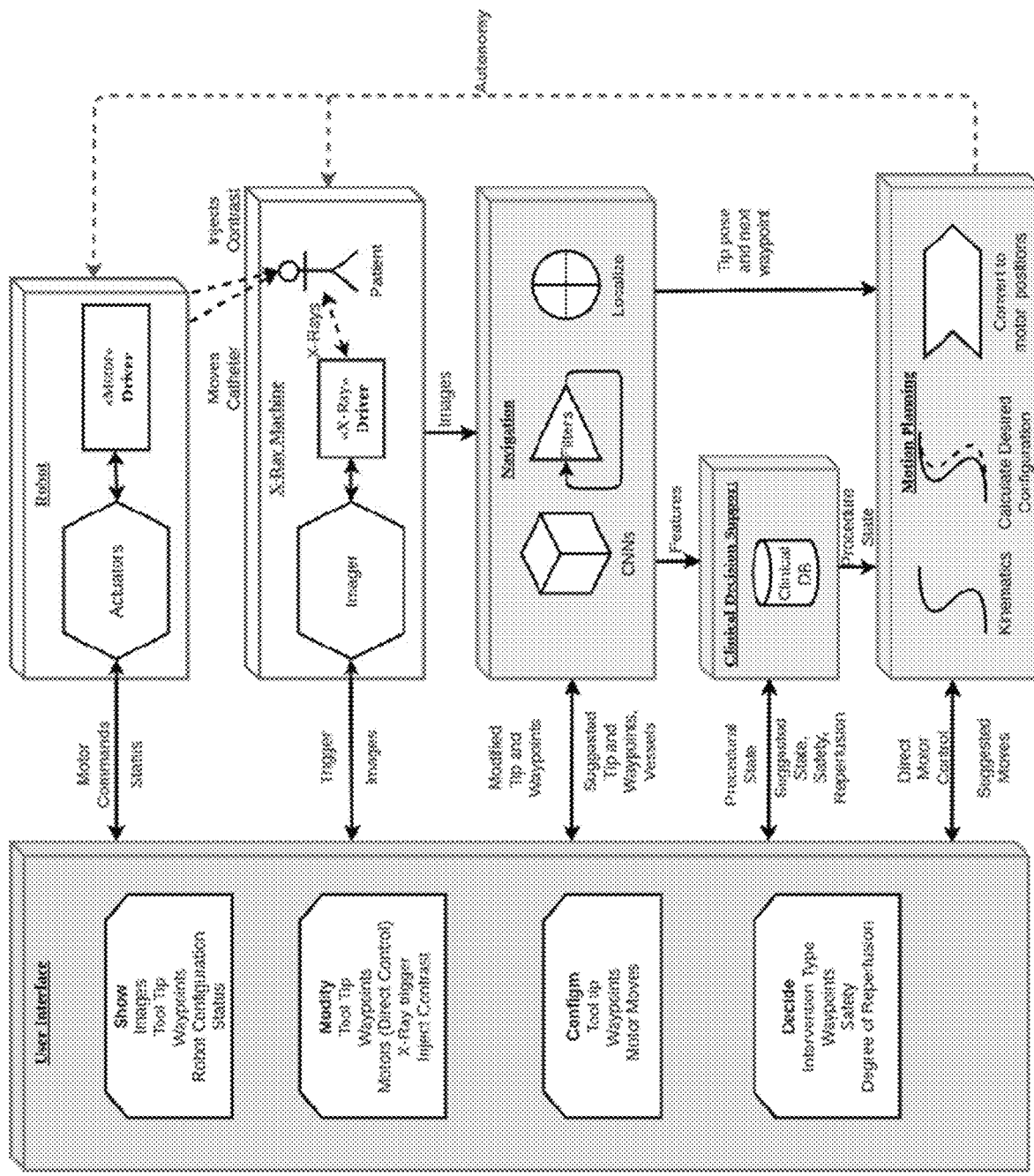
FIG. 7A illustrates an embodiment(s) of a system and/or method for teleoperation of robotic endovascular intervention.

FIG. 7A illustrates an embodiment(s) of a system and/or method for teleoperation of robotic endovascular intervention. As illustrated in FIG. 7A, in some embodiments, a user interface (UI) communicates with nearly every module or one or more modules in the robot control loop, allowing for system behavior spanning from direct control by the user to nearly full autonomy. In the illustrated embodiment(s), the system modules are shown as black boxes, algorithms within modules are blue, information flow is shown as arrows with the information content shown in red next to each arrow. In some embodiments, the autonomous loop may or may not exist, and in some embodiments, this is regulated by the user via the UI. The embodiment(s) illustrated in FIG. 7A demonstrates how the system, in some embodiments, would enable image space control and direct motor control. In some embodiments, machine learning algorithms may assist in the subtasks contained in the Navigation module, which would supply potential waypoint, tool tip and orientation, vessel location, and/or other information to the UI to be displayed to the user.

Figure 7B:
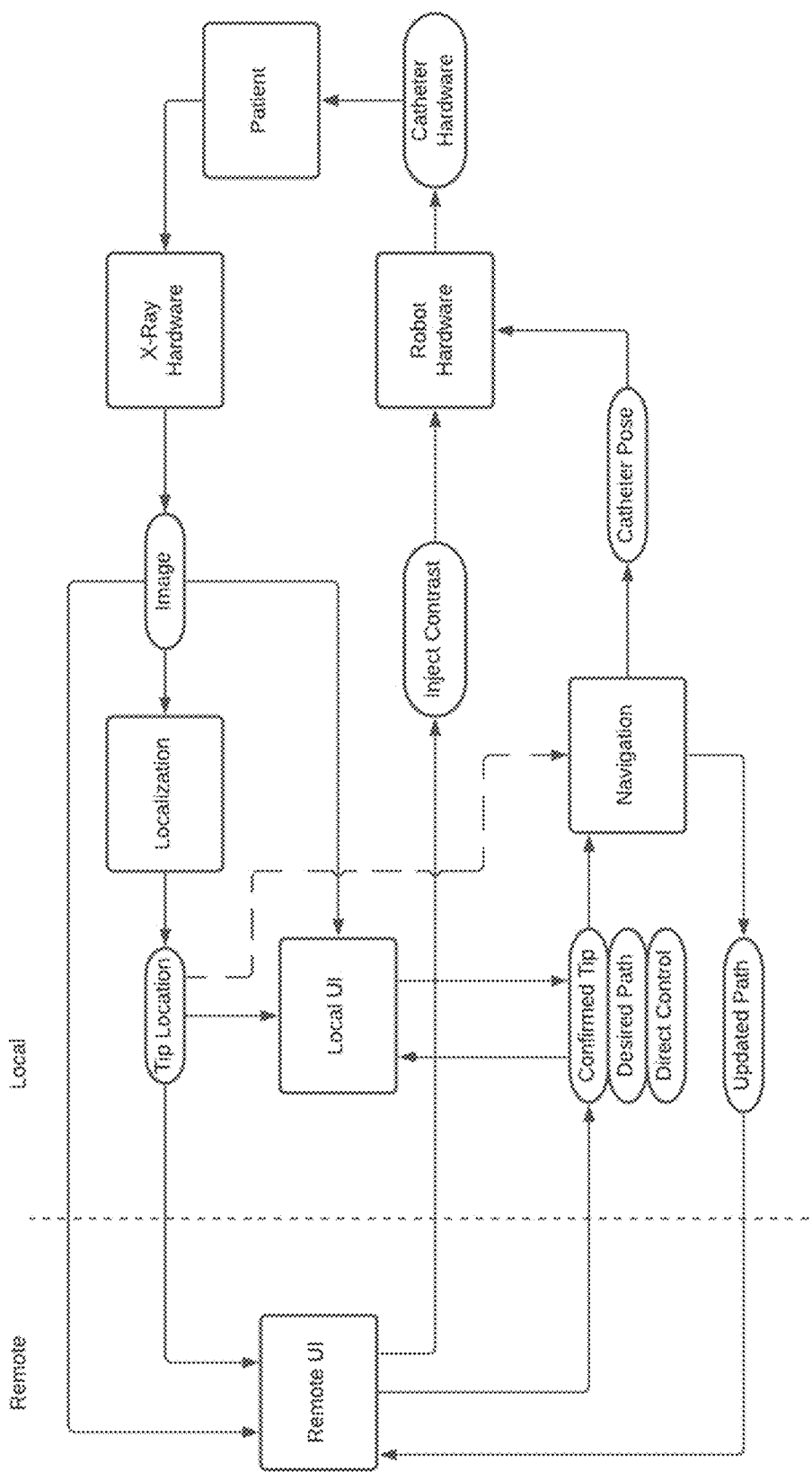
FIG. 7B illustrates an embodiment(s) of a system and/or method for teleoperation of robotic endovascular intervention.

FIG. 7B illustrates another embodiment(s) of a system and/or method for teleoperation of robotic endovascular intervention. In particular, FIG. 7B illustrates an example information flow between a local operating room (e.g., where the patient is located) and a remote location (e.g., where the remotely-located physician performing the procedure is located). The remotely-located physician is able to generate motion commands that can be sent to and/executed by robot hardware located at the local site. Information from the local site is collected and communicated back to the remotely-located physician.

As shown in the example of FIG. 7B, at the beginning of a cycle, images (e.g., X-ray image(s)) that contain the catheter tip can be collected of the patient using x-ray hardware or other imaging devices. These images are processed, which can include performing localization steps to identify the position and/or orientation of, for example, a distal tip of the catheter in the image. This positional information along with one or more images, for example, the most recent image is sent to the remote interface (e.g., the device that the physician is using to control the procedure).

In some embodiments, the physician can then confirm the that the current catheter tip location and/or orientation is in a safe pose to continue the operation, and select either a path to move along or direct control of the catheter pose. As shown in FIG. 7B, these commands can be sent back to the local system where they may, in some embodiments, be confirmed again by a local operator.

Motion planning algorithms in the navigation module may determine the most appropriate catheter motions in order to move the tip along the desired path, or convert direct motion commands into pose updates. The navigation module may also supply potential waypoint, tool tip and orientation, vessel location, and/or other information to the UI (e.g., the remote UI) to be displayed to the user. The new catheter pose can then be sent along to the robotic hardware which will move the catheter hardware. This control loop cycle can then be verified and/or repeated by using the x-ray hardware to detect this motion.

Notably, in some embodiments, the system uses the current tip location in the navigation algorithms. This can allow embodiments in which an autonomous loop exists regulated by the user via the UI.

Example Use and User Control

In some embodiments, the systems, devices, and methods described herein can be configured to allow a user to control a remote surgical device through image space control and/or direct motor control. In some embodiments, for image space control, the user or specialist can select a next region on a displayed medical image for the tool tip to navigate towards. In some embodiments, the radius of the region and the distance the region can be placed relative to the tool tip depends on the capabilities of the system. In some embodiments, the tool tip, the acceptable region for the next way point, and the selected way point would be highlighted. In some embodiments, once selected, the interface can display the expected sequence of motions the robot will execute and a progress bar for this action. As discussed in further detail herein, in some embodiments, the robot may use open loop or closed loop control for these navigation subtasks. In some embodiments, the system can be configured to suggest one or more way points based on its analysis of the image that can be edited by the user. In some embodiments, the system may provide ease of use tools, such as auto adjusting way points to the center of the relevant vessel. In some embodiments, image space control can be main control methodology.

In addition and/or alternatively, in some embodiments, the system can be configured to allow a user or specialist to directly interface with the motors through direct motor control. While more difficult to use than image space control, this can provide a safety mechanism for the user in some embodiments. For example, in some embodiments, if the user does not agree with the robot's approach to the next way point in image space control, the user can exert explicit control. This may be represented in one or more of many different interfaces, such as for example arrows/buttons that move each motor at set slow speed while you hold the button down, or a combination of sliders and/or dials that directly map to the position of each motor, or a rendering of the tool and its degrees of freedom that can be dragged into different configurations. In each iteration, in some embodiments, the user can exert direct, real-time control over the actuators. However, while a useful safety mechanism, it can be burdensome to use for extended periods given the necessary feedback frequency for such a task.

In some embodiments, the system can also comprise an emergency stop button to cease all motor movement.

In some embodiments, all or a subset of these controls can be exposed to the remote user and/or to the on-premise staff. In other words, in some embodiments, the system can be configured to provide a collaborative teleoperative interface that enables collaboration over great distances.

In some embodiments, to use the systems, devices, and methods described herein for an endovascular procedure, an on-site clinician or medical personnel can dock and mount a surgical robot for the endovascular procedure. In some embodiments, arterial access can be achieved via a human, such as an on-site clinician or medical personnel. In some embodiments, arterial access can be achieved by a robot with computer vision. In some embodiments, sheath can be inserted and connected to the robot, a first contrast can be injected, and/or a generating a roadmap of the vasculature can be initiated. In some embodiments, a physician, who can be on-site or remotely located, can identify on a remote console the next point or realign a set of predefined points. For example, in some embodiments, the physician can use a mouse click, pen tap, finger tap, and/or the like to input on a user device, such as a generic PC or tablet PC, one or more points for traveling the tool. In some embodiments, a radius of error can appear around the point inputted by the physician and/or the tip of the instrument or tool. In some embodiments, upon navigation to each point, a new contrast injection may or may not be triggered. In some embodiments, in addition to navigation, the system can provide suggested treatments, resolution of pathology, and/or the like that the physician may modify and/or confirm.

Navigation

As discussed throughout this disclosure, in some embodiments, the systems, devices, and methods described herein can comprise and/or be configured to provide image space control. To provide image space control, in some embodiments, the system can be configured to identify the tool tip location, for example, in real-time or substantially real-time.

In some embodiments, the system can be configured to identify the tool tip orientation, for example, in real-time or substantially real-time. In some embodiments, the user may perform this identification and/or an algorithm may perform the identification of the tool tip location and/or orientation.

In some embodiments, the tool tip location and/or orientation may be displayed as a highlighted circle, oval, arrow, body segmentation of the tool, and/or any other visual graphic. In some embodiments, the information may be used by the user to determine the next way point and by the instrument control algorithm to determine the path the robot needs to take to the next way point. In some embodiments, this information may help determine the validity of the next way point based on distance in image space or other features such as continuous vessel access.

In some embodiments, the system can be configured to utilize one or more of machine learning algorithms to determine the location and/or orientation of a tool tip. Some of such example machine learning algorithms can include: pixel segmentation (ex architecture: UNet, ex loss: jaccard loss); bounding box (ex architecture: RetinaNet, ex loss: intersection over union loss); regression (ex architecture: ResNet, ex loss: Euclidean distance [L2]), and/or the like.

Additionally, in some embodiments, the tools can be modified with radio opaque markings that would improve their visibility in the image. For example, markings on the articulating section may include rings, dots, other polygons or shapes, and/or other coded information. In some embodiments, these markings can be identified with template matching algorithms, finding contours, and/or the like. In some embodiments, these markings may also be identified using one or more machine learning algorithms, such as any of those discussed herein.

As a safety feature, in some embodiments, the user may override the system-predicted position and/or orientation of the tool tip. In some embodiments, the orientation of the device can be determined from the orientation of the segmentation (oval rather than circle, or segmentation of body length), bounding box (use two, one on tip to body point predefined distance before, other on tip and predefined distance ahead of tip; can use padding on points to prevent zero, but limits resolution), can regress the orientation or classify it to discrete angles. In some embodiments of segmenting the device, a segmentation network such as U-Net may be used to generate a specific shape, such as an oval, circle, or other shape, on the tip of the device. In some embodiments, the centroid of the segmented pixels could indicate the tip location or a separate segmentation could be leveraged to distinguish the tip location. As a non-exhaustive list, the orientation could be determined by the singular value decomposition (SVD), RANSAC, least spares, or an ellipse could be fit to the contour. In embodiments of a bounding box, a single box can leave ambiguity about the direction of the tool tip; however, in some embodiments, two boxes can alleviate that ambiguity. In some embodiments, one box can be centered on the tip or it can locate one corner to the tip with the opposite corner a set number of pixels along the body behind it. In some embodiments, the second box can locate one corner to the tip as well with opposite corner a set number of pixels beyond the top extending in the direction of the tip. In some embodiments, a minimum width and/or height can be set to avoid horizontal and/or vertical edge cases. In embodiments of regressing the tip position and/or orientation, an L2 norm loss or any variant of a distance-based metric, such as cosine distance for orientation, could be used to estimate the pixel location and angle of the tip. In some embodiments, the position and/or orientation could be discretized such that the problem could be cast as a classification problem which would leverage a cross entropy loss or other probabilistic loss for misclassification.

In some embodiments, the system can be configured to utilize one or more machine learning algorithms, such as the ones discussed herein, in isolation and/or in conjunction with others, for example, to improve robustness.

In some embodiments, the system can be configured to utilize one or more vessel detection algorithms. In some embodiments, use of a vessel detection algorithm may improve the user experience and/or may offer safety advantages while controlling the instruments. In some embodiments, one or more vessels may be shown in stages according to the algorithm sophistication, including for example: none highlighted, general highlighting of relevant vessels, and/or specific highlighting based on anatomical classification. In some embodiments, the vessel detection may influence the behavior of the clinician's way point selection. In some embodiments, the user may select any point, or points may be limited to vessels, or points may be limited to vessel centerlines, or points may be limited to vessel centerlines on the predefined path. In some embodiments, the vessel detection may also inform the system or software's suggested way points. In some embodiments, it may suggest points on the centerlines of the vessels on the predefined path.

In some embodiments, vessel detection by the system can be sufficiently accurate to suggest way points for the entire procedure. In some embodiments, the system can be configured to utilize one or more additional statistical or rules-based algorithms, for example to determine the optimal intervention and/or to determine if the intervention was successful throughout the entire procedure or a portion thereof.

Motion Planning/Instrument Control

In some embodiments, the systems, devices, and methods described herein can comprise and/or be configured to utilize one or more motion planning and/or instrument control algorithms. In particular, in some embodiments, the system can comprise and/or be configured to utilize one or more algorithms that calculate how the instrument configuration and/or motor positions should change to move towards the target in image space.

In some embodiments, the system can comprise and/or be configured to utilize one or more of inverse kinematics, Jacobian, and/or other algorithms for instrument control in isolation or in combination.

In some embodiments, the orientation of the x-ray imaging system is known relative to the axis along with the device rotates. In some embodiments, this can simplify the 3D control of the catheter to a 2D problem by aligning the device rotation such that the articulation moves predominately in the visible plane. In some embodiments, this plane can be determined by rotating the device and identifying the rotation at which maximum displacement of the tip is observed from the catheter body. In some embodiments, once the device is in the plane, the controls can focus primarily on the insertion and articulation degrees of freedom, which can be better suited for the 2D input space. In some embodiments, a second imaging plane may be used to determine a plane for articulation between with set imaging plane. In some embodiments, a 3D preoperative scan may be used to calculate the optimal articulation planes along the path to the target anatomy. In some embodiments, as the device inserts through the anatomy, it may update the articulation plane according to the preplanned optimal planes.

For inverse kinematics, in some embodiments, the system can be configured to utilize as inputs one or more of: pixel estimate of the tool tip; estimate of the tool tip's orientation in the image plane; way point pixel location; actuator positions of device rotation and actuation; kinematic model of the instrument (part of function); and/or the like. Optionally, for inverse kinematics, in some embodiments, the system can be configured to utilize as inputs one or more of: vessel boundaries in image plane; pixel estimates of tool position, tool orientation, and/or way point position in second image plane (e.g., a lateral view); registered 3D reconstruction of the anatomy; and/or the like.

Further, for inverse kinematics, in some embodiments, the system can be configured to utilize as outputs one or more of: desired motor positions for each of the actuators; change in motor positions; desired instrument configuration; and/or the like.

Generally speaking, forward kinematics maps motor positions to the expected position and orientation of the tool tip, while inverse kinematics does the reverse. In some embodiments, with simple articulated catheters, these functions can be analytically derived for simplified models. In some embodiments, this function is also configured to handle the conversion between image space (px for pixels below) and Euclidean space (standard xyz). For example, when there are two imaging planes and known camera calibrations, there is a one to one mapping between image space and Euclidean space. In some embodiments, the function can therefore convert the pixel information to Euclidean space before determining the desired motor positions. When there is only one imaging plane, there is a loss of information from Euclidean space to image space. In some embodiments, the simplifying assumptions of a preset depth and an instrument grounding on the patient bedside can be used to estimate the transformation from pixel space back to Euclidean space before the standard inverse kinematics can be used. Also, in some embodiments, the transformation from desired tip position to observed tip position is applied to the expected tip position, resulting in a relative desired tip position. This can mitigate some of the risk of the inverse kinematics being unable to reach an absolute position due to modelling errors.

Provided below is an example of pseudo code for inverse kinematics in single plane and dual plane:

```
def motion_planner_inv_kin(position_measured,
        heading_measured,
        incline_measured,
        position_desired,
        incline_desired,
        heading_set,
        incline_set,
        body_pts_measured):
    # compare desired to measured
    d_px = position_desired - position_measured
    heading_desired = atan2(d_px[1], d_px[0])
    change_in_heading = heading_desired - heading_measured
    change_in_incline = incline_desired - incline_measured
    # update set values based on change required
    heading_new = heading_set + change_in_heading
    incline_new = incline_set + change_in_incline
    # insertion based on angled changes
    insert_new = calculate_ins(change_in_heading,
        change_in_incline,
        body_pts_measured)
    # convert joint positions to motor positions
    desired_motor_positions = inverse_kinematics(insert_new,
            heading_new,
            incline_new)
    return desired_motor_positions
```

Similarly, for Jacobian, in some embodiments, the system can be configured to utilize as inputs one or more of: pixel estimate of the tool tip; estimate of the tool tip's orientation in the image plane; way point pixel location; actuator positions of device rotation and actuation; kinematic model of the instrument (part of function); and/or the like. Optionally, for inverse kinematics, in some embodiments, the system can be configured to utilize as inputs one or more of: vessel boundaries in image plane; pixel estimates of tool position, tool orientation, and/or way point position in second image plane (i.e. lateral view); registered 3D reconstruction of the anatomy; and/or the like.

Further, for Jacobian, in some embodiments, the system can be configured to utilize as outputs one or more of: desired motor positions for each of the actuators; change in motor positions; desired instrument configuration; and/or the like.

Generally speaking, the Jacobian is the derivative of the forward kinematics. When inverted, it provides a locally linear approximation to the inverse kinematics. In some embodiments, the system can be configured to iteratively calculate Jacobian to frequently update the locally linear approximation. In some embodiments, Jacobian behaves similarly as the inverse kinematics method above with respect to single and dual plane information. In some embodiments, with dual plane, Jacobian can convert the pixel information to Euclidean space, then use normal Jacobian inverse to get the desired change in motor positions. In some embodiments, in a single plane, Jacobian itself can include the pixel space to Euclidean space conversion as it can be approximated as a linear transformation.

Provided below is an example of pseudo code for Jacobian in single plane and dual plane:

```
def jacobian_px_single_plane(px_position,
        px_orientation,
        px_desired,
        motor_positions):
    # desired_px in tip frame
    px_desired_tf = Rz(px_orientation) * (px_desired - px_position)
    # J_p = dp/dx * dx/du
    # p(x) = 1/s K x
    # assumes similar (1/s) terms for x_1 and x_2
    # K is camera perspective matrix
    # J is standard jacobian dx/du
    J_px = (1 / s) * K * J
    return motor_positions + psuedoinv(J_px) * px_desired_tf
```

```
def jacobian_px_dual_plane(px_position_xy,
    px_orientation_xy,
    px_desired_xy,
    px_position_zy,
    px_orientation_zy,
    px_desired_zy,
    motor_positions):
tip_desired = inverse_persepective(px_desired_xy, px_desired_zy)
estimated_tip_position, estimated_tip_orientation = inverse_persepective(
    px_position_xy, px_orientation_xy, px_position_zy, px_orientation_zy)
# desired_px in tip frame
T_estimated_to_desired = get_transformation(
    tip_desired, estimated_tip_position, estimated_tip_orientation)
# get translation offset only
delta_tip_desired = T_estimated_to_desired[:3, 3]
# J is standard jacobian dx/du
return motor_positions + psuedoinv(J) * delta_tip_desired
```

Control Loop(s)

In some embodiments, each or some of the instrument control methods or algorithms, such as, for example, inverse kinematics, Jacobian, and/or others, may provide changes in motor position that may only be valid for a small distance. As such, to remain on track, the instrument control method(s) or algorithm(s) may need be updated with new feedback about the updated position and orientation of the tool. In some embodiments, the system may rely on human input to close this loop (open loop), or the system can be configured to close this loop itself (closed loop).

Figure 8A:
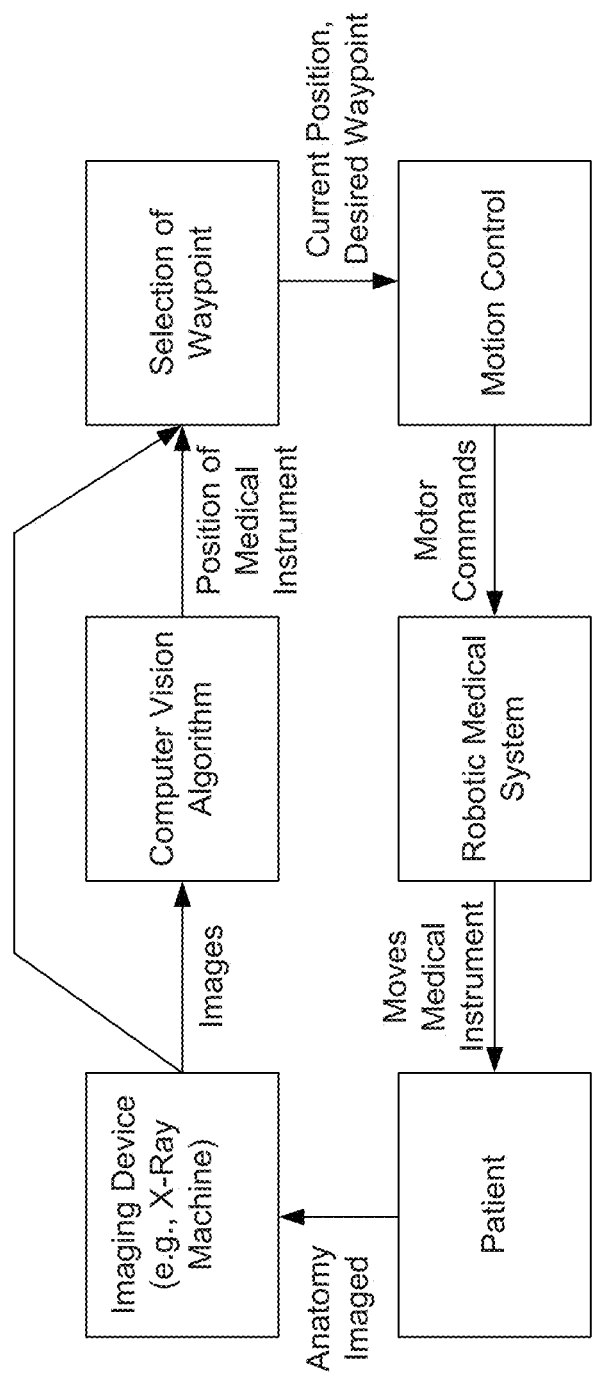
FIG. 8A illustrates an embodiment(s) of a control loop for teleoperation of robotic endovascular intervention.
Figure 8B:
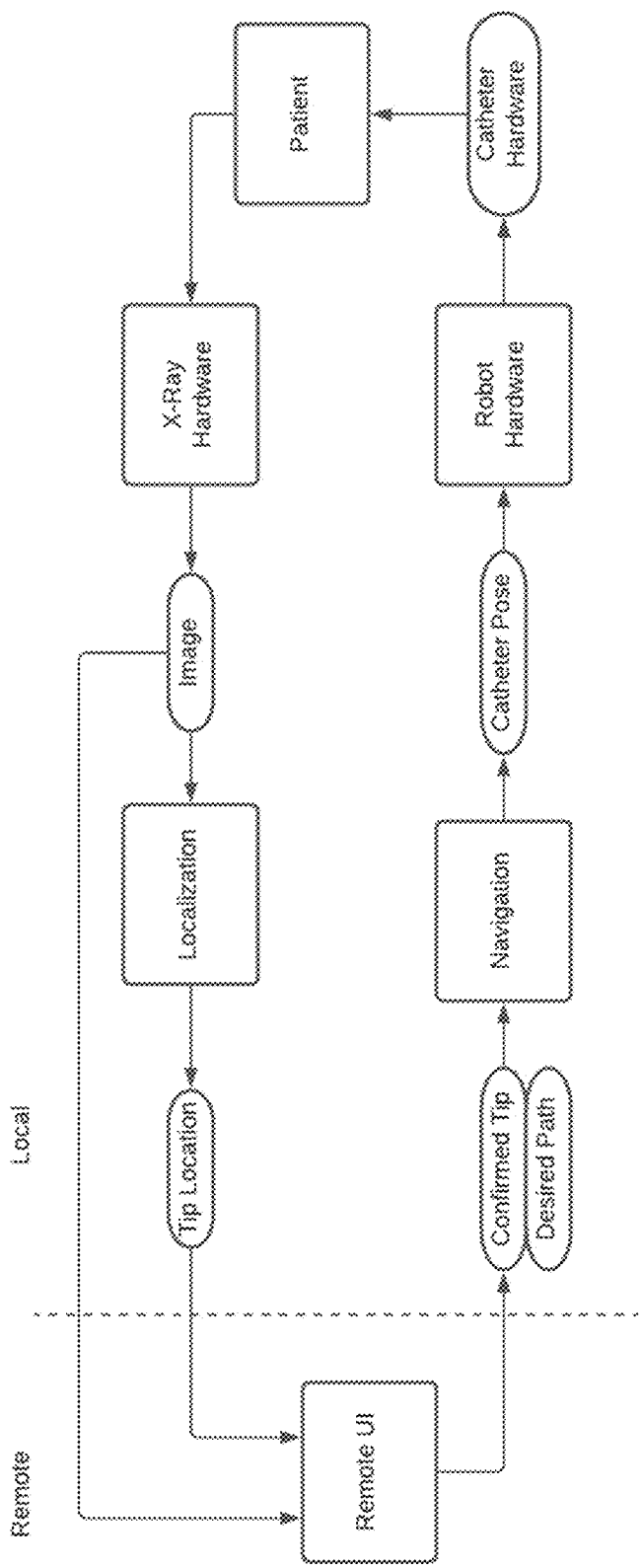
FIG. 8B illustrates an embodiment(s) of a control loop for teleoperation of robotic endovascular intervention.

FIGS. 8A, 8B, 9A and 9B each illustrate example embodiments of a control loop for teleoperation of robotic endovascular intervention. In some embodiments, when the px estimate of the tool tip is within a predefined radius of the way point, it stops, until a new way point is selected. More specifically, FIG. 8A illustrates an example control loop in which the motion control algorithm requires user feedback at every step, which can be referred to as an open loop control. FIG. 8B shows a control loop in which the user is involved it each iteration of the loop. In this example, image and tip information from the patient and localization are shown to the user, who then confirms their validity and indicates the next desired move.

Figure 9A:
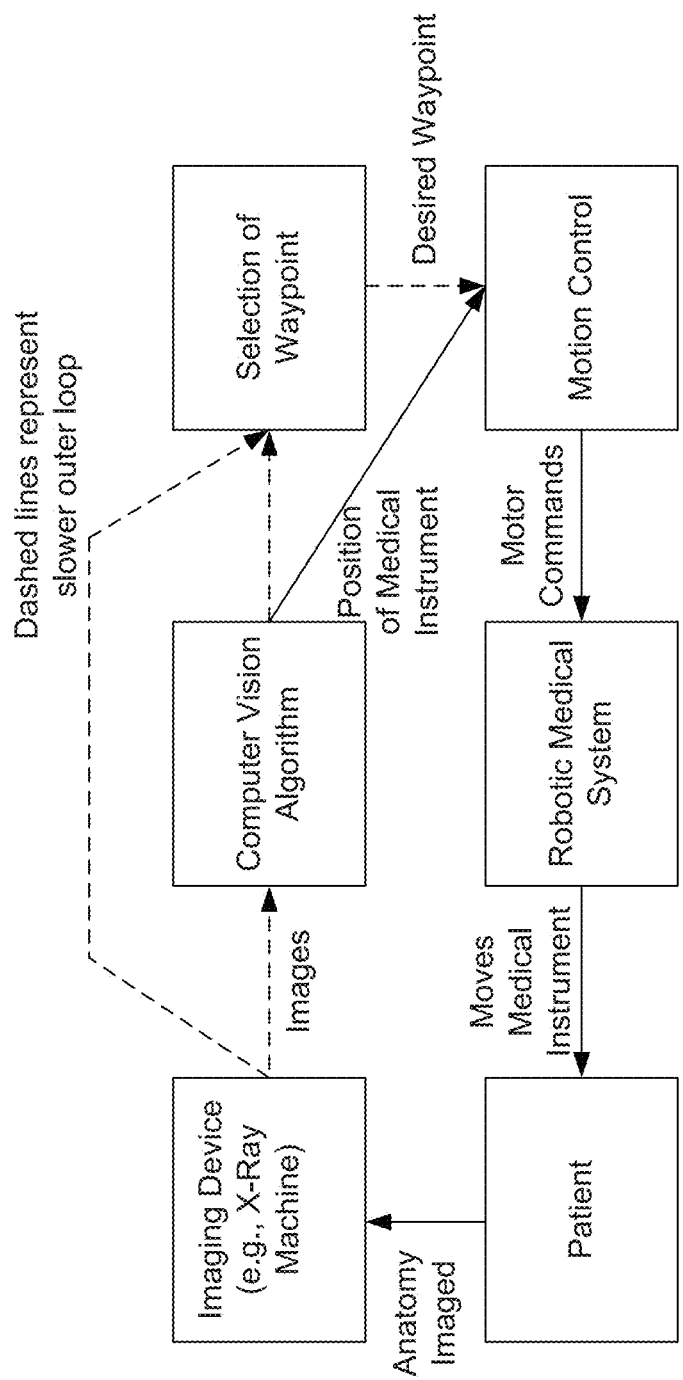
FIG. 9A illustrates an embodiment(s) of a control loop for teleoperation of robotic endovascular intervention.
Figure 9B:
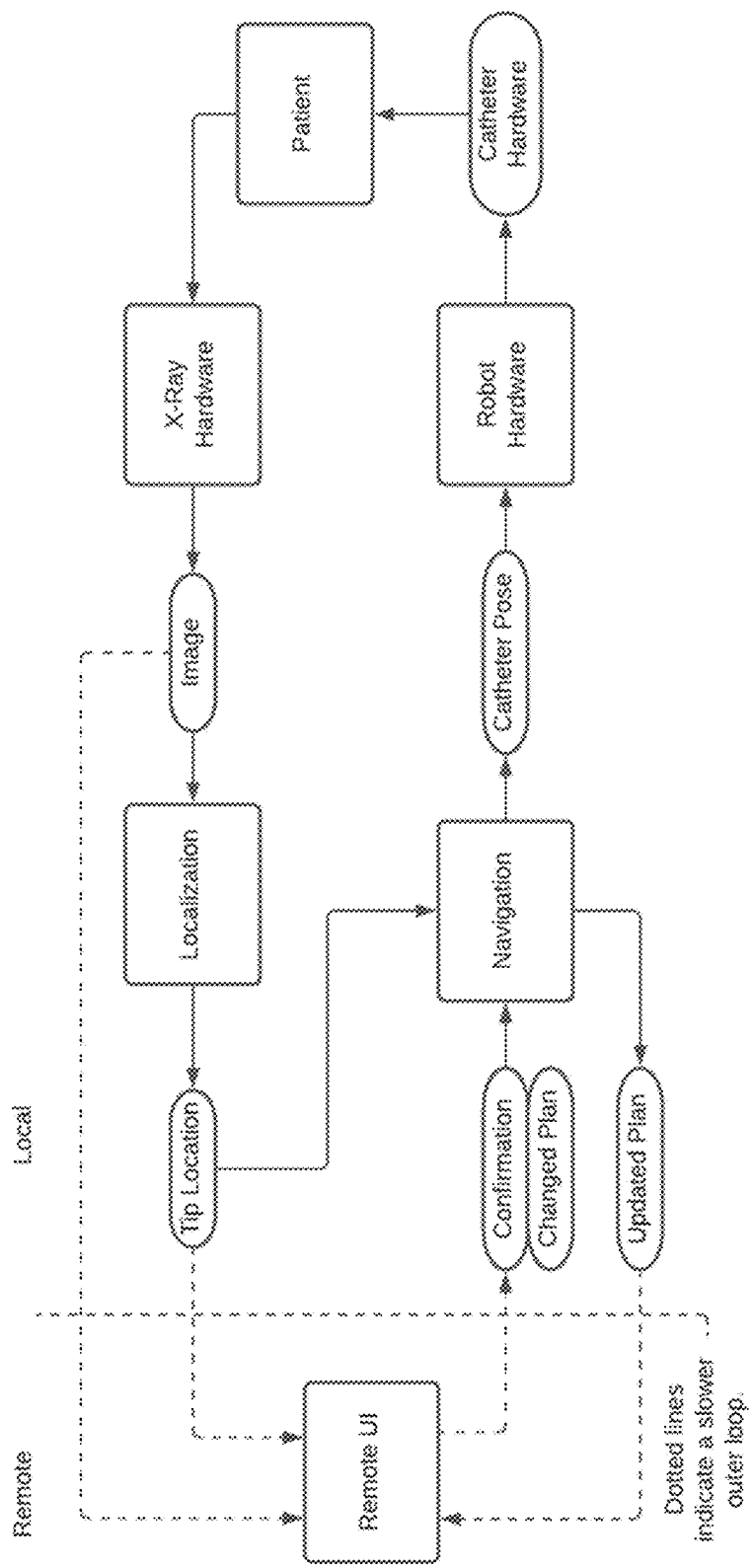
FIG. 9B illustrates an embodiment(s) of a control loop for teleoperation of robotic endovascular intervention.

FIG. 9A illustrates an example control loop in which the motion control algorithm does not require user feedback at every step. In the example embodiment illustrated in FIG. 9A, the system recalculates the motor commands with every update of the surgical tool location. In some embodiments as the one illustrated in FIG. 9A, the user may introduce new desired way points to update the motion control calculations. FIG. 9B illustrates an example control loop in which the motion control algorithm does not require user feedback at every step. In this embodiment, local tip information is used to recalculate the motor commands with every step. At a slower rate, the user can be asked to verify and/or change the plan that is being executed. In some embodiments, the control loops of FIGS. 8B and 9B can be implemented, for example, on or by the system of FIG. 7B.

Applications

In some embodiments, the systems, devices, and methods described herein can be used for one or more endovascular purposes, surgeries, and/or treatments. For example, in some embodiments, the systems, processes, and methods described herein can be used for one or more of removal of intravascular blockage/Reestablishment of perfusion; treatment of vessel wall injury (aneurysm and/or dissection); treatment of bleeding: aneurysm rupture/trauma; and/or the like. Moreover, in some embodiments, the systems, devices, and methods described herein can be used to treat vascular trauma.

In some embodiments, the systems, devices, and methods described herein can be used for neurovascular applications and/or treatments, such as for example to treat subarachnoid hemorrhage, aneurysm, arteriovenous malformation, and/or the like. In some embodiments, the systems, devices, and methods described herein can be used for cardiovascular applications and/or treatments, such as for example to treat myocardial infarction, coronary artery disease, pacemaker insertion, and/or the like. In some embodiments, the systems, devices, and methods described herein can be used for aortic applications and/or treatments, such as for example to treat aortic dissection, aortic aneurysm, and/or the like. In some embodiments, the systems, devices, and methods described herein can be used for peripheral emboli applications and/or treatments. In some embodiments, the systems, devices, and methods described herein can be used for vascular trauma applications and/or treatments. In some embodiments, the systems, devices, and methods described herein can be used for venous applications and/or treatments, such as for example to treat pulmonary embolism, deep vein thrombosis, and/or the like.

Image Space Control—Vessel Centerline Extraction and Path Auto-Generation

In some embodiments, the system can be configured to extract one or more vessel centerlines from a medical image, such as an x-ray image, and/or automatically and/or dynamically generate a recommend path from the current location of the catheter to the desired location based at least in part on the extracted one or more vessel centerlines.

Figure 11:
FIG. 11 illustrates an embodiment(s) of image space control of a system and/or method for robotic endovascular intervention as applied to an example vasculature.

In particular, in some embodiments, a key component of image space control of catheters in arterial vessels or other vasculature can comprise identifying the path between the current catheter location and the final desired location. For example, FIG. 11 illustrates an embodiment(s) of image space control of a system and/or method for robotic endovascular intervention as applied to an example vasculature. In the example illustrated in FIG. 11, the goal of the user is to move to catheter, the distal tip of which is identified by the orange circle, to the goal location, which is depicted by the cyan diamond.

In some embodiments, the system can be configured to allow a user to specify a desired path from the location of the catheter to the goal location. In some embodiments, the system can be configured to provide assistance to the user in delineating the path from the location of the catheter to the goal location. That way, in some embodiments, the system can make the process of image space control safer and/or simpler. In some embodiments, for the system to generate this path, it must understand the anatomy, such as, for example, the anatomy relating to the vasculature. In some embodiments, the system requires some critical anatomical information for path planning as described in more detail herein. Further, in some embodiments, the system is configured to dynamically extract certain anatomical information from sensor readings. In some embodiments, the extracted anatomical information can be used by the image space controller for path planning.

In particular, in some embodiments, the system can comprise and/or be configured to access certain information related to the relevant vasculature in assisting the user to find an anatomically feasible path from the catheter location to the goal location. In some embodiments, such information or data can be stored on a local and/or remote database that is accessible by the system.

Figure 12:
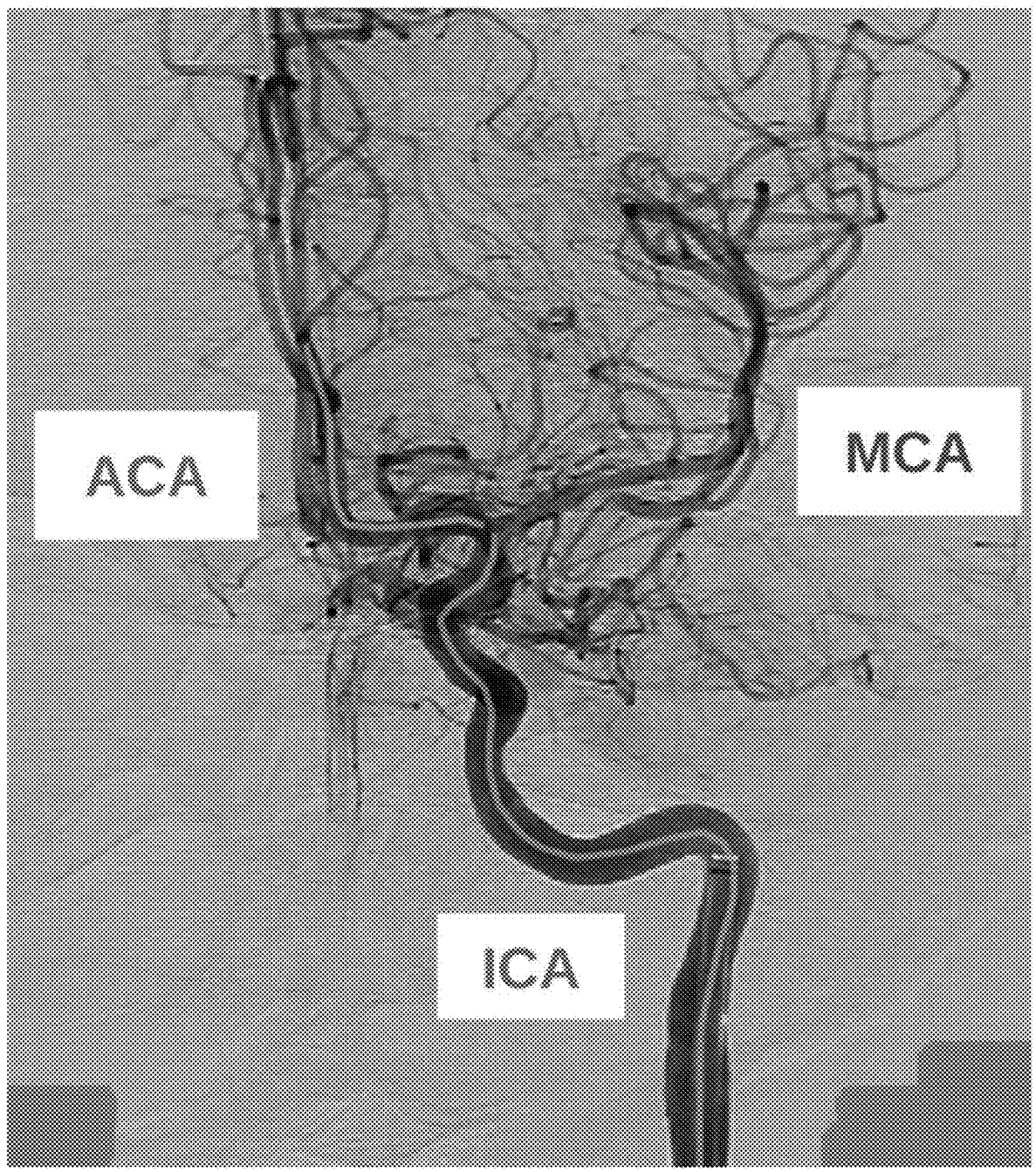
FIG. 12 illustrates an example image of a vasculature and relevant anatomical information that can be used by an embodiment(s) of a system and/or method for robotic endovascular intervention.

FIG. 12 illustrates an example image of a vasculature and relevant anatomical information that can be used by an embodiment(s) of a system and/or method for robotic endovascular intervention. As illustrated in the example of FIG. 12, in some embodiments, the relevant vasculature can include the internal carotid artery (ICA), which branches into the anterior cerebral artery (ACA) and the middle cerebral artery (MCA).

In the illustrated example of FIG. 12, in some embodiments, the information or data related to the relevant vasculature accessed by the system can include one or more centerlines along the vasculature, such as for example centerlines of the ICA, ACA, and/or MCA. The centerlines can be, for example, paths or sequences of points along the middle of a vessel. In some embodiments, the centerlines can implicitly provide information to the system about vessel junctions or where vessels coincide. In some embodiments, the width of the vessels is not required for image space control by the system, and therefore the system can be configured to ignore or not analyze width information in generating a pathway. In some embodiments, the system can be configured to analyze width information in generating a path. In some embodiments, In some embodiments, in order to extract the vasculature information, the system can be configured to identify from the sensor readings one or more vessel centerlines, such as for example centerlines of the ICA, ACA, and/or MCA in the illustrated example of FIG. 12 and/or any other vessel. In some embodiments, the sensor readings can comprise any medical image, such as for example an x-ray image, MRI, CT, and/or the like. In some embodiments, the system can be configured to utilize a function $f(x) \to y$ to map one or more input medical images (x), such as an x-ray image, to one or more vessel centerlines (y).

The system can be configured to utilize one or more functions to determine the centerline of vessels. For example, in some embodiments, the system can comprise and/or be configured to access code with pre-defined rules for identifying centerlines, such as for example centerlines of the ICA, ACA, MCA and/or any other vessel. In some embodiments, the system can comprise and/or be configured to utilize one or more machine learning algorithms to automatically and/or dynamically identify one or more vessel centerlines from medical image data. A machine learning approach can be advantageous in that the system may be able to learn non-trivial statistical patterns directly from the data itself, thereby allowing the system to identify vessel centerlines despite the high variation and ambiguity in medical images, such as for example x-ray images.

As such, in some embodiments, the system can be configured to utilize one or more machine learning algorithms or models to learn the function $f_\theta$, in which the system is configured to automatically learn the parameters $\theta$ from data, such as for example medical image data.

In particular, in some embodiments, the system can be configured to utilize one or more deep neural networks. Deep neural networks can be advantageous in some instances due to the fact that the inputs (such as x-ray images) and the outputs (such as labeled centerlines or centerlines) can be high dimensional. In some embodiments, the system can be configured to utilize one or more convolutional neural networks (CNNs) to automatically and/or dynamically identify vessel centerlines from an input medical image, because the input modality is an image.

Figure 13:
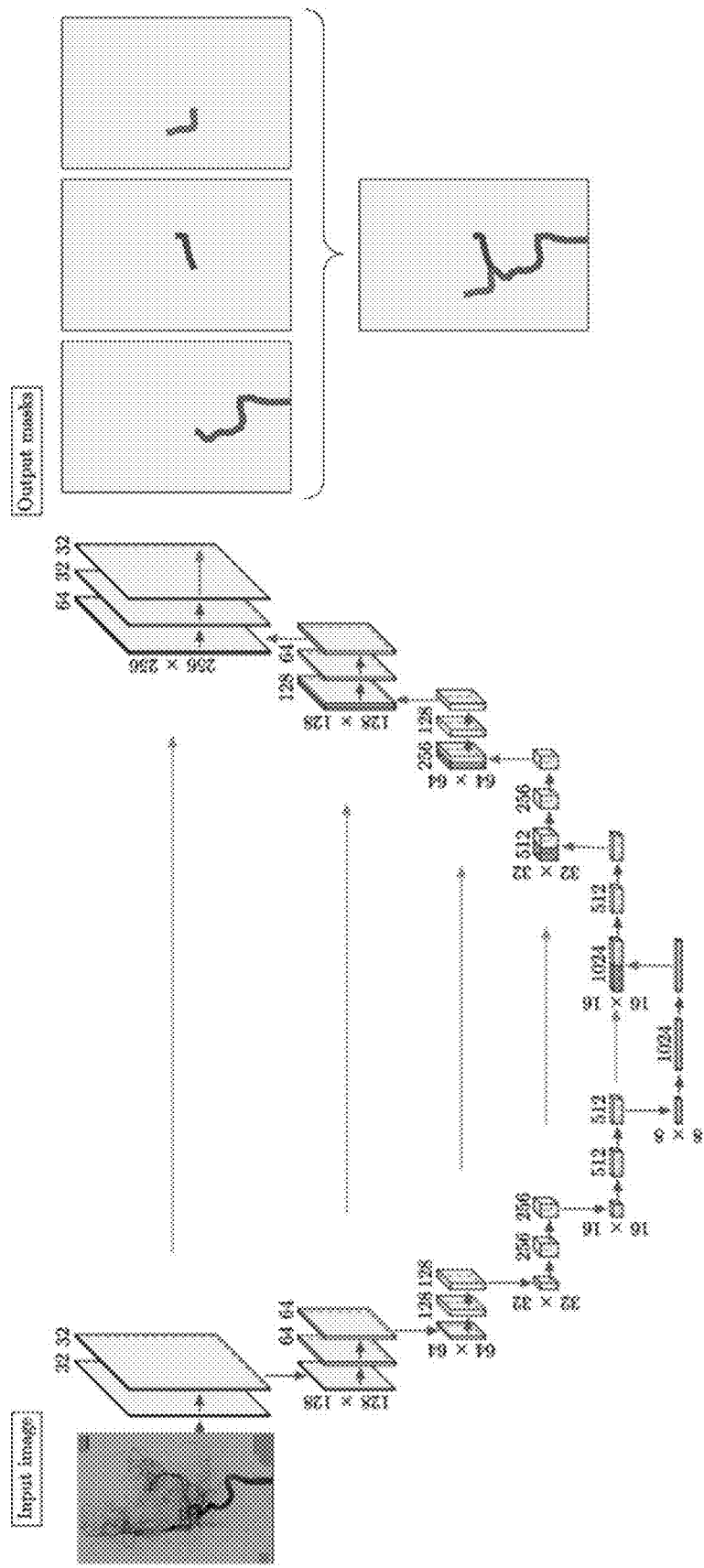
FIG. 13 illustrates an example embodiment(s) of a convolutional neural network (CNN) that can be used by an embodiment(s) of a system and/or method for robotic endovascular intervention.

In some embodiments, the machine learning model, such as a CNN, can be configured to directly output labeled centerlines. In some embodiments, the machine learning model, such as a CNN, can be configured to output one or more intermediary outputs rather than directly outputting labeled centerlines. In some embodiments, such intermediary or indirect approach can be advantageous, because each centerline can have a different number of constituent points and CNNs or other machine learning algorithms may not easily cope with outputs with varying dimensions. As such, in some embodiments, the system can be configured to utilize one or more CNNs or other machine learning algorithms, in which the one or more CNNs or other machine learning algorithms can be configured to predict L+1 images, where each image can correspond to a specific vessel label (such as ICA, ACA, MCA, and/or the like) and each pixel in that image can correspond to the probability that that pixel in the medical image (such as an x-ray image) contains a vessel of that label. By utilizing such formulation, in some embodiments, the one or more CNNs or other machine learning models only need to deal with a fixed-dimensional output, which can be easier to handle. In some embodiments, the system can be configured to utilize one or more such formulations or other architecture for semantic segmentation, which can be configured to predict a corresponding label of each pixel in a medical image given an input medical image. For example, in some embodiments, the system can be configured to utilize a U-Net CNN, such as the one illustrated in FIG. 13.

In some embodiments, the system can be configured to first train a machine learning model, such as a CNN, to predict vessel segmentations s. In some embodiments, the machine learning model can be trained using a plurality of labeled vessel segmentations. More specifically, in some embodiments, the system can be configured to convert one or more labeled centerlines y into segmentations s. That way, in some embodiments, the centerlines can be converted into lines of a fixed width. In some embodiments, the system can then label the corresponding pixels which overlap with such lines.

In some embodiments, given the input images x and vessel segmentation images s, the system can be configured to train the neural network parameters $\theta$ by minimizing the distance between the ground truth segmentations s and the predicted neural network segmentations $\hat{s}$, as depicted by:

$$\min_\theta \sum_{(x,s)} \text{distance}(\hat{s}, s): \hat{s} = f_\theta(x)$$

In some embodiments, the above-identified minimization is performed using minibatch stochastic gradient descent.

In some embodiments, the system can be configured to map the inputted x-ray image x to the predicted labeled vessel centerlines ŷ. In some embodiments, the system can be configured to utilize one or more neural networks or other machine learning algorithms to map the x-ray image to the predicted segmentation: $f_\theta(x) \to \hat{s}$. In some embodiments, the system is further configured to convert the predicted segmentation ŝ into the labeled vessel centerlines ŷ. For example, in some embodiments, the system is configured to utilize a skeletonization algorithm to find one or more centerlines in the segmentation image.

In some embodiments, the system is configured to receive user input that specifies the path from the current catheter location to the goal location. For example, in some embodiments, the user can click on a sequence of points on a user interface displaying a medical image of the vasculature, in which the sequence points can start at the current location of the catheter and end at the desired goal location.

In some embodiments, the system can be configured to streamline this process by complete and/or partial automation as described herein. In some embodiments, the system can be configured to identify and/or derive one or more labeled vessel centerlines using one or more techniques described herein, such as for example by utilizing one or more x-ray images or other medical images of a subject and/or one or more trained neural networks or other machine learning algorithms. In some embodiments, the system can be configured to utilize such centerlines to aid and/or automate the path generation process.

In particular, in some embodiments, the system can be configured to assist the user in placing one or more waypoints, for example using the system's knowledge of one or more vessel centerlines. More specifically, in some embodiments, as the user specifies the path on a user interface by clicking on a sequence of points, for example on a displayed medical image of the vasculature, the system can be configured to automatically "snap" the user's click points onto the vessel centerline or otherwise require or ensure that the user inputted points are on the vessel centerline. In some embodiments, such automatic snapping can have at least two advantages. First, in some embodiments, automatic snapping or otherwise requiring the user-inputted points to be on the vessel centerline can increase the safety of the system by ensuring the catheter does not attempt to move outside of a vessel. Second, in some embodiments, automatic snapping or otherwise requiring the user-inputted points to be on the vessel centerline can enable the user to more quickly specify the path because the user-inputted points do not all have to be as precise.

In some embodiments, the system can be configured to automatically and/or dynamically propose to the user via a user interface one or more subsequent points or waypoints on the path to click on. In some embodiments, in addition to the advantages listed above, this approach can also have the added advantage of decreasing the cognitive load of the user, especially if the doctor or user is remotely located.

In some embodiments, the system can be configured to automatically and/or dynamically generate the path from the current location of the catheter to the goal location. As such, in some embodiments, the system can be configured to provide autonomous path generation for implementation of an autonomous catheter robot. In particular, in some embodiments, the system can utilize data and/or knowledge of the labeled vessel centerlines to automatically generate the path to the goal location. In some embodiments, the system can be configured to receive a desired goal location of the catheter from user. As a non-limiting example, a doctor may examine a CT scan or other medical image of a stroke patient and determine that a clot is in the left MCA and select a location in the left MCA as the desired goal location on a user interface.

In some embodiments, the system can determine the sequence of vessels the catheter must navigate through based at least in part on the current catheter location and the goal location. In order to determine the sequence of vessels, in some embodiments, the system can be configured to utilize a hand-specified roadmap of the vessel anatomy, which can include data or information relating to which vessels are adjacent to one another. In some embodiments, using this roadmap, the system can determine which vessels it should navigate through to reach the goal.

Figure 14:
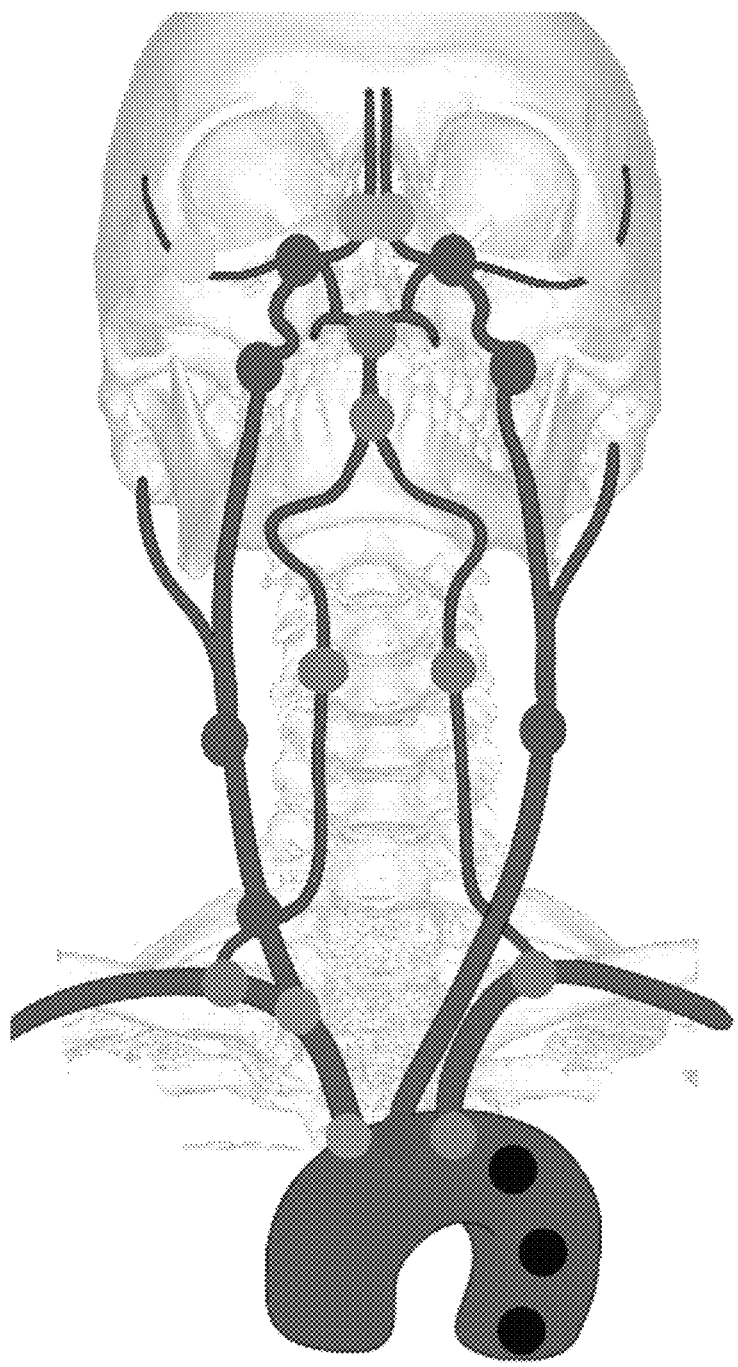
FIG. 14 illustrates an example vessel roadmap that can be used by an embodiment(s) of a system and/or method for robotic endovascular intervention.

FIG. 14 illustrates an example vessel roadmap that can be used by an embodiment(s) of a system and/or method for robotic endovascular intervention. In the example illustrated in FIG. 14, each colored circle corresponds to a specific vessel. In some embodiments, many or most vessel roadmaps will be the same and/or will include similar features between different patients. In some embodiments, there can be some anatomical differences among vessel roadmaps of different people, such as for example the branching at the aorta among others. In some embodiments, the system can be configured to analyze subjects with specific vessel roadmaps that are pre-screened or pre-identified. In some embodiments, the system can be configured to automatically analyze and/or identify subjects with varying vessel roadmaps and/or features thereof.

In some embodiments, the system can be configured to automatically and/or dynamically generate a path from the current catheter location to the desired goal location using one or more vessel roadmaps, which can be patient specific and/or generally applicable. In particular, in some embodiments, the system can be configured to determine the current location of a catheter based on an input medical image, such as an x-ray image of the vasculature. In some embodiments, the system can also be configured to identify and/or generate one or more labeled vessel centerlines based on the input medical image, for example using a trained neural network or other algorithm. In some embodiments, the system can determine which vessel the catheter is currently in. In some embodiments, using this vessel label as the starting point, the system can be configured to determine what subsequent vessels the catheter should navigate through using the roadmap. In some embodiments, the system can be configured to combine these planned subsequent vessels to form a single list of one or more waypoints, which the catheter will follow to reach the goal location. In some embodiments, this procedure or technique or one or more processes thereof can be constantly performed throughout the surgery until the catheter successfully reaches the goal location. In some embodiments, to account for any unseen complications, the system can be configured to allow a user to manually specify and/or modify the desired path and/or one or more waypoints along the desired path.

Safety System(s) and Method(s): Confirmation, Heartbeat, and Data Integrity and Clinical Monitoring As noted previously, the systems, methods, and devices described herein can be configured to perform teleoperation of robotic endovascular intervention where a remotely-located physician controls a robotic system that is local to the patient. Communication between the remotely-located physician and the robotic system can occur over a computer network, such as the internet, for example. Accordingly, it can be important to ensure that data pathways between the various components of the system (e.g., the remote and local components) are flowing in a timely manner in order in ensure that the system can be operated safely. As described in this section, in some embodiments, a primary mechanism for safety of the system can include a series of methods configured to verify that each piece of the system is operational and the data pathways are flowing in a timely manner. In this section, this series of methods is broken into three categories that each address different aspects of the system. The categories can include confirmation, heartbeat, and data integrity, each of which are discussed in more detail below. Although these three categories (confirmation, heartbeat, and data integrity) are described as an example in this section, other breakdowns of the safety protocols and methods are also possible. As such, the description of these three categories should not be construed as limiting this disclosure.

The first category to be discussed is confirmation. As used herein, confirmation can refer to local verification of the data presented to a remote operator that lead the remote operator to command a tool motion prior to execution of the command. In this way, confirmation can provide a primary safety mechanism that can be configured to ensure safe operation (e.g., teleoperation of a robotic system) across a remote network, such as the internet. In general, the most dangerous part of any robotic procedure occurs when the robotic system is moving a tool, such as a catheter, within the patient. If such movements are not correctly determined, injury to the patient can occur. The internal motion planning algorithms described throughout this disclosure have been verified and are safe, but ultimately and in some embodiments, during a procedure the goal or target of a commanded robotic motion comes from the user or physician remotely controlling the robotic motion. For example, as described above, the system can robotically move a tool, such as a catheter, according to waypoints selected or determined by the user as aided by the system. Thus, it can be imperative that the user is presented valid and timely information regarding the state of the system. For example, if the user does not correctly understand the current position and orientation of a robotic tool, the user may provide improper command inputs that can cause damage or injury to the patient.

Accordingly, in some embodiments, during use of the systems, method, and devices described herein, when a decision is made (for example, by the physician) as to what the next motion for the tool should be and confirmed by a button press or hold, then indicators of all the information the user was presented and the desired motion can be sent back to the system. This information and the commanded desired motion can then be verified locally to ensure that information the user was presented with still matches the current state of the system. This can done, for example, with both time and position. If, locally, it is determined that there has been little or no change in the data, then the system can forward the motion command onto the robot for execution. If, locally, it is determined that the data shown to the remote user is not deemed to be sufficiently accurate, for example, either in time or position, the system may determine that the commanded motion should not be executed and the commanded motion can be dropped.

In some embodiments, the system can be configured to drop such commands until a max number or threshold (or a maximum time) of commands is dropped. Once this threshold is exceeded, the system may enter into a fault state until the issues clear up or are dealt with by the user.

In some embodiments, data being off in time can be indicative of latency or a stuck algorithm. In some embodiments, data being off in position can indicate buffering or external influence. Regardless of the cause of the problem, the system can be configured to wait for new information to be presented to the user and confirmed before proceeding.

The second category to be discussed is heartbeat. As will be described in more detail below, the systems, methods, and devices described herein can include or be configured to communicate with a heartbeat system that can be configured to ensure that a next command received by the system from the remote operator has a sufficiently high probability of succeeding. In some embodiments, the heartbeat system can do this by monitoring each component of the system and verifying that it is in operation and responding in a timely manner. In this way, the next command sent to that component should be handled as expected. If any component stops responding, the system can be configured to stop operation, put the system into a safe state, and/or inform the user to take an appropriate action to resume operation. This can avoid getting into a potentially hazardous situation when components are not operating at peak efficiency. In some embodiments, the general mechanism for achieving this with the heartbeat system can include sending small amounts of information between a monitor and each component of the system. These small amounts of information can be verified to ensure that that information is being processed and returned in a timely manner.

In some embodiments, the Heartbeat system can be further broken down into two distinct subsystems, a remote system and a local system. The remote system can be configured to determine and understand the reliability of information that is being sent outside of the local network, for example, information sent over a large network such as the internet. This can be important because, for some instances of teleoperation, information must be sent over network (e.g., the internet) that are not fully within the control of the system. In contrast, the local system can be configured to verify communication within the on-premises robotic hardware. Since these communications are co-located the communications mechanism can be made much more reliable than those going outside the hospital. Thus, in some embodiments, much less effort need be spent on verifying the communication channel and much more spent on the timely operation of the component in question.

The third category to be discussed is data integrity and clinical monitoring. This category can refer to safety checks and verifications that relate to the functioning of the system itself. For example, data integrity and clinical monitoring can verify whether the system is accurately performing the commanded motions and/or whether the commanded motions themselves are in fact proper. In some embodiments, such data integrity and clinical monitoring can rely on the confirmation and heartbeat systems discussed above. When those mechanisms are functioning properly, the system can now start to determine the more complex safety related questions involved in data integrity and clinical monitoring.

For example, in some embodiments, along with each heartbeat, the system can send data about the functioning of the application or data stream. This information may be highly dependent on the application or clinical embodiment itself. For example, if the data is expected to be periodic, the system may include a timestamp related to a last update. This could show more than a raw heartbeat in that the heartbeat, in general, only provides an indication that the system is in communication with the component in question. The addition of this last update timestamp implies knowledge of what that component is expected to be doing, and can determine that the component it is actually doing its intended job. Similarly, as another example, if a catheter tip is located outside of detected vessels this may indicate a problem with our detection algorithms, but only in cases that are expected to be in the vessels.

Figure 15:
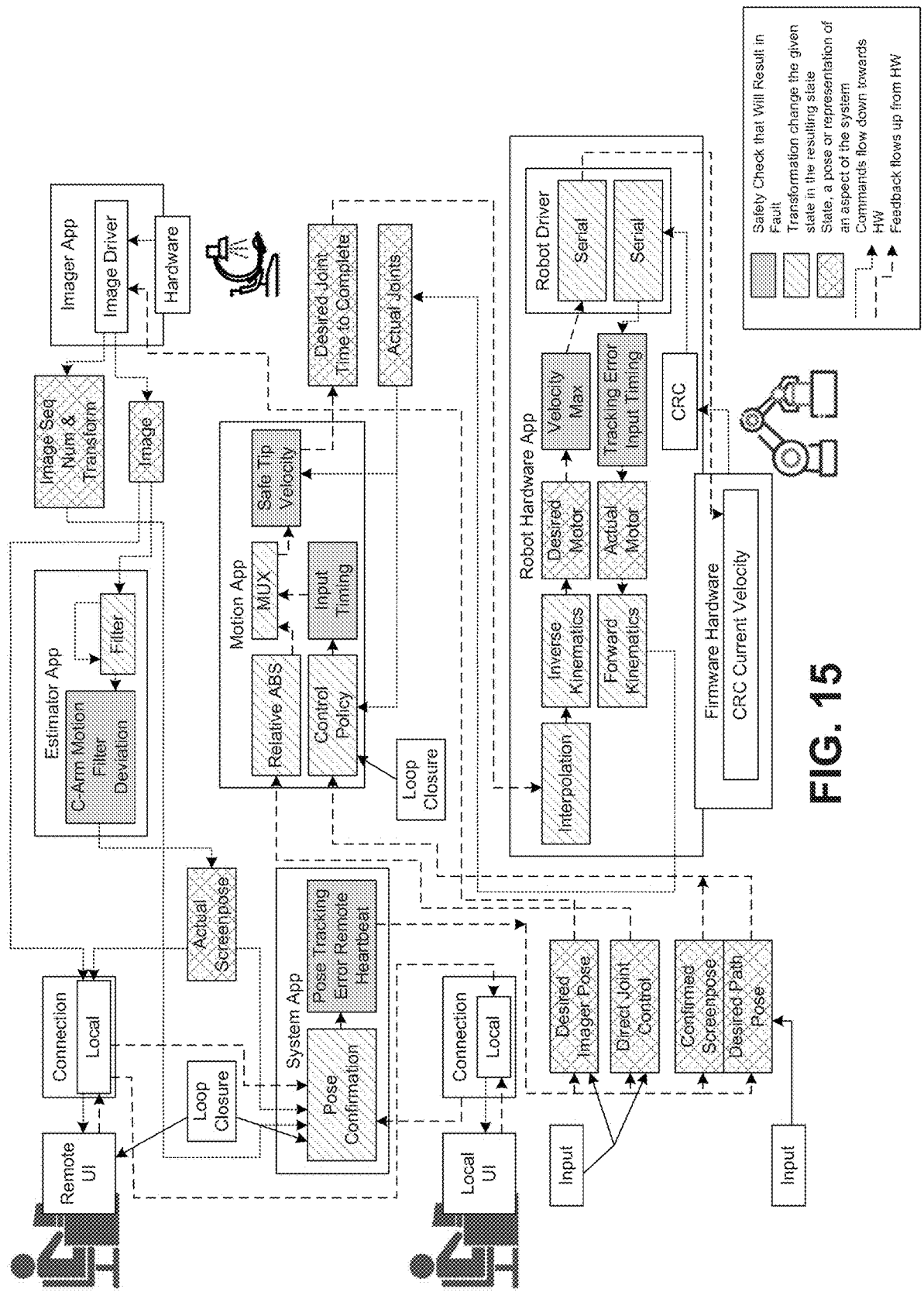
FIG. 15 is a block diagram illustrating an embodiment(s) of a closed control loop for a system and/or method for robotic endovascular intervention.

Various examples will now be described in more detail to more fully provide an understanding of confirmation, heartbeat, and data integrity and clinical monitoring. As noted above, these examples are provided by way of illustration, not limitation. FIG. 15 provides an example system that implements these features.

In some embodiments, the goal of confirmation is to track and verify that the information that was presented to the remote user (and that was relied upon in making a decision to execute a command) matches the current state of the system before executing a command. In some embodiments, an initial step in performing such a confirmation can be tagging data, for example, the data shown to the user which is relied upon in making a decision, with unique identifiers. By way of illustration, an example of confirmation for image space control will be described with reference to FIG. 16. In some embodiments, for image space control, the information shown or displayed to the remote user can include, for example, an image from the x-ray hardware application (or other imager), the tool tip (tip) from the localization application (estimator), and any updates made to the goal tip location (updated path) suggested by the navigation application (motion planner).

Figure 16:
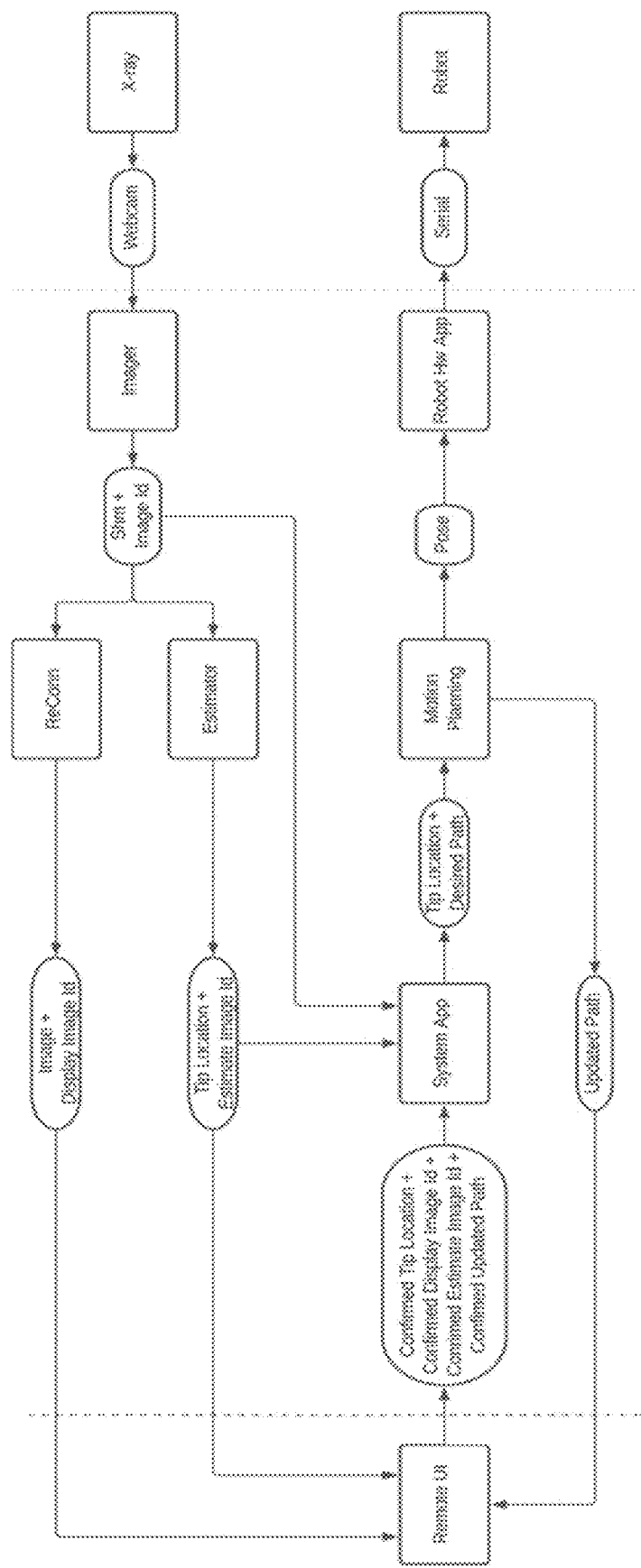
FIG. 16 is a block diagram illustrating an embodiment(s) of a control loop for a system and/or method for robotic endovascular intervention.

As shown in FIG. 16, in some embodiments, when an image is received from the imager, it can be sent, for example, via shared memory, to two different applications, the estimator and a remote connect application (ReConn). Across the shared memory channel a unique identifier, for example, a unique (counting) 4-byte integer, can be attached to the image. At 30 frames-per second (fps) such a unique identifier would not repeat for 4.5 years, and thus can be considered to be sufficiently unique. In other embodiments, other unique identifiers can be used. With continued reference to FIG. 16, the estimator can attach this unique identifier to its result. The ReConn can send the image and the unique identifier over the remote network to the remote UI. It is not trivial to directly couple a number (the unique identifier) with the compressed image data sent to the remote UI. Accordingly, an encoding scheme has been designed that is resilient to compression. This encoding scheme will be discussed below with reference to FIGS. 18 and 19. Although a particular example encoding scheme is shown and described with reference to these figures, other schemes are also possible and may be used in some embodiments. With continued reference to FIG. 16, the remote UI can then decode this number (the unique identifier) and send it back with the updated command, goal, or path.

In the illustrated example of FIG. 16, the estimator can be responsible for turning an image into an estimated tip location. In some embodiments, this is accomplished through machine learning or other artificial intelligence algorithms as described above. In some embodiments, as a component of confirmation, this estimate can be shown to the user before the system proceeds to move the robot according to an issued command. A potential issue is that, in some embodiments, the user will need to see this tip location along with the image that was used to create it, but the images may come in along a different low latency channel. Advantageously and to address this potential issue, in some embodiments, the system may use the fact that images generally change very little over short amounts of time, such as the 20-30 frames per second, at which the system sends the images. Accordingly, the system can attach the unique id of the image used to make the tip estimate so that later it can verify that it was in fact close to the raw image displayed to the user and relied upon in making a decision.

With continued reference to FIG. 16, an updated path can be sent from the motion planner to the remote UI. The user can confirm or adjust this path, then the new path and goal can be sent back along with tip confirmation. In some embodiments. the motion planner does not use any previous path information when generating motions. This can mean that the system will simply pass the entire path information along with the command and confirmation.

In some embodiments, the safety systems and methods described in this section can provide a gateway to motion by, for example, performing certain functions or verifications before executing any commanded motions. For example, in the example of FIG. 16, this gateway to motion can be performed by the system application (system app). The system application can act as a gateway to the pipeline that will eventually result in motion. Besides confirmation, the system application can also utilize the heartbeat and data integrity features mentioned above and described in more detail below. These systems can supersede this, and commands can be stopped before they are allowed into the portion of system that results in motion if any component is out of place.

Figure 17:
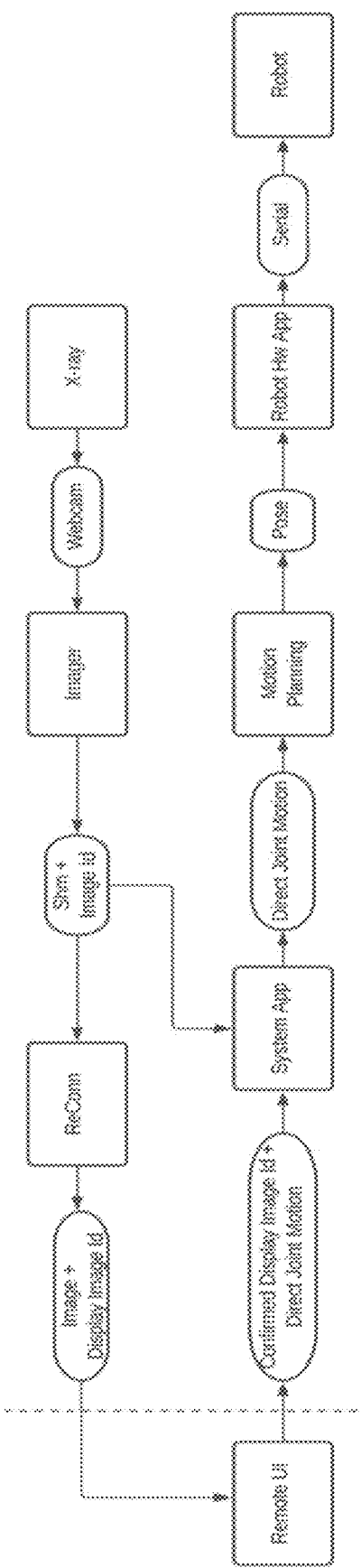
FIG. 17 is a block diagram illustrating an embodiment(s) of a control loop for a system and/or method for robotic endovascular intervention.

With continued reference to FIG. 16 and also with reference to FIG. 17, for the purpose of confirmation, the system application can have access to, for example, and without limitation, any or all of the following information: a raw mage ID (e.g., the latest ID produced by the imager); a local estimate (e.g., the local estimated tip location (for example, as determined by the estimator) and/or the local estimated image ID (for example, the image ID associated with the estimate); and/or information displayed to the remote user, which can include, for example, a remote tip location (e.g., the estimated tip (or user defined tip) that was last shown to the user), the remote estimated image ID (e.g., the image ID associated with the tip shown to the user), the remote display image ID (e.g., the raw image last shown to the user) and/or the confirmed path (e.g., a new goal and path that the system will be following).

In some embodiments, the system app can use the raw image ID as the current image from the hardware. The heartbeat and data integrity features can ensure that data is current and accurate.

The system app can be configured to verify the one or more of the following, among other things, to confirm the tip shown to the user. The system app can verify that the display image matches the tip location. For example, first, the system can check that it showed an image and tip that were close together in time. Since the Heartbeat mechanism can verify images are being processed at regular intervals, the system can take the difference between the remote estimated Image ID and the remote display image ID and verify this is below a safe threshold. Additionally or alternatively, the system app can verify that the display image is current. For example, in a similar manner the system can verify that the image it showed the user is current by taking the difference between that and the raw image ID. Again, the heartbeat mechanism can, in some embodiments, verify that the raw image ID is current. Additionally or alternatively, the system app can verify that the tip location is current. For example, the difference between the local estimated image ID and the remote estimated image ID can be used to determine that the system is using estimates within close temporal proximity, using the logic from the first two checks. Additionally or alternatively, the system app can verify the tip location position. For example, the difference between the local estimated tip location and the remote tip location can be used to determine that the tip has not physically moved a great distance during the confirmation process. If there is a large change the system may not propagate motion and can give the user time to confirm again after the new position has propagated remotely.

In some instances, since the system received the current path from the user along with confirmation and this path is generated through the user, the path can be forwarded when the tip is confirmed.

In some embodiments, the above can be optimized because the system has confirmed that the remote tip location and the local estimated tip location are in safe spatial proximity to be considered equivalent, and the local estimated tip location is more recent, the system can forward the local estimated tip location to the motion planner to use for its next motion calculation.

With reference to FIG. 17, a direct joint drive mode can be provided where the user directly tells the system which direction it would like to move each degree of freedom of the catheter or other tool. This can be considered a simplified subset of image space control where the user only needs the display image as input as shown in FIG. 17. Thus, in these examples, the system (e.g., the system application) may only verify that the display image ID is current before it forwards the command on to rest of the system.

As mentioned briefly above, an encoding scheme has been designed that is resilient to compression and that is configured to couple a number (e.g., as the unique identifier) with a compressed image data sent to the remote UI. This encoding scheme will be discussed below with reference to FIGS. 18 and 19.

On the local system (e.g., internally) it is generally simple to pass around a unique identifier with each image. For example, this can be done by simply by allocating 4 extra bytes with each image in shared memory and passing a monotonic counter as a unique image ID. While there are good data channels that go out to the remote machine, these are not directly coupled with the channel supplying the image, and the proximity to the stream is insufficient. Accordingly, it has been determined that an advantageous way make sure the information sent with the image is received is to encode it in the stream directly. In some embodiments, the stream the system sent across to the remote system is compressed. Because of this, if the system simply encodes the bits as bytes in the image, the encoded information is lost to compression. Thus, the following encoding scheme has been developed to encode the number in the image.

First, the unique image id can be encoded as a six-digit base-four number. For example, any digits larger than five or six can be dropped. At 30 FPS, this will cause the numbers to repeat every 2 minutes and 15 seconds (34 seconds at 5), but that is, in some embodiments, is orders of magnitude past the heartbeat rates used by the system and thus is well below the Nyquist limit. As one specific example, Example 6687% 4096=2591→base-4→220133.

Next, each digit is converted into grey scale pixel value between 0 and 255 by multiplying each digit by 64. As one specific example, 220133→(128), (128), (0), (64), (192), (192).

Figure 18:
FIG. 18 illustrates a gray scale encoded identifier according to an embodiment.
Figure 19:
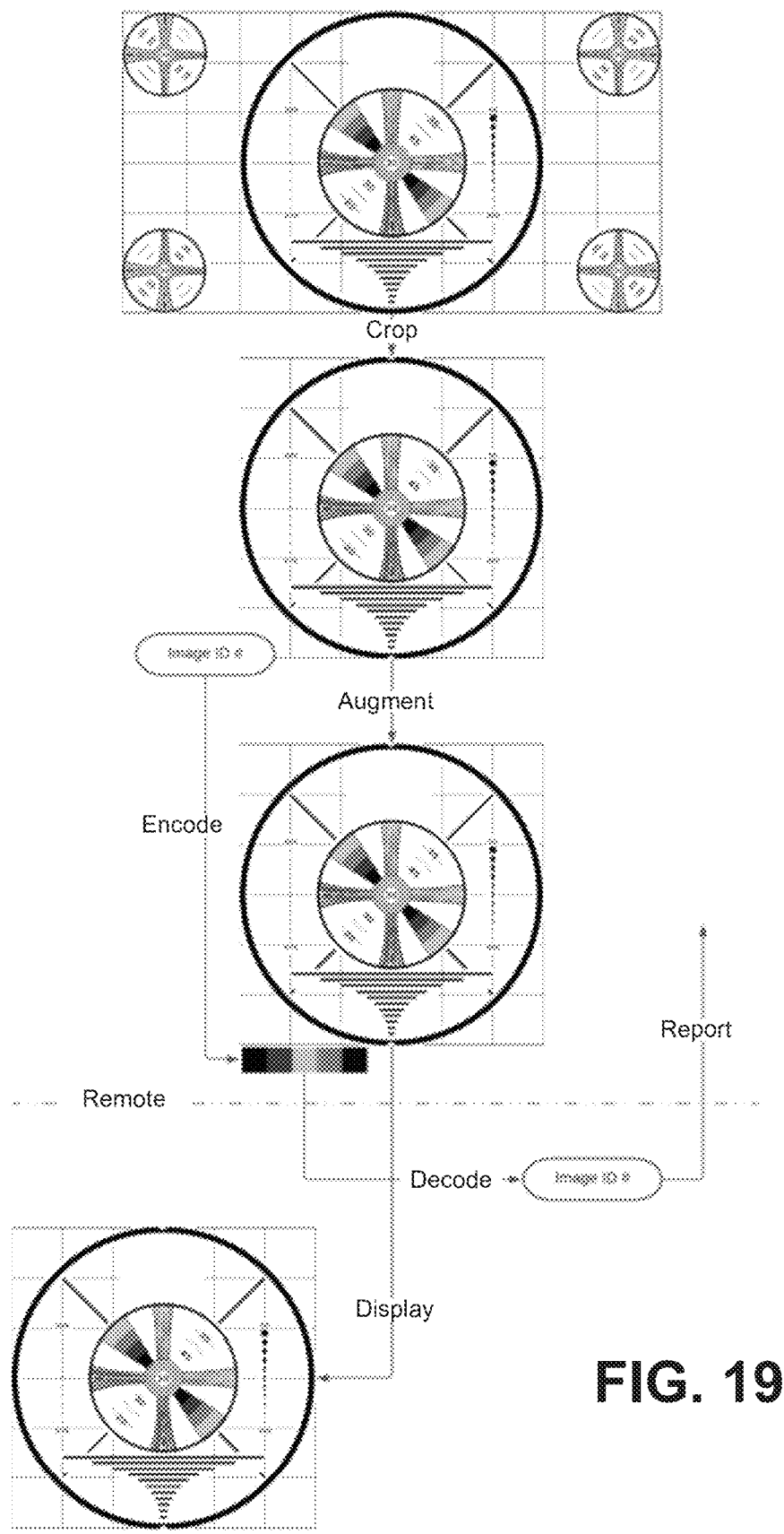
FIG. 19 is a flowchart that depicts an example encoding method for encoding images with unique identifies according to an embodiment.

Next, each of these grey scale colors is painted into 8×8 pixel box. This way, as they are compressed the pixel value of that box remains very close to the original number. An 8×8 pixel box is used because the most common JPEG quantization window is 8×8 pixels. Other size pixel boxes can be used in other examples. For example, H264 uses a 4×4 pixel window, but aggregates into 16×16 overlapping windows which would make every 8×8 pixel block within the 25% error range of our base-four encoding. As one specific example, (128), (128), (0), (64), (192), (192) can be painted into 8×8 pixel boxes and the result is shown in FIG. 18.

Next, eight rows are augmented at the bottom of the image and the encoded pixels are attached. The resulting image is sent to the remote application. As a next step, the system can be configured to pullout the encoded pixels and for each 8×8 pixel box can average the center pixels. The result can be divided by sixty-four to determine the original base-four number.

Finally, the base-four number is converted back to base-ten, along with any additional data that is needed. This encoding method is illustrated visually in FIG. 19.

Examples relevant to heartbeat features and functionality that can be included in some of the systems, methods, and devices described herein will now be described with reference to FIGS. 20-25. First, however, some background information with respect to communicating over a network, such as the internet, will be provided.

When communicating over the internet, for example, in communications between the local and remote components of the systems described herein, internet datagrams (what TCP and UDP layer sends) are broken into smaller chunks of data called packets. In general, packet sizes are decided by the hardware (and/or operating system) linking any two nodes in the system. This can potentially change for every hop in a route. Because the systems described herein may communicate over public network, such as the internet, or other non-local networks, the system is not able to determine the communication route between the local and remote components. Thus, it is generally not possible to know the packet sizes that will be used. On some operating systems, one can see the maximum transmission unit (MTU) for local connections by running $ ip address. An example output of such a command is shown as FIG. 20. Linux systems have implemented an MTU of 1500, and many other systems use this as well. Some older hardware uses an MTU of 567. The minimum defined by the protocols is smaller than the headers for most things. Most literature just leaves it as a variable, and it is believed that 1500 is the most commonly used size.

Figures 20, 21:
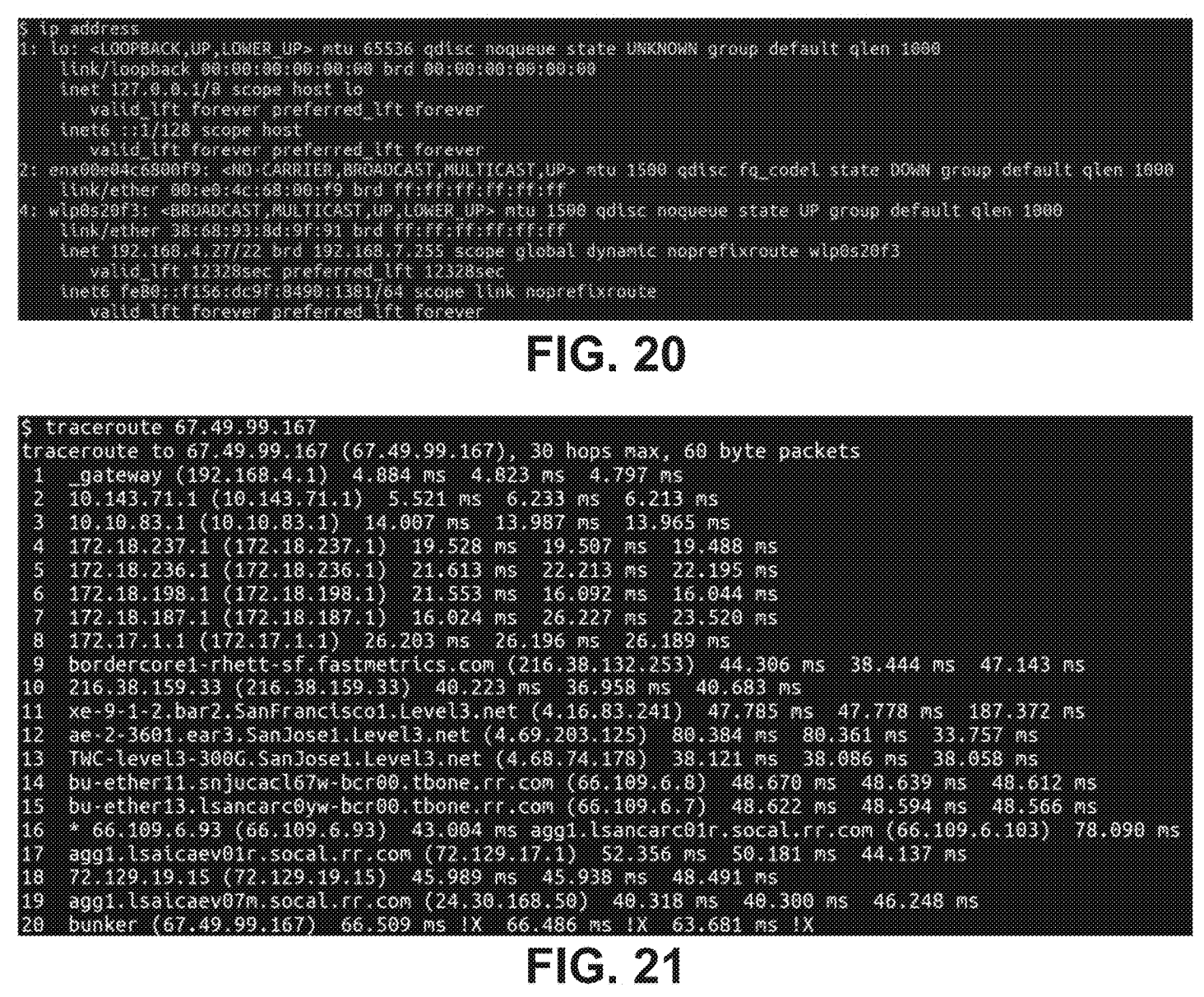

The amount of data that can be sent across the network can be dictated by how long it takes to get a packet across, and how many of the packets we send make it to the other side. FIG. 20 provides an example traceroute readout showing various steps or hops over a communication network. Determination of how long it takes to get a packet across and how many packets make it to the other side cannot be measured with a single query. In fact, the single direction time it takes a packet may not be able to be measured at all.

Figure 22:
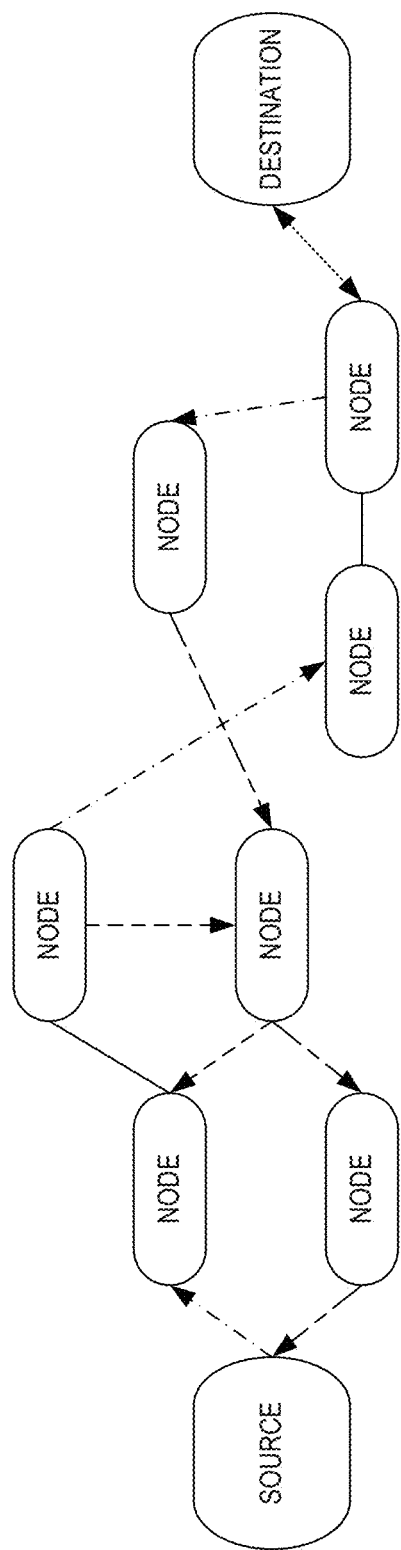
FIG. 22 illustrates example connections between network nodes between a source and a destination according to an embodiment.

Round trip time (RTT) can be calculated by sending a packet smaller than the MTU to destination and having the receiving application send one immediately back. If neither of these packets are dropped then we can use the local clock to time the transmission. A problem arises, however, in that this only determines one path through the internet. The internet is a web and each packet is capable of taking a different route. Thus, a question exists as to how many packets are needed to be sent to trace all of the various routes. FIG. 22 illustrates various routes through various nodes between a source and a destination.

In order to know how much data the system can move it still must be determined how many packets are making it across the network. This can be calculated by sending a number of packets, smaller than the MTU, with unique numbers and counting how many make it to the other side. The question here, again, is how many packets are needed to be sent to get a reliable metric.

Matt Mathis of Google Research and Alfred Morton of AT&T where tasked with answering these questions for the Internet Engineering Steering Group. Their goal was come up with a method of testing a connection speed that could be guaranteed to provided actionable metrics to the ISPs when connection rates dropped below advertised bandwidths. See, for example, https://tools.ietf.org/html/rfc8337, which is incorporated herein by reference. There are two quantities that they were able to calculate that will have direct bearing on the teleoperation systems and methods described herein. They found that by sending a burst of messages, one can cause the packets to take different routes and by using a model one can calculate how many packets that should be. In summary, what they found was that if one makes an a priori estimate of the data rate and RTT, one can calculate the number of messages that need to send in the burst (called target window size). They determined that this is related to maximum carry size of the transmission medium and thus influences number of dropped packets. The present inventors have advantageously determined that this window size can be used to figure out how many bursts are needed to be sent to measure dropped packets for the systems and methods described herein. Most of these equations are derived from the Reno congestion control algorithm implemented by TCP/IP.

For example:

target_window_size: The average number of packets in flight (the window size) needed to meet the Target Data Rate for the specified Target RTT and Target MTU. It implies the scale of the bursts that the network might experience.

The target_run_length is an estimate of the minimum required number of unmarked packets that must be delivered between losses or ECN CE marks, as computed by a mathematical model of TCP congestion control. The derivation here is parallel to the derivation in [MSM097] and, by design, is quite conservative.

window_size=ceiling (target_rate*target_RTT/(target_MTU-header_overhead)) run_length=3*(target_window_size^2).

With this background in mind, a remote application heartbeat feature can be included in the system and methods described herein to further facilitate and enable the safety of such systems and methods. In general, the main purpose of the remote heartbeat is to verify the integrity of the internet connection between the remote browser or user and the local system. The primary concern is that this connection will not fail by being severed, but by the slow degradation of reduced bandwidth and increased latency. Teleoperation is highly sensitive to deviations in latency as it may be needed for the user to verify motion at regular intervals. Thus, in some embodiments, the system can measure the basic connectivity and stop motion when we see connectivity approaching a dangerous level.

In some embodiments, for example, as shown in FIG. 22, a remote connection application, which can be included between the local application and the remote application, can be configured to monitor the connection using, for example, a dedicated WebRTC channel for the remote heartbeat data exchange. Rather than monitor packet loss and bandwidth directly, the system can, in some embodiments, use round trip time (RTT) as a proxy for these values. This can be a valid metric given the number of packets that are sent according to Mathis and Morton. In some embodiments, the system will send packets reliably so that dropped packets will result in re-sending and up RTT on average.

In order to run the calculations from Mathis and Morton, the system may need to project what RTT and data rate that it would like to maintain. For model-based bulk transport metrics, one can only measure to a target RTT and bandwidth. Thus, a chicken and an egg problem arises in that the system needs to establish a base line before it can begin monitoring. While these targets can be configurable, they can have dramatic influence on the result, as the bandwidth needed to monitor the heartbeat can outstrip the needed system bandwidth. Picking too high of a target RTT or too low of a target bandwidth can mean that the metrics will always show that the system is doing better in terms of bandwidth. For example, by picking small RTTs and large bandwidths, the system will always report that we are using too much bandwidth. In some embodiments, these values can be verified by real data from clinical sites and these thresholds can be tuned to report a slow connection whenever system performance degrades. In some embodiments, the targets should be fixed at reasonable values where consistency is more important than accuracy. Then, human factors and system performance should be analyzed as bandwidth is limited to decide reasonable thresholds.

In one example, an RTT from Gualala to Los Angeles has been measured at around 80 ms. Inside the city of LA, RTTs of around 20 ms have been measured. From a slow connection in San Francisco to LA, an RTT of about 60 ms was measured. These seem consistent with the optimistic times ISPs report. Thus, a target RTT of 50 ms may provide a suitable goal to monitor.

Bandwidth usage on a fully local system has been measured at 84942.4 B/s, while measuring across the Gualala to LA connection resulted in a measurement of 63652.9 B/s. This seems somewhat consistent with the RTT data. Thus, for some embodiments, it has been determined that a target bandwidth value of 85 KB/s may be desirable.

In some instances, these RTT and bandwidth values may not be critical as the system can continue to measure its connection relative to this model and that will be consistent as long as it is close enough to get varying results.

Using these values, the following math can be performed to determine that, in some embodiments, the system needs to send bursts of the packets nice times until a total of 27 packets is reached:

target_rate=85000 B/s
target_RTT=0.050 seconds
target_MTU=1500 B
header_overhead=48 B
window_size=ceiling (85000 B/second*0.05 seconds/(1500 B-48 B))=ceil (4250 B/1452 B)=ceil(2.93)=3
run_length=3*(3^2)=27

Additionally, one or more of the following factors may also be considered in configuring the heartbeat. For example, it may be desirable that the heartbeat system is tolerant of packet reordering. This can be accomplished, in some embodiments, by using a reliable connection and a hop/burst number to count each packet that is send. In some embodiments, the time of the slowest packet can be used. In some embodiments, measurements can be made in both directions (e.g., local to remote and remote to local). Connections may not be symmetric so the system can send packets in both directions. In some embodiments, the system is configured to measure the health of the internet itself and limit any delay to other data we may be sending. Accordingly, in some embodiments, the system may use a dedicated data channel for heartbeats. In some embodiments, cycles can be split so that the system does not rely on a continuous flow. This may also allow throttling in low RTT environments.

Figure 23:
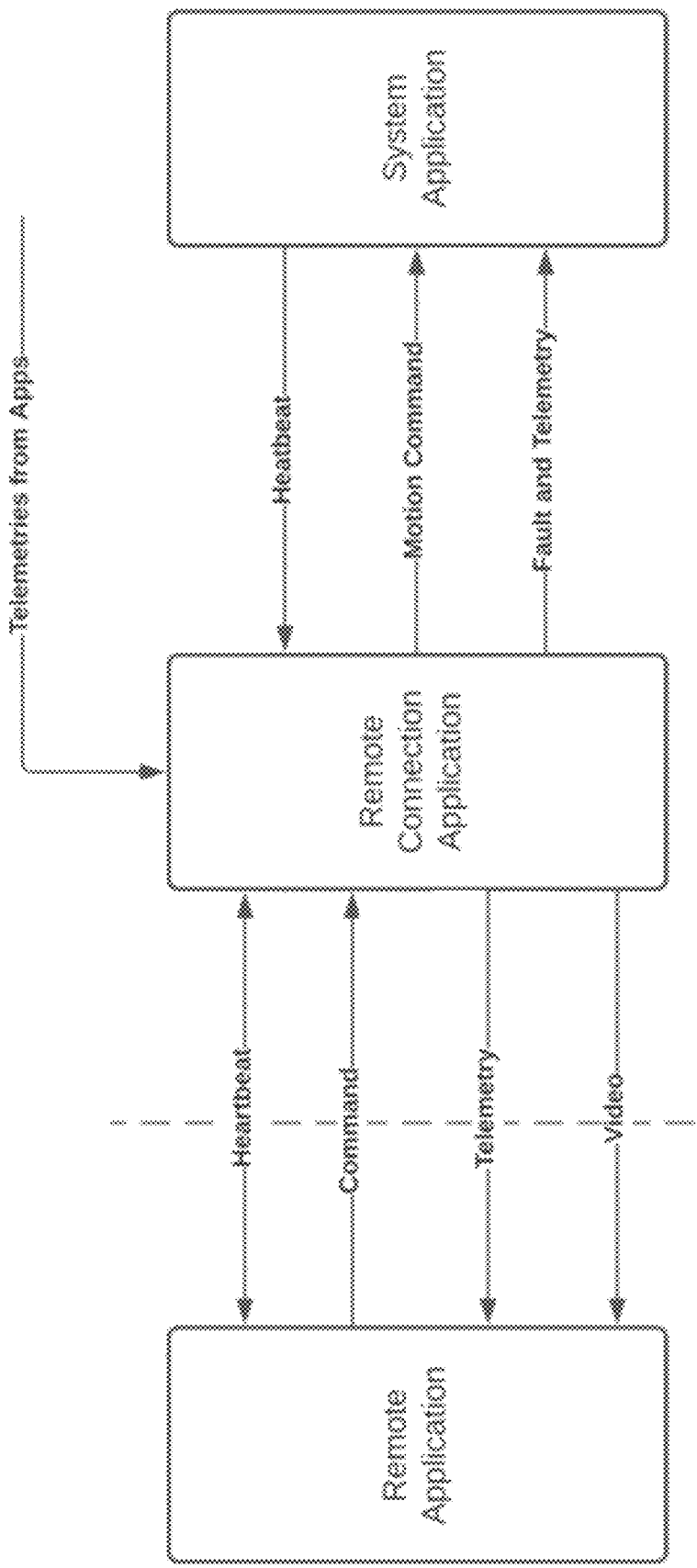
FIG. 23 illustrates data channels between a remote application and a system application according to an embodiment.

FIG. 23 also illustrates the various data channels between the system application, the remote application, and the remote connection application, according to some embodiments.

Figure 24:
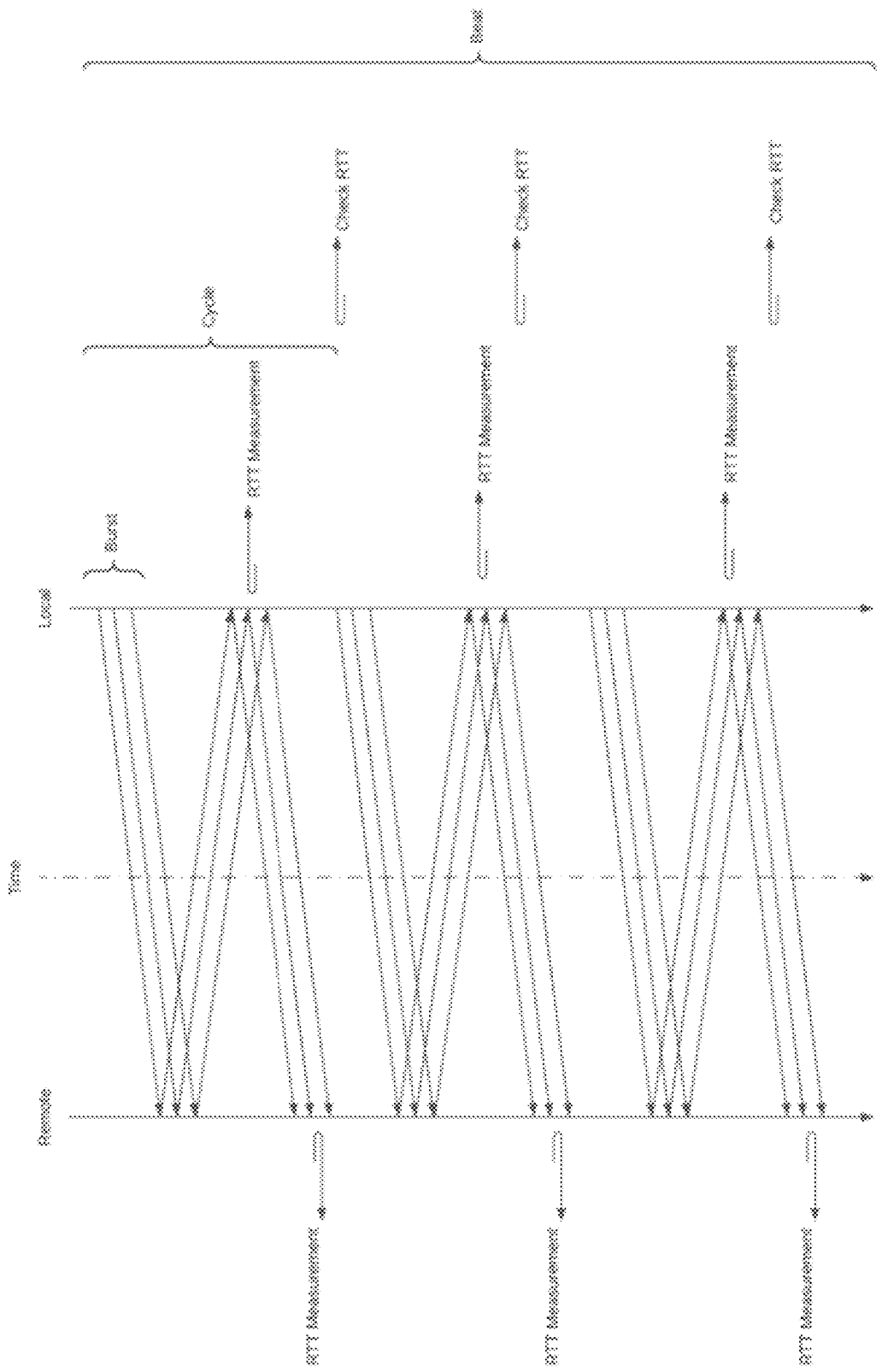
FIG. 24 illustrates an example heartbeat sequence diagram according to an embodiment.
Figure 25:
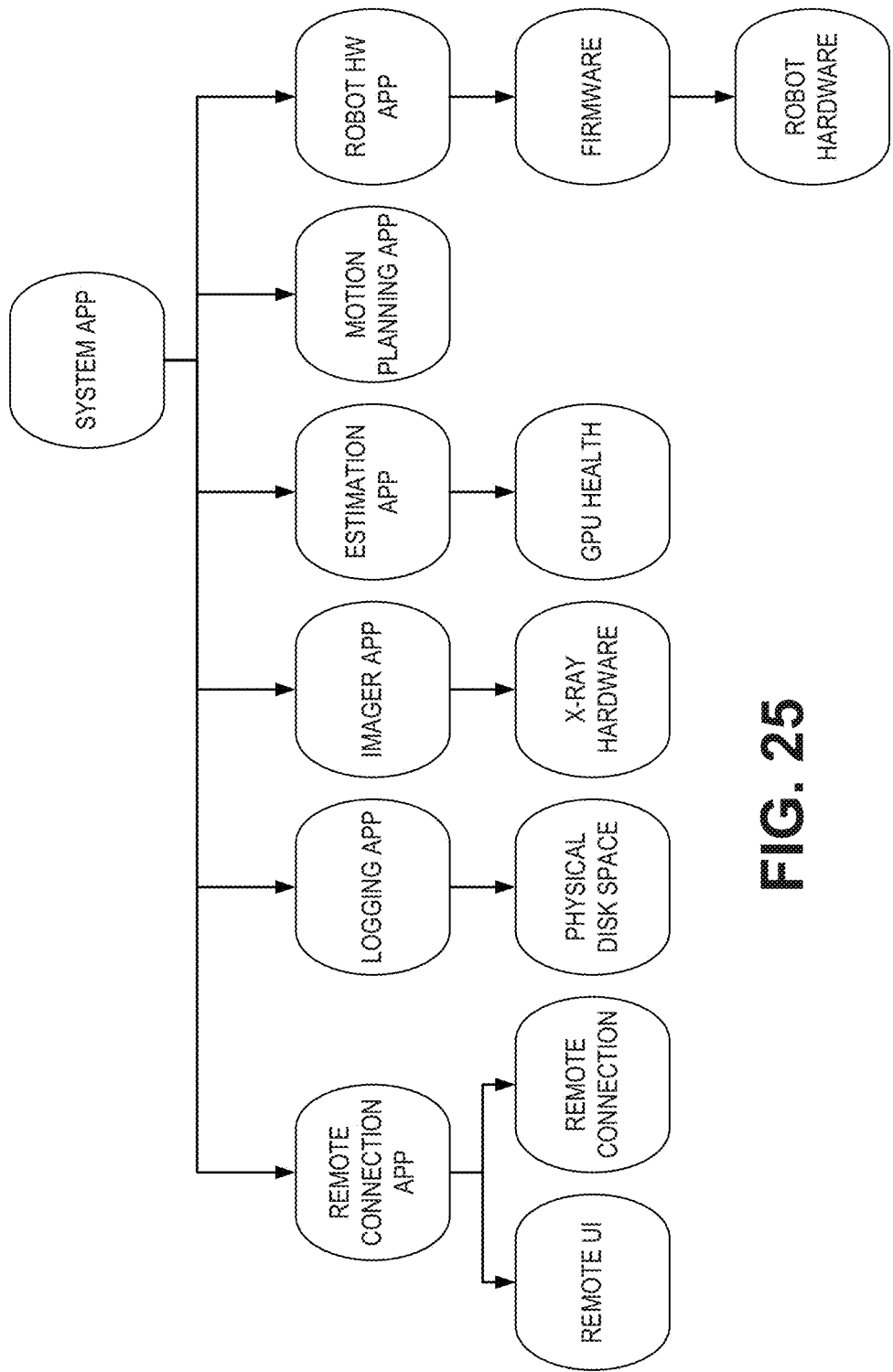
FIG. 25 illustrates an example monitoring hierarchy according to an embodiment.

FIG. 24 illustrates an example heartbeat sequence diagram according to some embodiments. In this example, a packet may comprise a single message smaller than the MTU. In some embodiments, packets are kept small to avoid bandwidth issues, but data must be placed here for the test to be valid. Thus, in some embodiments, the system can incorporate data integrity information (described in more detail below) into the heartbeat message. With reference to FIG. 24, a burst can comprise a sequence of packets sent in one hop. In the illustrated example, there are three packets in each burst. An RTT measurement can be calculated for each direction once per cycle. In some embodiments, this will require three bursts so that each side (local and remote) can send and receive a response. This will consume nine packets. Remote RTT times can be reported for data integrity checks. Finally, each beat can repeat cycles until the target_run_length is reached. For the illustrated example, this is three cycles. Note that expected heartbeat time can be determined as (number of cycles*1.5*RTT). Thus, if we expect (3*1.5*0.05 seconds)=225 ms, we can use windowing to keep a moving average of the last three cycles and this will allow us to do an update after every cycle and cut update to 75 milliseconds.

In some embodiments, the system application (for example, as shown in FIGS. 16, 17, and 24) can be in charge in verifying that some or all components of the system are in proper operational order. However, in some embodiments, it need not do this directly. For example, as shown in the example monitoring hierarchy of FIG. 25, the system application can be configured to monitor a key set of applications to verify that they in proper operational order and reporting updated information. If any of these second tier applications have issues either internally or with the sub-components that they manage then they will go into a fault state and should be sure to include the information needed for the system application to decide the appropriate action it should take to clear faults and resume operation (whether that is to send a clear faults signal to the application, post a message to the user, or even begin log upload and automatically start the complaint investigation process with the FDA). This state is referred to herein as a System App Fault. Monitoring of sub-components by the individual applications will be discussed in the Data Integrity section.

Figure 26:
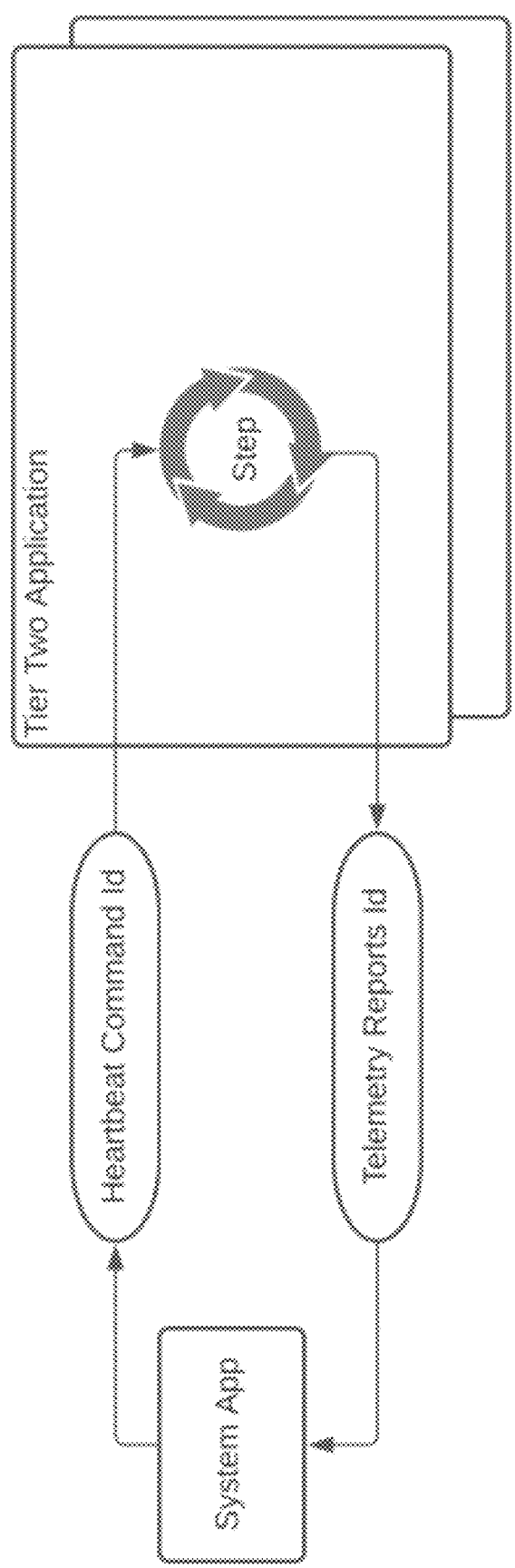
FIG. 26 illustrates an example monitoring method according to an embodiment.

The heartbeat functionality provided by the system application can be configured to check that each of the second-tier applications is receiving commands and processing these into telemetries. If an application can do these two things, then it can guarantee that the application is stepping correctly and would be able to stop its sub-components if it were told to do so, and fault if it had lost communication with any of its subcomponents. The system application can know the loop rate frequency of one or all of the second-tier applications, for example, from the associated configuration files. Thus it will send a command to each application at this frequency. It will then register to listen to the telemetry coming off each of these applications. If the telemetry does not report back an updated command in at least two times the loop rate frequency, then the system application, which serves as a motion gatekeeper, will block all commands into the motion pipeline and begin the process of restarting the effected applications. If all second-tier applications are passing heartbeat checks the system application can check that none of the applications are faulted and block all commands into the motion pipeline. An example is illustrated in FIG. 26.

There are many possibilities of checks for data integrity and clinical monitoring. As used herein, the term data integrity check is used to mean any check that requires knowledge of the specific application and implementation and the failure that will result in system application blocking input into the motion portion of command pipeline (known as a system app fault). Clinical monitoring checks are the same except these checks may require knowledge of the specific clinical procedure being performed. In some embodiments, if a data integrity and clinical monitoring check fails in a tier two application or below, this may result in a fault in the tier two application. In some embodiments, only in situations where a fault cannot be determined locally should the tier two application place the information that is needed into its telemetry so that the system application can aggregate the data with other tier two applications to determine if a fault is required.

Example data integrity checks for the local application can include one or more of the following, among others:
RbtHw: Tracking Error: motors stop following commands.
RbtHw: Velocity request: we asked the hardware for more than we can do.
RbtHw: Firmware Heartbeat lost.
ReConn: Remote Heartbeat check.
Logging App: Hard disk nearing full.
Imager: Can't read image.

Example data integrity checks for the system application can include one or more of the following, among others:
Required app goes down.
RbtHw+Estimator: Difference in linear slide versus tip.
State Mismatch: robot driving while motion app is faulted.

Example clinical monitoring checks can include one or more of the following, among others:
Inside Vessel check.
Prolapse detection.
Manual unexpected C-Arm motion (Optical Flow).
Force maximums.

In some embodiments, the system application may verify that the second-tier applications come up before the procedure starts and remain up until the procedure is concluded.

In some embodiments, the system can be configured to mark a timestamp on the raw images from the imager and verify in the system application that the system is getting recent images moving through the local system. This can be important to implement for safety as the confirmation mechanism is based on sequence numbers which may be susceptible to absolute delay problems if the entire pipeline is delayed. Thus, the system may track that the first image in the chain is on time and the rest will follow.

In some embodiments, the system is configured to send back the remote RTT calculations and verify that they are in agreement with local RTT calculations. This can be considered part of the heartbeat, but may also be considered part of the data integrity checks.

In some embodiments, a WebRTC connection can be configured report general statistics on the video and each data channels. These can be monitored in the remote connection application and fault if it is detected that data has stopped or performance has dropped below configured minimums. Also, logging this data can be key in analyzing connect performance as we move to multiple sites.

Monitoring video can include monitoring of one or more of the following, among others:

Bytes Received: with frames received can give us bytes per frame

Frames Dropped: If we see a spike this could indicate an issue.

Frames Per Second: Will have a clear minimum in which we will stop.

Frames Received: with bytes tells us the bit rate, with dropped tells us loss rate.

Packets Lost: High loss percentage could indicate network problems even if bandwidth remains high.

Packets Received: Need to calculate loss percent.

Last Packet Received Timestamp: Key in identifying a dropped connection early.

Monitoring data can include monitoring of one or more of the following, among others:

Bytes Received: Bytes per message, warn if we go over MTU.

Bytes Sent: Bytes per message, warn if we go over MTU.

Messages Sent: For bytes per message, can be used if periodic messages are expected.

Messages Received: For bytes per message, can be used if periodic messages are expected.

Computer System

Figure 10:
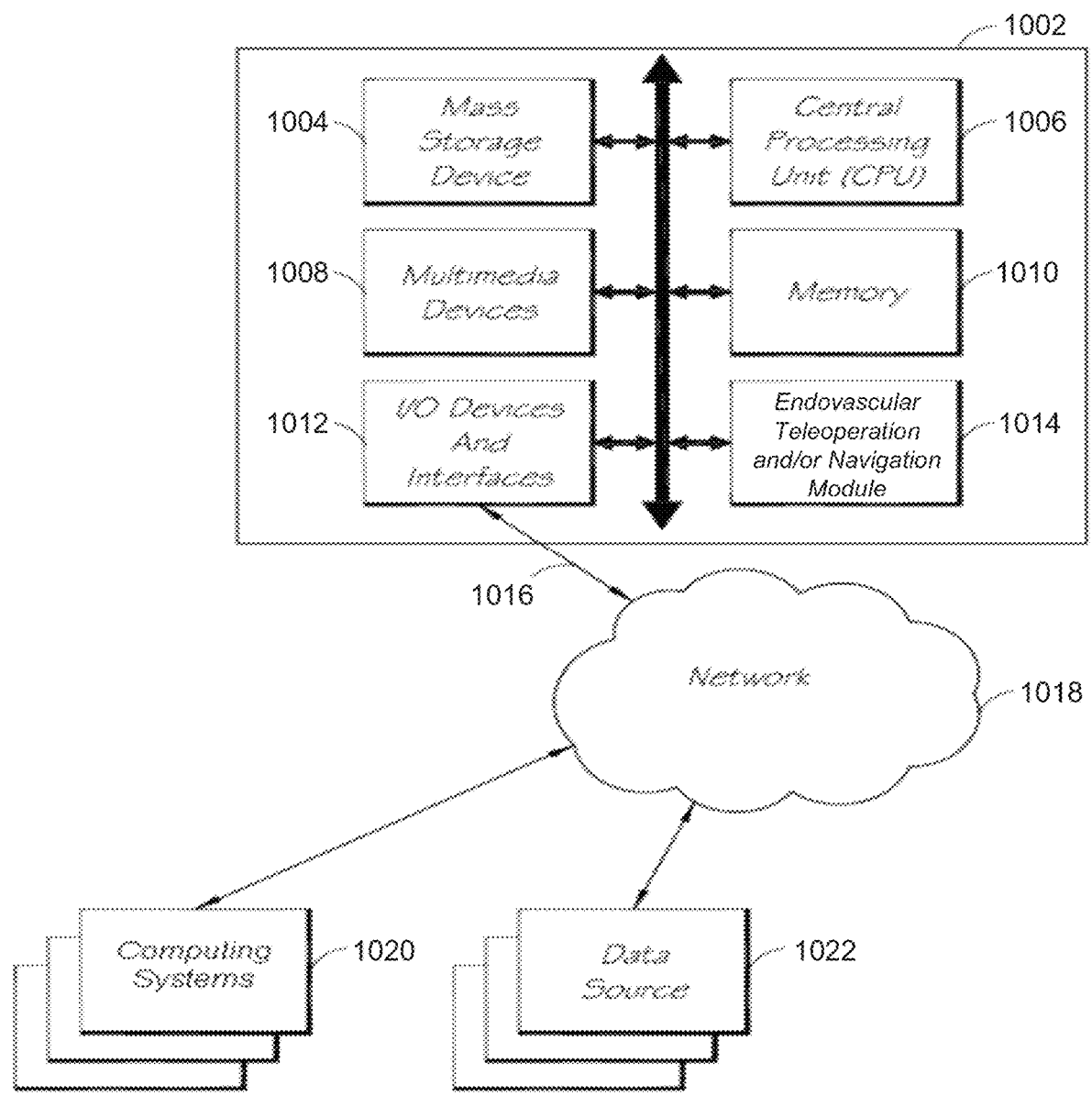
FIG. 10 is a block diagram depicting an embodiment(s) of a computer hardware system configured to run software for implementing one or more embodiments of systems, devices, and methods for guidance of intraluminal and/or endovascular devices within the anatomy.

In some embodiments, the systems, processes, and methods described herein are implemented using a computing system, such as the one illustrated in FIG. 10. The example computer system 1002 is in communication with one or more computing systems 1020 and/or one or more data sources 1022 via one or more networks 1018. While FIG. 10 illustrates an embodiment of a computing system 1002, it is recognized that the functionality provided for in the components and modules of computer system 1002 can be combined into fewer components and modules, or further separated into additional components and modules.

The computer system 1002 can comprise an endovascular teleoperation and/or navigation module 1014 that carries out the functions, methods, acts, and/or processes described herein. The endovascular teleoperation and/or navigation module 1014 is executed on the computer system 1002 by a central processing unit 1006 discussed further below.

In general the word "module," as used herein, refers to logic embodied in hardware or firmware or to a collection of software instructions, having entry and exit points. Modules are written in a program language, such as JAVA, C, or C++, or the like. Software modules can be compiled or linked into an executable program, installed in a dynamic link library, or can be written in an interpreted language such as BASIC, PERL, LAU, PHP or Python and any such languages. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems and can be stored on or within any suitable computer readable medium, or implemented in whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 1002 includes one or more processing units (CPU) 1006, which can comprise a microprocessor. The computer system 1002 further includes a physical memory 1010, such as random-access memory (RAM) for temporary storage of information, a read only memory (ROM) for permanent storage of information, and a mass storage device 1004, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 1002 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1002 includes one or more input/output (I/O) devices and interfaces 1012, such as a keyboard, mouse, touch pad, and printer. The I/O devices and interfaces 1012 can include one or more display devices, such as a monitor, that allows the visual presentation of data to a user. More particularly, a display device provides for the presentation of GUIs as application software data, and multi-media presentations, for example. The I/O devices and interfaces 1012 can also provide a communications interface to various external devices. The computer system 1002 can comprise one or more multi-media devices 1008, such as speakers, video cards, graphics accelerators, and microphones, for example.

Computing System Device/Operating System

The computer system 1002 can run on a variety of computing devices, such as a server, a Windows server, a Structure Query Language server, a Unix Server, a personal computer, a laptop computer, and so forth. In other embodiments, the computer system 1002 can run on a cluster computer system, a mainframe computer system and/or other computing system suitable for controlling and/or communicating with large databases, performing high volume transaction processing, and generating reports from large databases. The computing system 1002 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 1002 illustrated in FIG. 10 is coupled to a network 1018, such as a LAN, WAN, or the Internet via a communication link 1016 (wired, wireless, or a combination thereof). Network 1018 communicates with various computing devices and/or other electronic devices. Network 1018 is communicating with one or more computing systems 1020 and one or more data sources 1022. The endovascular teleoperation and/or navigation module 1014 can access or can be accessed by computing systems 1020 and/or data sources 1022 through a web-enabled user access point. Connections can be a direct physical connection, a virtual connection, and other connection type. The web-enabled user access point can comprise a browser module that uses text, graphics, audio, video, and other media to present data and to allow interaction with data via the network 1018.

The output module can be implemented as a combination of an all-points addressable display such as a cathode ray tube (CRT), a liquid crystal display (LCD), a plasma display, or other types and/or combinations of displays. The output module can be implemented to communicate with input devices 1012 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

Other Systems

The computing system 1002 can include one or more internal and/or external data sources (for example, data sources 1022). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1002 can also access one or more databases 1022. The databases 1022 can be stored in a database or data repository. The computer system 1002 can access the one or more databases 1022 through a network 1018 or can directly access the database or data repository through I/O devices and interfaces 1012. The data repository storing the one or more databases 1022 can reside within the computer system 1002.

URLs and Cookies

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Doman Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Embodiments

It will now be evident to those skilled in the art that there has been described herein methods, systems and devices for improved routing of catheters and other devices to targeted anatomical locations using robotically controlled assemblies. Although the inventions hereof have been described by way of several embodiments, it will be evident that other adaptations and modifications can be employed without departing from the spirit and scope thereof. The terms and expressions employed herein have been used as terms of description and not of limitation; and thus, there is no intent of excluding equivalents, but on the contrary, it is intended to cover any and all equivalents that may be employed without departing from the spirit and scope of the inventions.

While the disclosure has been described with reference to certain embodiments, it will be understood that various changes may be made and equivalents may be substituted for elements thereof without departing from the scope of the disclosure. In addition, many modifications will be appreciated to adapt a particular instrument, situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter or microcatheter" or "advancing one portion of the device (e.g., linearly) relative to another portion of the device to rotate the distal end of the device" include instructing advancing a catheter" or "instructing advancing one portion of the device," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A system for guiding an instrument within a vascular network of a patient from an insertion site to a target site during an endovascular procedure, the system comprising an electronic storage medium storing instructions configured to cause a processor to, for each of a plurality of steps in guiding the instrument through the vascular network to the target site:
    receive a medical image from medical imaging device, wherein the medical image is obtained non-invasively;
    identify, within the medical image, a distal tip of the instrument and a direction of the distal tip of the instrument;
    determine a current position and a current direction of the distal tip of the instrument with respect to a two-dimensional imaging plane of the medical image based on (a) the identified distal tip and the identified direction of the distal tip, (b) one or more past positions and past directions of the distal tip determined during one or more previously executed steps of the plurality of steps, and (c) one or more past trajectory commands generated during one or more previously executed steps of the plurality of steps;
    display the medical image, including an indication of the determined current position and the current direction of the distal tip, on a display device of a user device;
    receive, on an input device of the user device, a selection of a navigation waypoint for movement of the distal tip of the instrument, wherein the selection comprises a pixel or group of pixels on the displayed medical image;
    generate at least one current trajectory command based on the determined current position and the current direction, the at least one current trajectory command for moving the instrument within the vascular network toward the navigation waypoint; and
    provide the at least one current trajectory command to a robotic medical system configured to move the instrument according to the at least one current trajectory command.

2. The system of claim 1, wherein the user device is remotely located relative to the patient, the instrument, and the robotic medical system.

3. The system of claim 1, wherein the user device communicates with the system over a public computer network.

4. The system of claim 1, wherein the user device comprises a personal computer, a laptop, a tablet, or a smartphone.

5. The system of claim 1, wherein the processor is further configured to:
    receive or determine a pathway from the insertion site to the target site;
    for each of the plurality of steps in guiding the instrument along the pathway to the target site:
        determine a suggested navigation waypoint for movement of the distal tip of the instrument;
        display the suggested navigation waypoint on the displayed medical image; and
        wherein receiving, on the input device of the user device, the selection of the navigation waypoint for movement of the distal tip of the instrument comprises receiving a confirmation of the suggested navigation waypoint.

6. The system of claim 1, wherein the endovascular procedure comprises a mechanical thrombectomy for large vessel occlusion stroke treatment.

7. A system for guiding an instrument within a vascular network of a patient, the system comprising an electronic storage medium storing instructions configured to cause a processor to, for each of a plurality of steps in guiding the instrument through the vascular network:
    receive a medical image from a medical imaging device;
    identify, within the medical image, a distal tip of the instrument and a direction of the distal tip of the instrument;
    determine a current position and a current direction of the distal tip with respect to the medical image based on (a) the identified distal tip and the identified direction, (b) one or more past positions and past directions of the distal tip determined during one or more previously executed steps of the plurality of steps, and (c) one or more past trajectory commands generated during one or more previously executed steps of the plurality of steps;
    determine a waypoint for the distal tip of the instrument based at least in part on the determined current position and the current direction of the distal tip; and
    generate at least one current trajectory command based on the determined current position, the determined current direction, and the determined waypoint, the at least one current trajectory command for moving the instrument through the vascular network from the current position to the waypoint.

8. The system of claim 7, wherein determining the current position and current direction of the distal tip with respect to the medical image comprises determining the current position and current direction of the distal tip with respect to a two-dimensional imaging plane of the medical image.

9. The system of claim 7, wherein the processor is further configured to, for each step of the plurality of steps:
    display the medical image, including an indication of the determined current position and the current direction of the distal tip, on a display device of a user device; and
    wherein determining the waypoint is further based on a user input received on an input device of the user device, the user input comprising a selection of a pixel or group of pixels on the displayed relative image.

10. The system of claim 7, wherein, for each step of the plurality of steps, the processor is further configured to determine the waypoint based on a pre-operatively determined pathway through the vascular network.

11. The system of claim 10, wherein, for each step of the plurality of steps, the processor is further configured to:
 display, on the display device, the determined waypoint; and
 prior to generating the at least one trajectory command, receive a user confirmation or a user adjustment of the determined waypoint on the input device.

12. The system of claim 10, wherein the pre-operatively determined pathway through the vascular network is determined based on a pre-operative CT scan.

13. The system of claim 7, wherein the processor is further configured to, for each step of the plurality of steps, provide the at least one current trajectory command to a robotic medical system configured to move the instrument according to the at least one current trajectory command, whereupon the robotic medical system moves the instrument.

14. The system of claim 13, wherein the processor is further configured to, for each of the plurality of steps:
 receive, from a force sensor associated with the instrument, an insertion force measure associated with the execution of the at least one current trajectory command by the robotic medical system; and
 cause the robotic medical system to stop movement of the instrument or retract the instrument when the insertion force measure exceeds a predetermined insertion force limit.

15. The system of claim 7, wherein the processor is further configured to, for each of the plurality of steps, determine whether to inject a contrast material into the vascular network based on a time elapsed since a previous injection of contrast material, a distanced moved by the instrument since a previous injection of contrast material, and/or the determined current position and direction of the distal tip.

16. The system of claim 15, wherein the processor is further configured to, upon a determination to inject the contrast material, provide a command to a robotic medical system configured to move the instrument, whereupon the robotic medical system injects the contrast material according to the command.

17. The system of claim 7, wherein the medical image is obtained non-invasively.

18. The system of claim 7, wherein the processor is further configured to determine whether the patient is a candidate for the endovascular procedures based on analysis of a pre-operative CT scan.

19. The system of claim 18, wherein the analysis of the pre-operative CT scan is configured to identify one or more of the following: coarctation of the aorta, concomitant aortic dissection, ipsilateral carotid stenosis, a presence of an unstable carotid plaque, aortoiliac occlusive disease, right arch/left heart and bilateral femoral artery stenoses precluding vascular access, severe vascular tortuosity, anatomical variants of the aortic arch anatomy, severe intramural calcification, for an aberrant right subclavian artery, and/or a supreme intercostal right vertebral artery origin.

20. The system of claim 7, wherein the processor is configured to identify, within the medical image, the distal tip and the direction of the distal tip based on one or more computer vision models.

* * * * *